US008268880B2

(12) United States Patent
Bachovchin et al.

(10) Patent No.: US 8,268,880 B2
(45) Date of Patent: Sep. 18, 2012

(54) SOFT PROTEASE INHIBITORS AND PRO-SOFT FORMS THEREOF

(75) Inventors: William W. Bachovchin, Cambridge, MA (US); Hung-Sen Lai, Andover, MA (US); Wengen Wu, Medford, MA (US)

(73) Assignee: Trustees of Tufts College, Boston, MA (US)

( * ) Notice: Subject to any disclaimer, the term of this patent is extended or adjusted under 35 U.S.C. 154(b) by 736 days.

(21) Appl. No.: 12/096,876

(22) PCT Filed: Dec. 15, 2006

(86) PCT No.: PCT/US2006/047853
§ 371 (c)(1),
(2), (4) Date: Dec. 15, 2008

(87) PCT Pub. No.: WO2007/100374
PCT Pub. Date: Sep. 7, 2007

(65) Prior Publication Data
US 2009/0124559 A1    May 14, 2009

Related U.S. Application Data

(60) Provisional application No. 60/752,017, filed on Dec. 19, 2005.

(51) Int. Cl.
*A61K 31/401* (2006.01)
*C07D 295/194* (2006.01)

(52) U.S. Cl. ........................................ 514/423; 548/540

(58) Field of Classification Search .................. 514/423; 548/540
See application file for complete search history.

(56) References Cited

U.S. PATENT DOCUMENTS

| | | | |
|---|---|---|---|
| 5,939,560 A * | 8/1999 | Jenkins et al. | 548/535 |
| 6,890,904 B1 | 5/2005 | Wallner et al. | |
| 2003/0153509 A1 | 8/2003 | Bachovchin et al. | |
| 2004/0072892 A1* | 4/2004 | Fukushima et al. | 514/423 |
| 2004/0229820 A1* | 11/2004 | Bachovchin et al. | 514/19 |
| 2005/0203027 A1* | 9/2005 | Bachovchin et al. | 514/17 |

FOREIGN PATENT DOCUMENTS

| | | | |
|---|---|---|---|
| JP | 03-220179 | * | 9/1991 |
| WO | WO-93/10127 | | 5/1993 |
| WO | WO-95/11689 | | 5/1995 |
| WO | WO 03/045228 | * | 6/2003 |
| WO | WO 2005-082348 A2 | | 9/2005 |

OTHER PUBLICATIONS

Stockel-Maschek et al., "Potent Inhibitors of Dipeptidyl Peptidase IV and Their Mechanisms of Inhibition", Cellular Peptidases in Immune Functions and Diseases 2, Ed. Langer and Ansorge, Kluwer Academic/Plenum Publishers, 2000.*
Coutts et al., "Structure-Activity Relationships of Boronic Acid Inhibitors of Dipeptidyl Peptidase IV. Variation of the P2 Position of Xaa-boroPro Dipeptides", Journal of Medicinal Chemistry, 39(10), 2087-2094, 1996.*
Snow, Roger J. et al., "Boronic Acid Inhibitors of Dipeptidyl Peptidase IV: A New Class of Immunosuppressive Agents", Advances in Medicinal Chemistry, vol. 3, 149-177, 1995.*
Stockel-Maschek, A. et al, "Thioxo Amino Acid Pyrrolidides and Thiazolildides: New Inhibitors of Proline Specific Peptidases", Biochimica et Biophysica Acta, 1479(1-2), 15-31, 2000.*
Lankas, George R. et al., "Dipeptidyl Peptidase IV Inhibition for the Treatment of Type 2 Diabetes. Potential Importance of Selectivity Over Dipeptidyl Peptidases 8 and 9", Diabetes, 54(10), 2988-2994, Oct. 2005.*
Supplementary Partial European Search Report for EP 06 84 9964 completed Jan. 21, 2010.
Schutkowski, M. et al., "Influence on Proline-Specific Enzymes of a Substrate Containing the Thioxoaminoacyl-prolyl Peptide Bond," Eur. J. Biochem. 227:455-461 (1994).
Snow, R. J. et al., "Studies on Proline Boronic Acid Dipeptide Inhibitors of Dipeptidyl Peptidase IV: Identification of a Cyclic Species Containing a B—N Bond", *J. Am. Chem. Soc.*, 116(24):10860-10869 (American Chemical Society, 1994).
International Search Report dated Jul. 31, 2008.

* cited by examiner

*Primary Examiner* — Joseph Kosack
(74) *Attorney, Agent, or Firm* — Dana M. Gordon; Foley Hoag LLP

(57) ABSTRACT

The invention provides compounds and methods for inhibiting proteases. One aspect of the invention features pro-soft inhibitors which react with an activating protease to release an active inhibitor moiety in proximity to a target protease. In certain instances, compounds inhibit proteasomes and/or post-proline cleaving enzymes (PPCE), such as dipeptidyl peptidase IV. The compounds of the invention provide a better therapeutic index, owing in part to reduced toxicity and/or improved specificity for the targeted protease.

16 Claims, 32 Drawing Sheets

Thioxamide trans        cis        deboronated

Oxoamide trans        cis        cyclo low ⇐ pH ⇒ high

PID 2243: Ala-boroPro thioxo amide

Ala-boroPro thioxoamide

NVP LAF327

|  | Ki (DPP IV) | IC$_{50}$ DPP IV | IC$_{50}$ DP8 | IC$_{50}$ DP9 |
|---|---|---|---|---|
| Ala-boroPro Thioxoamide | 27 pM | 0.7 nM | 3.8 nM | 8.4 nM |
| NVP LAF237 | 27 nM | 58 nM | 140 nM | 110 nM |
| MK0431 | 15 nM | 71 nM | 10 $\mu$M | 25 $\mu$M |

SOFT PROTEASE INHIBITORS AND PRO-SOFT FORMS THEREOF

RELATED APPLICATIONS

This application claims the benefit of priority to Patent Cooperation Treaty Application number PCT/US2006/047853, filed Dec. 15, 2006; which claims the benefit of priority to U.S. Provisional Patent Application Ser. No. 60/752,017, filed Dec. 19, 2005.

BACKGROUND OF THE INVENTION

Proteases are enzymes that cleave proteins at specific peptide bonds. Proteases can be classified into four generic classes: serine, thiol or cysteinyl, acid or aspartyl, and metalloproteases (Cuypers et al., *J. Biol. Chem.* 1982, 257, 7086. Proteases are essential to a variety of biological activities, such as digestion, formation and dissolution of blood clots, reproduction, and immune reaction to foreign cells and organisms. However, aberrant proteolysis is associated with a number of diseases in humans and other mammals. Accordingly, it is often beneficial to disrupt the function of one or more proteolytic enzymes in the course of treating a patient.

The binding site for a peptide substrate consists of a series of "specificity subsites" across the surface of the enzyme. The term "specificity subsite" refers to a pocket or other site on the enzyme capable of interacting with a portion of a substrate for the enzyme. In discussing the interactions of peptides with proteases, e.g., serine and cysteine proteinases, the present application utilizes the nomenclature of Schechter and Berger (*Biochem. Biophys. Res. Commun.* 1967, 27, 157-162). The individual amino acid residues of a substrate or inhibitor are designated P1, P2, etc. and the corresponding subsites of the enzyme are designated S1, S2, etc., starting with the carboxy terminal residue produced in the cleavage reaction. The scissile bond of the substrate is the amide bond between P1-P1' of the substrate. Thus, for a peptide Xaa1-Xaa2-Xaa3-Xaa4, which is cleaved between the Xaa3 and Xaa4 residues, the Xaa3 residue is referred to as the PI residue and binds to the S1 subsite of the enzyme, Xaa2 is referred to as the P2 residue and binds to the S2 subsite, and so forth.

Dipeptidyl peptidase IV (DPIV or DPPIV) is a serine protease that cleaves N-terminal dipeptides from a peptide chain containing, preferably, a proline residue in the penultimate position, e.g., in the P1 position. DPIV belongs to a group of cell-membrane-associated peptidases and, like the majority of cell-surface peptidases, is a type II integral membrane protein, being anchored to the plasma membrane by its signal sequence. DPIV is found in a variety of differentiated mammalian epithelia, endothelia and hematopoetic cells and tissues, including those of lymphoid origin where it is found specifically on the surface of CD4$^+$ T cells. DPIV has been identified as the leukocyte differentiation marker CD26.

Proteasomes are cellular complexes comprising proteases responsible for the majority of intracellular protein turnover in eukaryotic cells, including proteolytic degradation of damaged, oxidized or misfolded proteins, as well as processing or degradation of key regulatory proteins required for various cellular functions, such as cell cycle progression. For example, the 26S proteasome is a multi-catalytic protease comprising at its catalytic core the 20S proteasome, a multi-subunit complex of approximately 700 kDa molecular weight. While serving an essential physiological role, the proteasome is also responsible for the inappropriate or accelerated protein degradation that occurs as a result or cause of pathological conditions in which normal cellular processes become disregulated. One notable example is cancer, in which the unregulated proteasome-mediated degradation of cell cycle regulatory proteins, including cyclins, cyclin dependent kinase inhibitors, and tumor suppressor genes, results in accelerated and uncontrolled mitosis, thereby promoting cancer growth and spread. (Goldberg et al. *Chem. & Biol.* 1995, 2, 503-508; Coux et al. *Ann. Rev. Biochem.,* 1996, 65, 801-847; Deshaies, *Trends Cell Biol.* 1995, 5, 428-434). Inhibition of proteasome enzymatic function holds promise in arresting or blunting disease progression in disease states such as cancer or inflammation.

Proteasome inhibitors, e.g., lactacystin and its analogs, have been shown to block the development of the preerythrocytic and erythrocytic stages of Plasmodium spp, the malaria parasites. During both its hepatic and erythrocytic stages, the parasite undergoes radical morphological changes and many rounds of replication, events that likely require proteasome activity. Lactacystin has been found to covalently modify the catalytic N-terminal threonines of the active sites of proteasomes, inhibiting the activity of all proteasomes examined, including those in mammalian cells, protozoa, and archeae. (Gantt et al. *Antimicrob. Agents Chemother.* 1998, 42, 2731-2738).

The human fibroblast activation protein (FAPα) is a $M_r$ 95,000 cell surface molecule originally identified with monoclonal antibody (mAb) F19 (Rettig et al. *Proc. Natl. Acad. Sci. USA* 1988, 85, 3110-3114; Rettig et al. *Cancer Res.* 1993, 53, 3327-3335). The FAPα cDNA codes for a type II integral membrane protein with a large extracellular domain, transmembrane segment, and short cytoplasmic tail (Scanlan et al. *Proc. Natl. Acad. Sci. USA* 1994, 91, 5657-5661; WO 97/34927). FAPα shows 48% amino acid sequence identity to the T-cell activation antigen CD26, also known as dipeptidyl peptidase IV (DPP IV), a membrane-bound protein with dipeptidyl peptidase activity (Scanlan et al.). FAPα has enzymatic activity and is a member of the serine protease family, with serine 624 being critical for enzymatic function (WO 97/34927). Work using a membrane overlay assay revealed that FAPα dimers are able to cleave Ala-Pro-7-amino-4-trifluoromethyl coumarin, Gly-Pro-7-amino-4-trifluoromethyl coumarin, and Lys-Pro-7-amino-4-trifluoromethyl coumarin dipeptides (WO 97/34927).

FAPα is selectively expressed in reactive stromal fibroblasts of many histological types of human epithelial cancers, granulation tissue of healing wounds, and malignant cells of certain bone and soft tissue sarcomas. Normal adult tissues are generally devoid of detectable FAPα, but some foetal mesenchymal tissues transiently express the molecule. In contrast, most of the common types of epithelial cancers, including >90% of breast, non-small-cell lung, and colorectal carcinomas, contain FAPα-reactive stromal fibroblasts (Scanlan et al.). These FAPα$^+$ fibroblasts accompany newly-formed tumor blood vessels, forming a distinct cellular compartment interposed between the tumor capillary endothelium and the basal aspect of malignant epithelial cell clusters (Welt et al. *J. Clin. Oncol.* 1994, 12, 1193-1203). While FAPα$^+$ stromal fibroblasts are found in both primary and metastatic carcinomas, the benign and premalignant epithelial lesions tested (Welt et al.), such as fibroadenomas of the breast and colorectal adenomas, only rarely contain FAPα$^+$ stromal cells. Based on the restricted distribution pattern of FAPα in normal tissues and its uniform expression in the supporting stroma of many malignant tumors, clinical trials with $^{131}$I-labeled mAb F19 have been initiated in patients with metastatic colon carcinomas (Welt et al.).

SUMMARY OF THE INVENTION

One aspect of the present invention features compounds which inhibit a protease. In certain instances, the compound is a pro-soft inhibitor. The pro-soft inhibitor is an inactive agent that is activated, i.e., cleaved by an "activating protease," to release an active inhibitor moiety in proximity to a "target protease." The identity of the activating protease and target protease can be the same or different. After activation of the pro-soft inhibitor, the active inhibitor moiety undergoes self-inactivation by proto-deboronation. Another aspect of the present invention is that the irreversible proto-deboronation step produces innocuous boric acid, which is expected to yield an improved safety profile (fewer side effects).

The invention features inhibitors for a wide array of proteases. For example, the inhibitor of the invention may inhibit post-proline cleaving enzymes (PPCE), such as dipeptidyl peptidase IV. In certain instances, the inhibitor of the invention inhibits proteasome activity. In other instances, the invention provides a pro-soft inhibitor that is activated by a fibroblast activation protein to release a compound that inhibits prostrate specific antigen (PSA). In still other instances, the invention provides a pro-soft inhibitor that is activated by a prostrate specific antigen (PSA) to release a compound that inhibits proteasome activity. In a certain embodiment, the present invention provides pro-soft inhibitors which inhibit post-proline cleaving enzymes, such as dipeptidyl peptidase IV.

Certain compounds of the invention have extended duration. Accordingly, in certain certain embodiments, the inhibitor is selected, and the amount of inhibitor formulated, to provide a dosage which inhibits serum DPP IV levels by at least 50% for at least 4 hours after a single dose, and even more preferably for at least 8 hours or even 12 or 16 hours after a single dose. For instance, in certain embodiments, the dosage is selected in an amount effective to improve one or more aberrant indices associated with glucose metabolism disorders (e.g., glucose intolerance, insulin resistance, hyperglycemia, hyperinsulinemia and Type I and II diabetes) over a 24 hour period.

Another aspect of the invention relates to a method of treating disorders and conditions by administering a protease inhibitor of the invention. In certain instances, the disorder is one that is mediated by DPP IV. In certain instances, the subject inhibitors can be used to up-regulate GIP and GLP-1 activities, e.g., by increasing the half-life of those hormones or as part of a treatment for regulating glucose levels and/or metabolism. In certain instances, the inhibitors can be used to reduce insulin resistance, treat hyperglycemia, hyperinsulinemia, obesity, hyperlipidemia, hyperlipoprotein-emia (such as chylomicrons, VLDL and LDL), and/or regulate body fat and more generally lipid stores. In certain instances, the inhibitors of the invention may be used to treat metabolism disorders, such as those associated with diabetes, obesity and atherosclerosis. While not wishing to be bound by any particular theory, it is observed that compounds which inhibit DPP IV are able to improve glucose tolerance through mechanisms involving DPP IV inhibition.

In other embodiments, the invention features a method of administering a DPP IV pro-soft inhibitor in an amount effective to improve aberrant indices associated with obesity. Fat cells release the hormone leptin, which travels in the bloodstream to the brain and, through leptin receptors there, stimulates production of GLP-1. GLP-1, in turn, produces the sensation of being full. The leading theory is that the fat cells of most obese people probably produce enough leptin, but leptin may not be able to properly engage the leptin receptors in the brain, and so does not stimulate production of GLP-1. There is accordingly a great deal of research towards utilizing preparations of GLP-1 as an appetite suppressant. The subject method provides a means for increasing the half-life of both endogenous and ectopically added GLP-1 in the treatment of disorders associated with obesity.

DPP IV inhibitors have hypoglycemic and antidiabetic activities, and can be used in the treatment of disorders marked by aberrant glucose metabolism (including storage). In particular embodiments, the inhibitors of the invention are useful as insulinotropic agents, or to potentiate the insulinotropic effects of such molecules as GLP-1. In this regard, the invention also provides methods for the treatment and/or prophylaxis of a variety of disorders, including one or more of: hyperlipidemia, hyperglycemia, glucose tolerance insufficiency, insulin resistance and diabetic complications.

Another aspect of the invention features methods and pro-soft inhibitor compounds for altering the pharmokinetics of a variety of different polypeptide hormones by inhibiting the proteolysis of one or more peptide hormones by DPP IV or some other proteolytic activity. For instance, post-secretory metabolism is an important element in the overall homeostasis of regulatory peptides, and the other enzymes involved in these processes may be suitable targets for pharmacological intervention by the subject method. In certain instances, the subject method can be used to increase the half-life of other proglucagon-derived peptides, such as glicentin (corresponding to PG 1-69), oxyntomodulin (PG 33-69), glicentin-related pancreatic polypeptide (GRPP, PG 1-30), intervening peptide-2 (IP-2, PG 111-122amide), and glucagon-like peptide-2 (GLP-2, PG 126-158). GLP-2, for example, has been identified as a factor responsible for inducing proliferation of intestinal epithelium. See, e.g., Drucker et al. *Proc. Natl. Acad. Sci. USA* 1996, 93, 7911. The DPP IV inhibitors can also be used as part of a regimen for treating injury, inflammation or resection of intestinal tissue, e.g., where enhanced growth and repair of the intestinal mucosal epithelial is desired, such as in the treatment of Crohn's disease or Inflammatory Bowel Disease (IBD).

Another aspect of the invention relates to a method of treating growth hormone deficient children or improving nutrition or altering body composition (muscle vs. fat) in adults. DPP IV has been implicated in the metabolism and inactivation of growth hormone-releasing factor (GHRF). GHRF is a member of the family of homologous peptides that includes glucagon, secretin, vasoactive intestinal peptide (VI), peptide histidine isoleucine (PHI), pituitary adenylate cyclase activating peptide (PACAP), gastric inhibitory peptide (GIP) and helodermin. Kubiak et al. *Peptide Res.* 1994, 7, 153. GHRF is secreted by the hypothalamus, and stimulates the release of growth hormone (GH) from the anterior pituitary. The subject method can also be used in veterinary practice, for example, to develop higher yield milk production and higher yield, leaner livestock.

The DPP IV inhibitors of the invention can be used to alter the plasma half-life of secretin, VIP, PHI, PACAP, GIP and/or helodermin. In certain instances, the inhibitors can also be used to alter the pharmacokinetics of Peptide YY and neuropeptide Y, both members of the pancreatic polypeptide family, because DPP IV has been implicated in the processing of those peptides in a manner which alters receptor selectivity. In other embodiments, the DPP IV inhibitors can be used to stimulate hematopoiesis. In still other embodiments, the DPP IV inhibitors can be used to inhibit growth or vascularization of transformed cells/tissues, e.g., to inhibit cell proliferation such as that associated with tumor growth and metastasis, and for inhibiting angiogenesis in an abnormal proliferative cell mass. In yet other embodiments, the subject DPP IV inhibitors can be used to reduce immunological responses, e.g., as an immunosuppressant.

In yet other examples, the DPP IV inhibitors according to the present invention can be used to treat CNS maladies such as strokes, tumors, ischemia, Parkinson's disease, memory loss, hearing loss, vision loss, migraines, brain injury, spinal cord injury, Alzheimer's disease and amyotrophic lateral sclerosis (which has a CNS component). Additionally, the DPP IV inhibitors can be used to treat disorders having a more peripheral nature, including multiple sclerosis and diabetic neuropathy.

Another aspect of the present invention provides a method for stimulating hematopoietic cells in culture or in vivo. In certain embodiments, the subject DPP IV pro-inhibitors include an address moiety that is a substrate for a protease that is expressed in bone marrow. The DPP IV inhibitors of the invention can be used to restore or prevent a deficiency in hematopoietic cell number in a subject. Such deficiencies can arise, for example, from genetic abnormalities, disease, stress, chemotherapy, and radiation treatment.

Another aspect of the present invention features compounds which inhibit proteasome function. In certain embodiments, the pro-soft inhibitors produce inhibitor moieties that are potent and highly selective proteasome inhibitors and can be employed to inhibit proteasome function. Inhibition of proteasome function has a number of practical therapeutic and prophylactic applications. For instance, the proteasome pro-inhibitors embodiments can include address moieties that are substrates for proteases that are expressed in tumors or other cells which are undergoing unwanted proliferation, or expressed in the tissue surrounding the tumor or other target proliferating cells.

In certain embodiments, the proteasome pro-inhibitors of the present invention provide a method of reducing the rate of degradation of tumor suppressors. In other embodiments, compounds of the present invention inhibit the growth of cancer cells. In yet other embodiments, the compounds of the present invention can be formulated in topical form for treatment of skin disorders. Such pro-inhibitors are contemplated as possessing important practical application in treating cell proliferative diseases, such as cancer, restenosis, and psoriasis.

BRIEF DESCRIPTION OF THE DRAWINGS

FIG. 18 depicts $K_1$ and $IC_{50}$ values for Ala-boroPro Thioxamide, NVP LAF327, and MK0431.

DETAILED DESCRIPTION OF THE INVENTION

Overview

Figure 1:
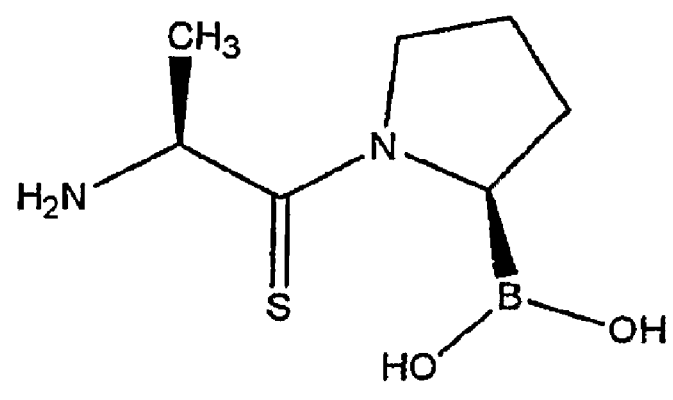
FIG. 1 depicts Ala-boroPro Thioxamide.
Figure 2:
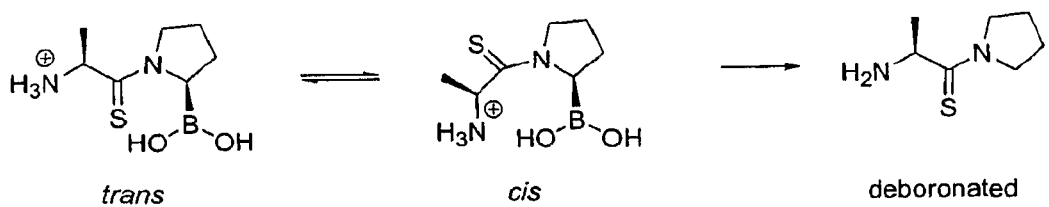
FIG. 2 depicts the pH-dependent behavior of Ala-boroPro Thioxamide and Ala-boroPro.
Figure 2:
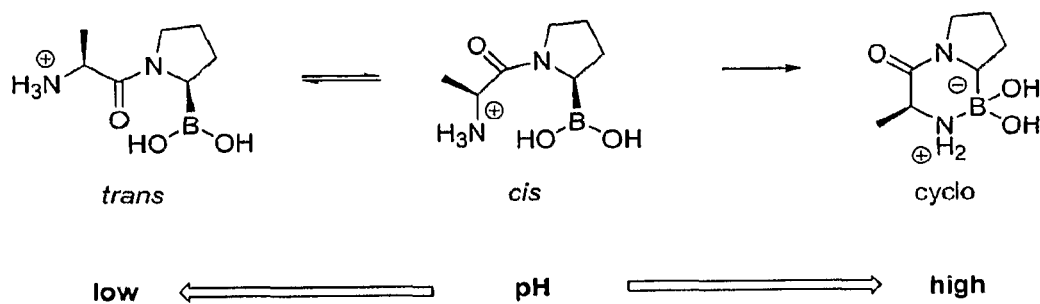
Figure 3:
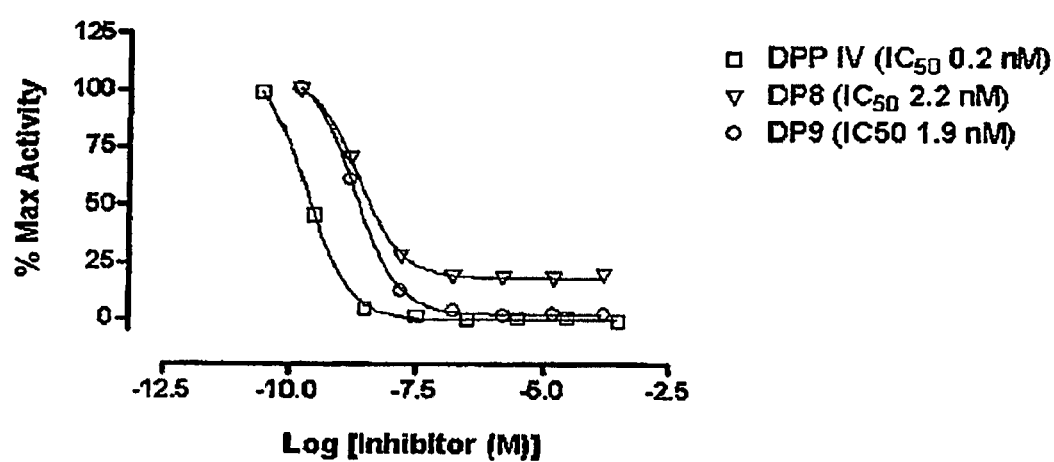
FIG. 3 depicts a comparison of the $IC_{50}$ value of Ala-boroPro Thioxamide against DPP IV, DP8, and DP9. $IC_{50}$ values for Ala-boroPro Thioxamide inhibition of DPP IV, DP8 and DP9 were measured in 50 mM sodium phosphate at pH 7.8. Inhibitor and enzyme were incubated at various inhibitor concentrations prior to addition of the substrate Ala-Pro-paranitroanalide at a concentration equal to the $K_m$ for each enzyme (20 μM for DPP IV and 100 μM for DP8 and DP9.) Reaction mixtures were incubated at 37° C. for 30 min and then the absorbance at 410 nm was read. Data were normalized to the uninhibited reaction rate for each enzyme.
Figure 4:
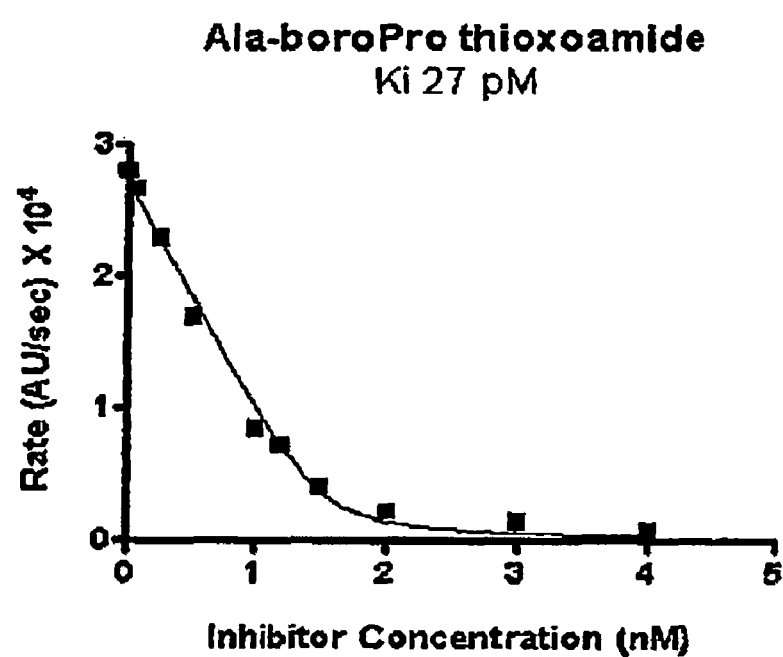
FIG. 4 depicts the $K_i$ of Ala-boroPro Thioxamide in an assay measuring inhibition of DPP IV. Purified DPP IV from human placenta was incubated with inhibitor in 50 mM HEPES, pH 8.0, 0.14 M NaCl at 23° C. to allow complete binding. The chromogenic substrate Ala-Pro-paranitroanalide was added to the enzyme inhibitor complex at 5 times the $K_m$ value and the reaction was monitored by measuring the absorbance at 410 nm for 2 min. Enzyme concentration was determined independently. The Rate vs. Inhibitor concentration was fit to a simple equilibrium model to obtain the value of $K_i$ (Gutheil and Bachovchin, 1993 Biochemistry 32(34) 8723-8731).
Figure 5:
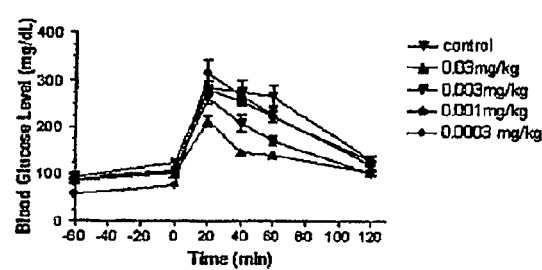
FIG. 5 depicts the results from an oral glucose challenge using Ala-boroPro Thioxamide. Following an overnight fast, seven C57BL/6 mice were given the drug or vehicle (0.25% methylcellulose), by oral gavage, two hours before an oral dose of 5 g/kg glucose. Blood was taken from the tail vein and glucose measured with a freestyle blood glucose meter just before the drug, before glucose, and at 20, 40, 60 and 120 min after the glucose. AUC was calculated for the data from zero to 120 min.
Figure 5:
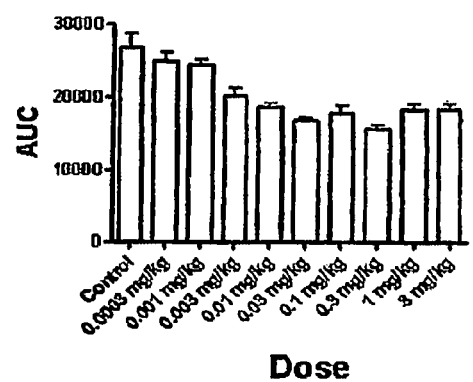
Figure 6:
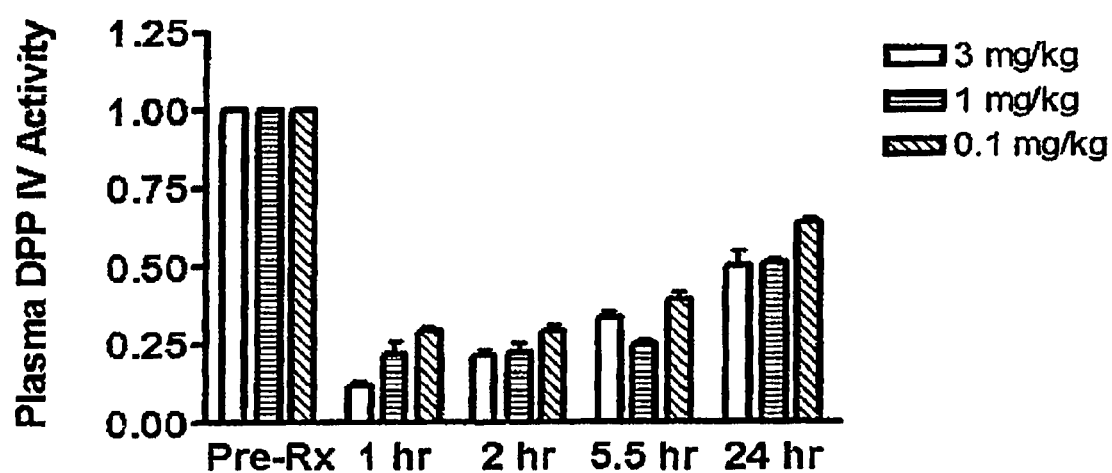
FIG. 6 depicts the results of rat plasma DPP IV inhibition using Ala-boroPro Thioxamide. Groups of four rats were given each dose of Ala-Pro thioxamide. Blood samples were taken from the tail vein and plasma DPP IV was measured by addition of 10 μL of plasma to 150 μL of 30 μM Ala-Pro paranitroanalide in 50 mM HEPES, pH 8, 0.14 M NaCl. The change in absorbance at 410 nm was recorded after 1 hour. The data was normalized to the average pre-dose value for each group.
Figure 7:
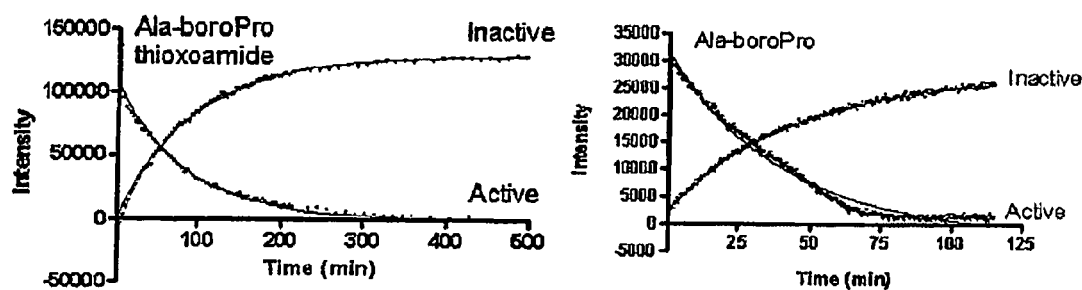
FIG. 7 depicts inactivation of Ala-boroPro Thioxamide at pH 7.8. Ala-boroPro thioxamide was pre-equilibrated at pH 2 and then the pH jumped to pH 7.8 by the addition of 0.6 M sodium phosphate buffer. $^1$H NMR spectra were recorded as a function of time at pH 7.8. Two well-resolved resonances representing the active (pH 2) and inactive (pH 7.8) forms of the drug were integrated and the integral as a function of time was fit to a single exponential. The same procedure was followed for inactivation of Ala-boroPro. The half-life for the reaction was 60 min for Ala-boroPro thioxamide and 30 min for Ala-boroPro.
Figure 8:
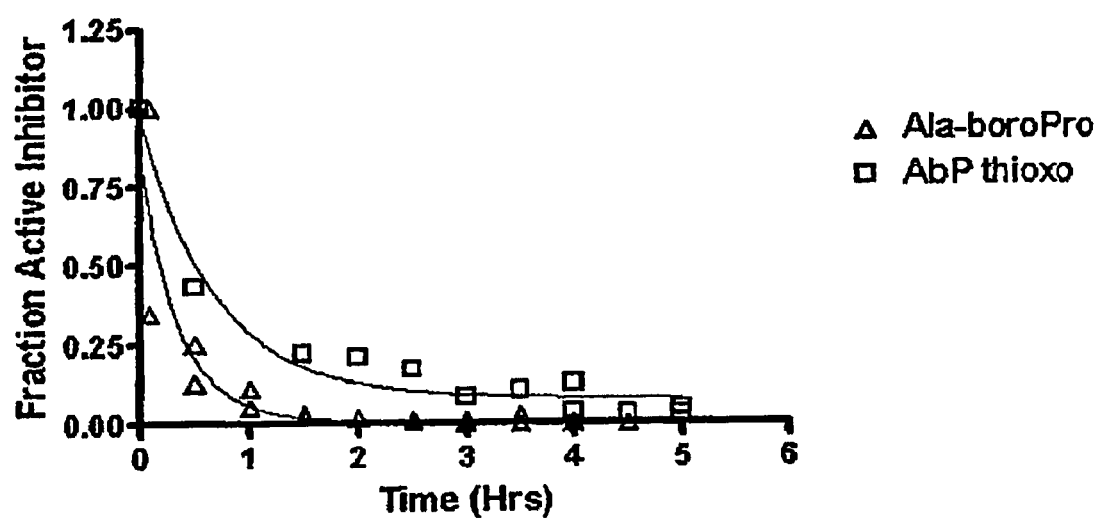
FIG. 8 depicts inactivation of Ala-boroPro Thioxamide at pH 7.8. Ala-boroPro and Ala-boroPro thioxamide were pre-equilibrated at pH 2 and then the pH jumped to pH 7.8 by the addition of 0.5 M sodium phosphate buffer. DPP IV inhibition was measured at various times after the pH jump and the $IC_{50}$ values were plotted as a function of time. From the $IC_{50}$ value, the mole fraction of active inhibitor was calculated assuming the pH 2 sample was 100% active. This value was fit to a single exponential. Half-lives obtained from these fits were 47 min for Ala-boroPro thioxamide and 24 min for Ala-boroPro.
Figure 9:
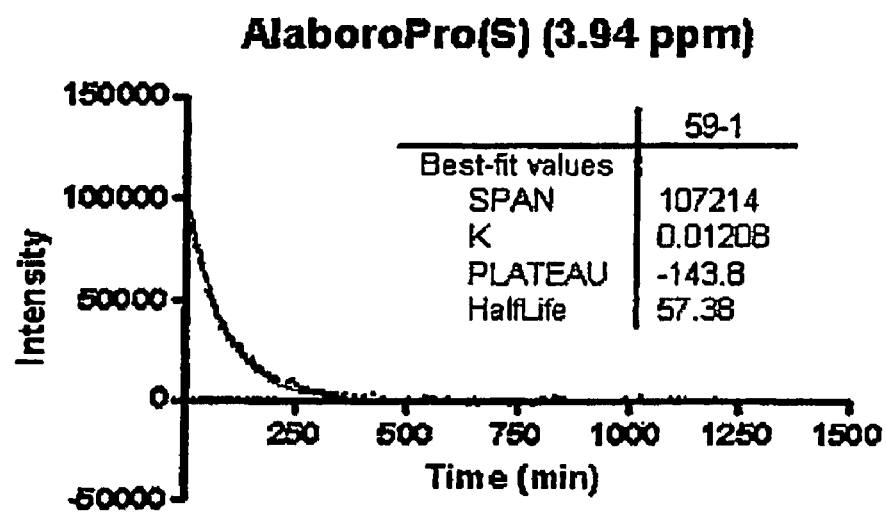
FIG. 9 depicts results of $^1$H NMR analysis of Ala-boroPro Thioxamide.
Figure 9:
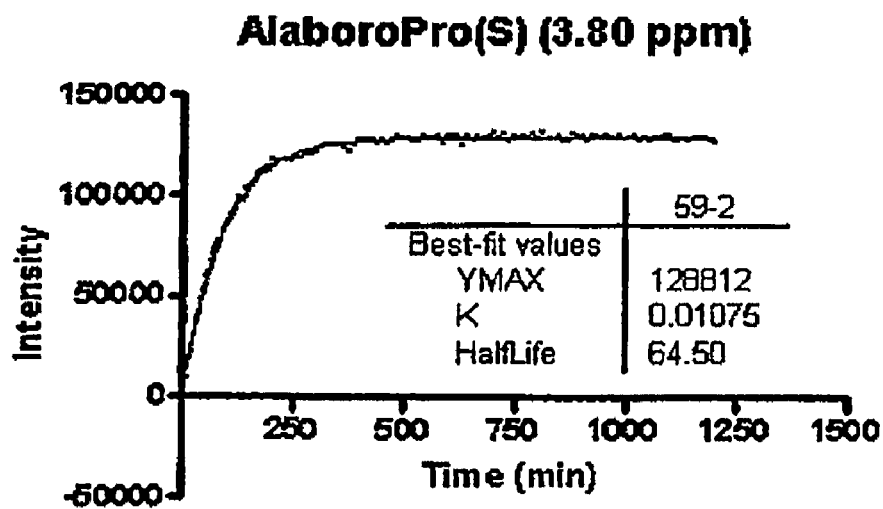
Figure 10:
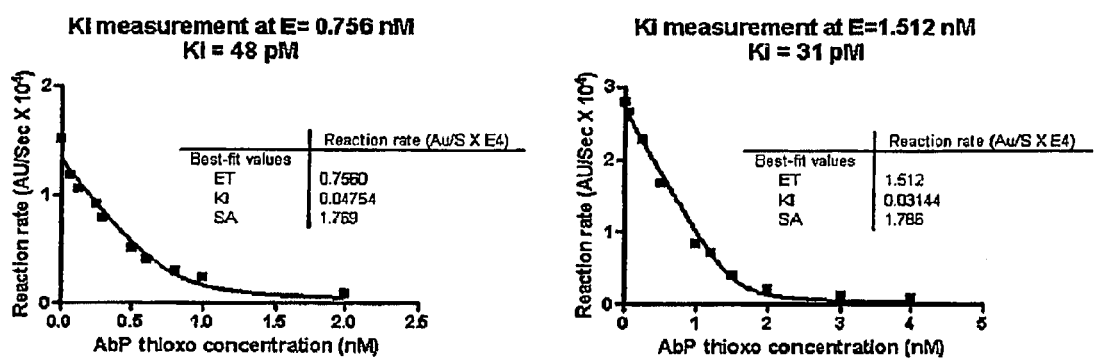
FIG. 10 depicts $K_i$ measurements of Ala-boroPro Thioxamide.
Figure 11:
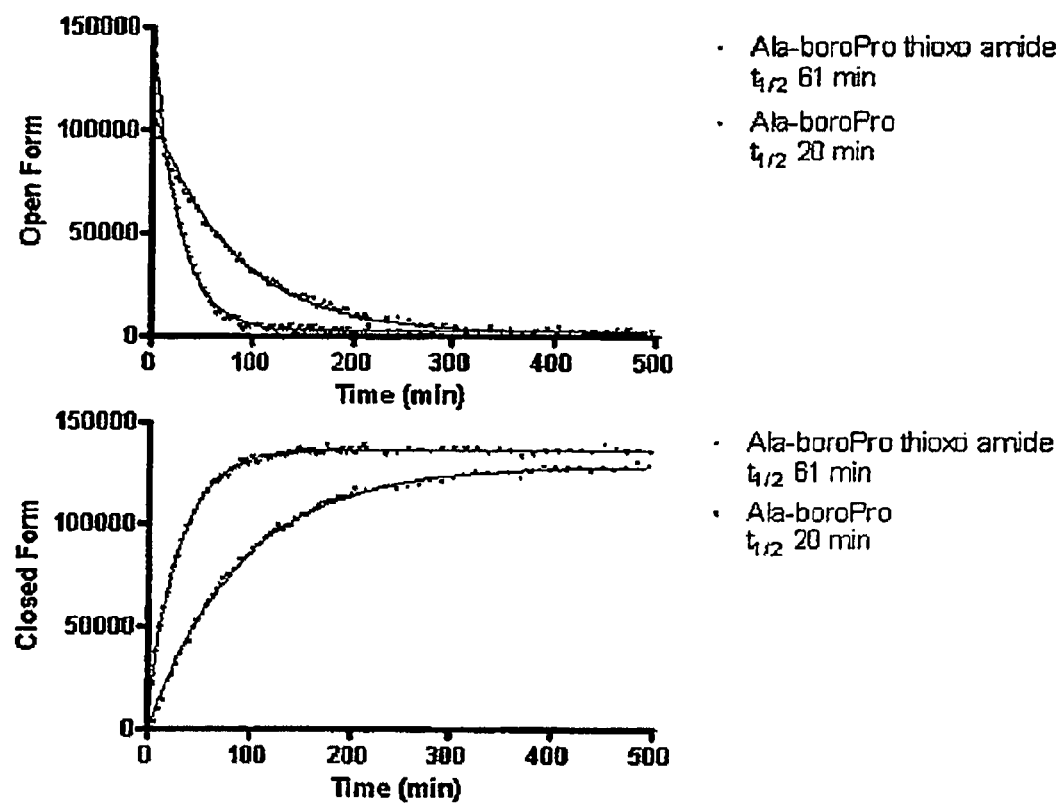
FIG. 11 depicts a comparison of deactivation rates for Ala-boroPro and Ala-boroPro Thioxamide.
Figure 12:
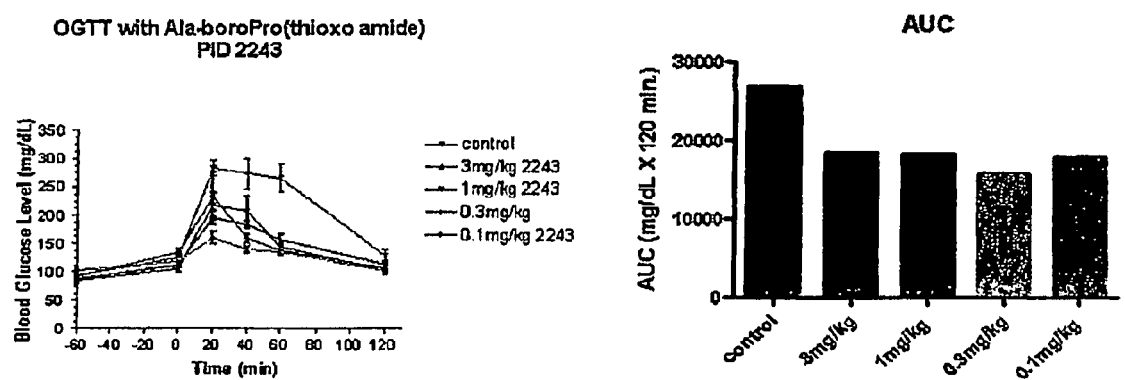
FIG. 12 depicts OGTT with Ala-boroPro Thioxamide.
Figure 13:
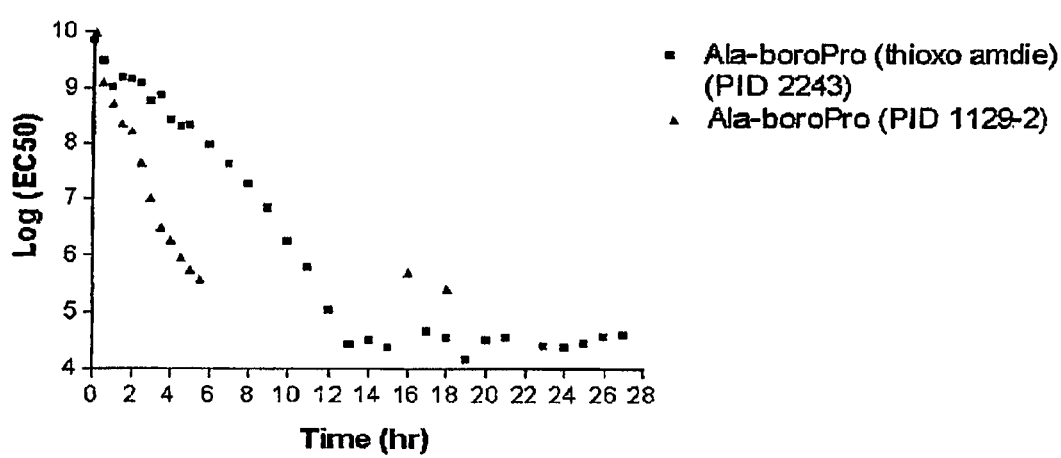
FIG. 13 depicts a comparison of Ala-boroPro and Ala-boroPro Thioxamide against DPPIV.
Figure 14:
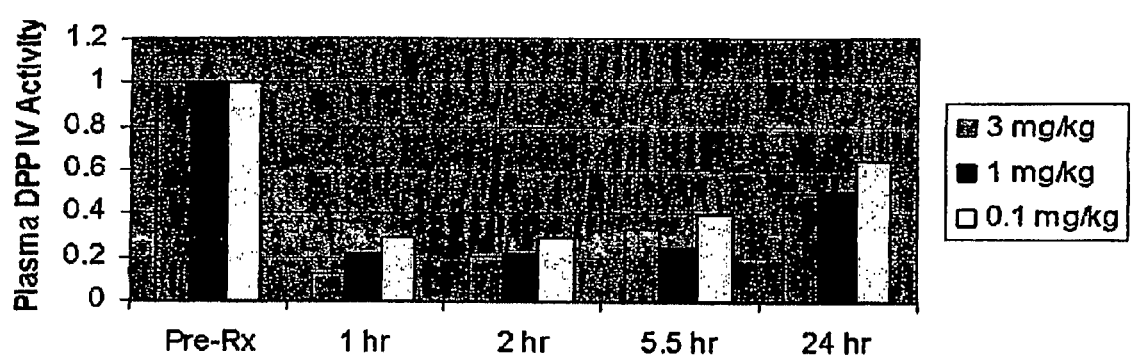
FIG. 14 depicts the activity of rat plasma DPP IV in the presence of Ala-boroPro Thioxamide.
Figure 15:
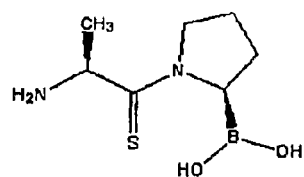
FIG. 15 depicts Ala-boroPro Thioxamide, NVP LAF327, and MK0431.
Figure 15:
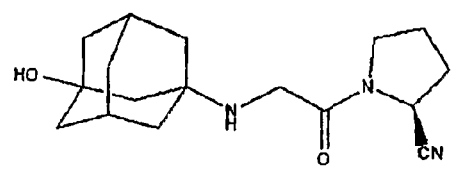
Figure 15:
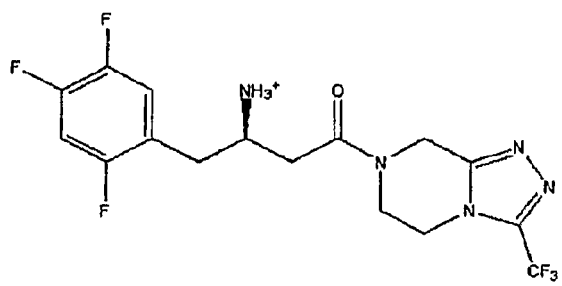
Figure 16:
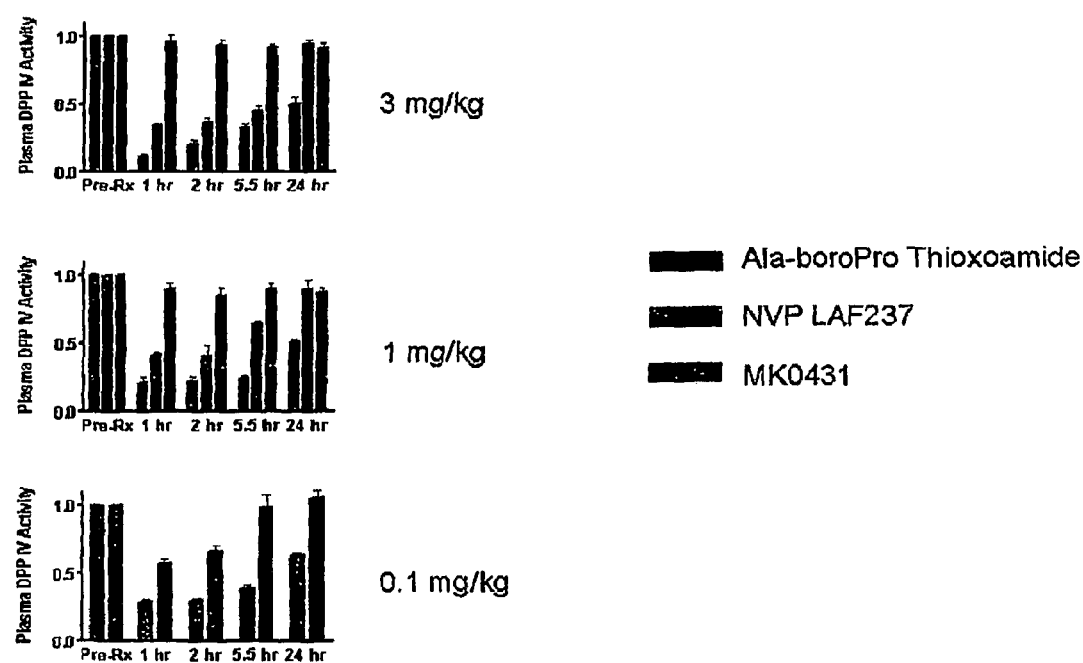
FIG. 16 depicts the results of Ala-boroPro Thioxamide, NVP LAF327, and MK0431 in an assay measuring inhibition of rat plasma DPP IV.
Figure 17:
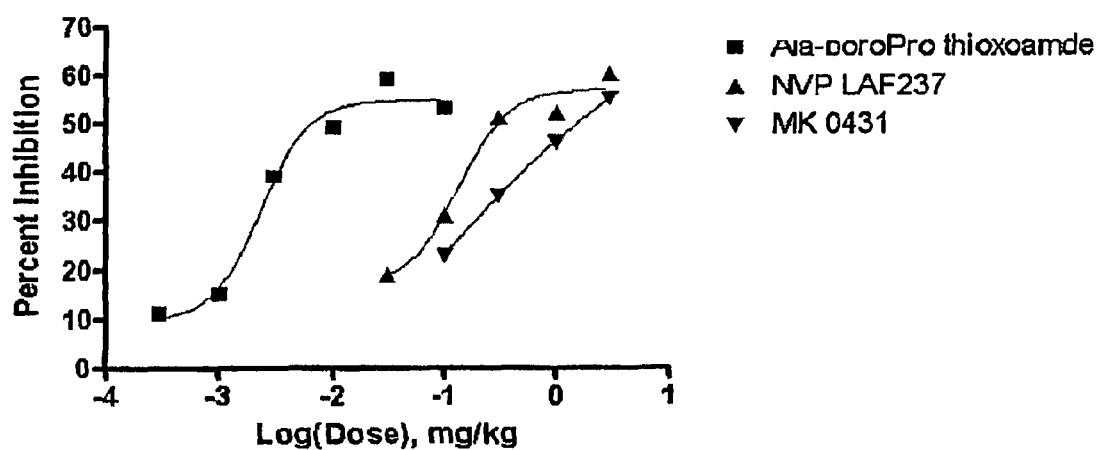
FIG. 17 depicts the results of Ala-boroPro Thioxamide, NVP LAF327, and MK0431 in an assay measuring inhibition of glucose excursion.
Figure 19:
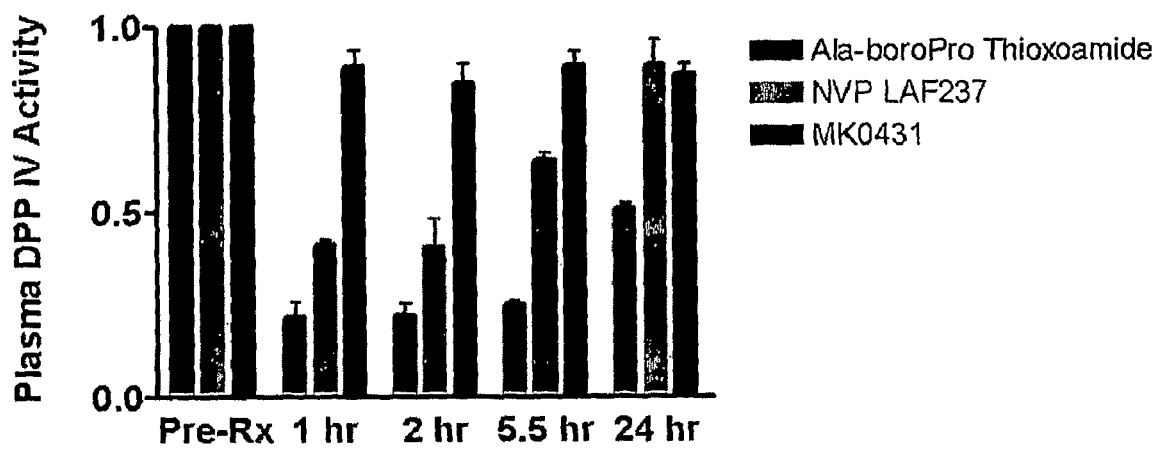
FIG. 19 depicts the results of Ala-boroPro Thioxamide, NVP LAF327, and MK0431 in an assay measuring rat plasma DPP IV activity following a single oral dose (1 mg/kg).
Figure 20:
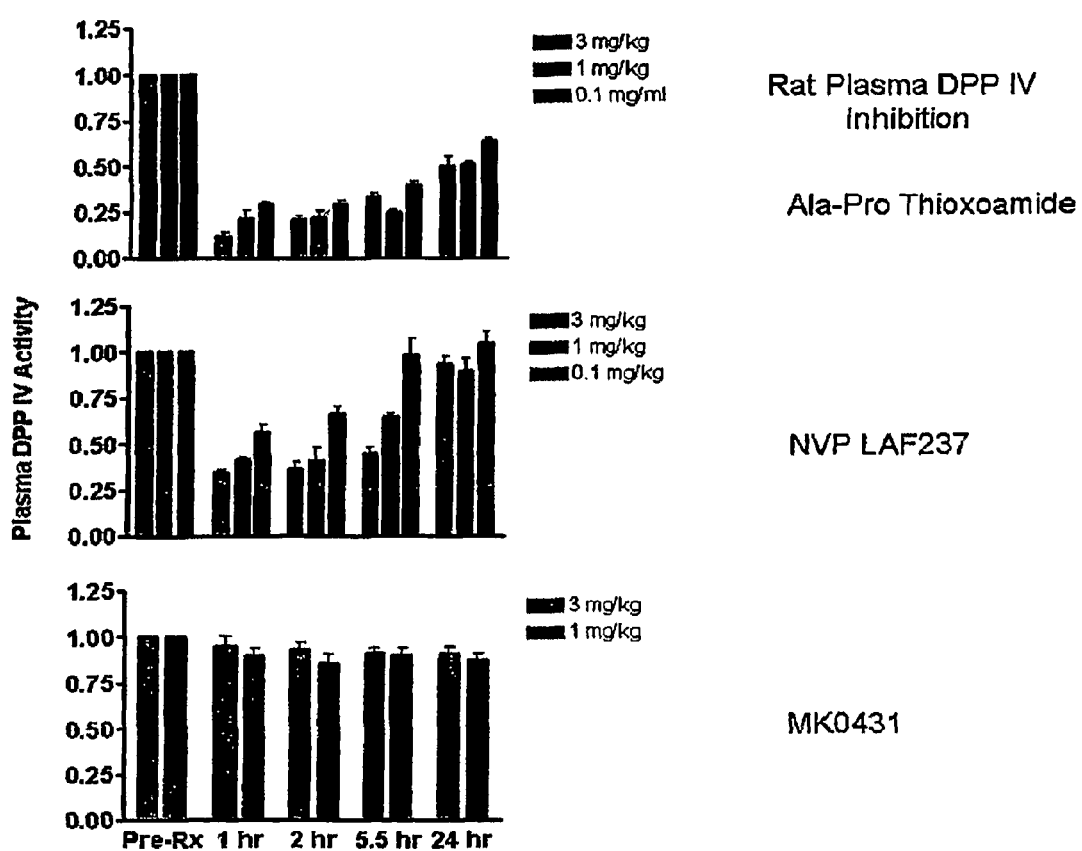
FIG. 20 depicts the results of Ala-boroPro Thioxamide, NVP LAF327, and MK0431 in an assay measuring inhibition of rat plasma DPP IV.
Figure 21:
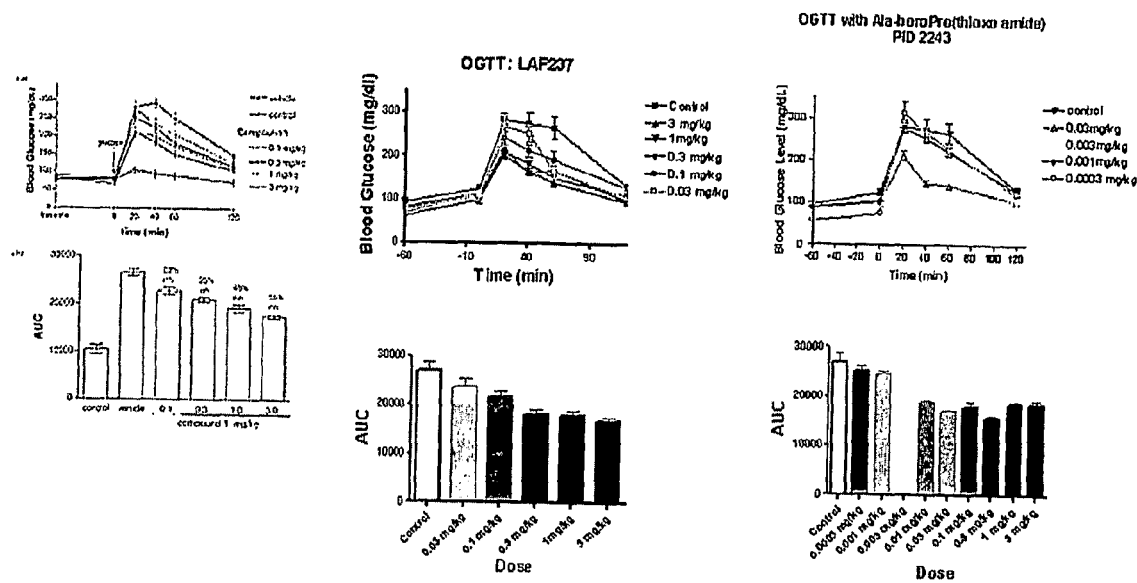
FIG. 21 depicts OGTT with Ala-boroPro Thioxamide and LAF327.
Figure 22:
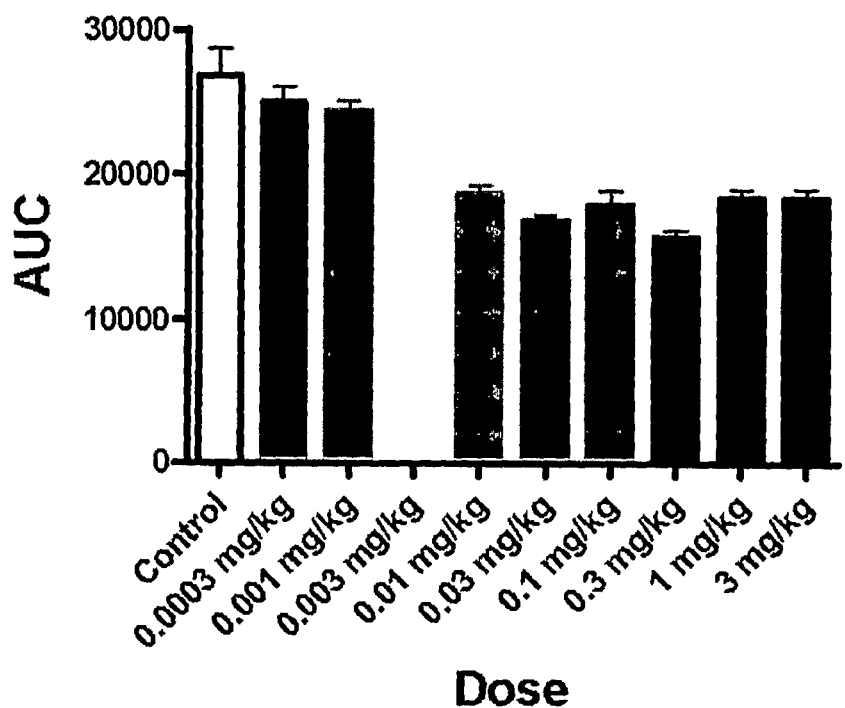
FIG. 22 depicts the results of Ala-boroPro Thioxamide in an oral glucose challenge assay in normal mice.
Figure 23:
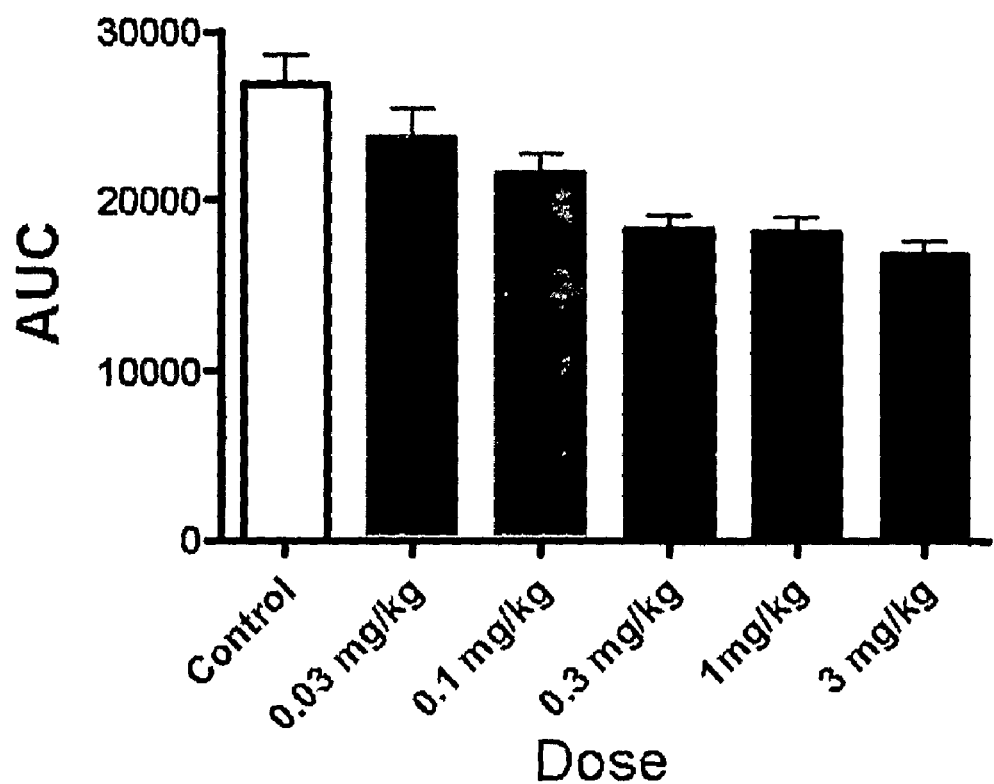
FIG. 23 depicts the results of NVP LAF327 in an oral glucose challenge assay in normal mice.
Figure 24:
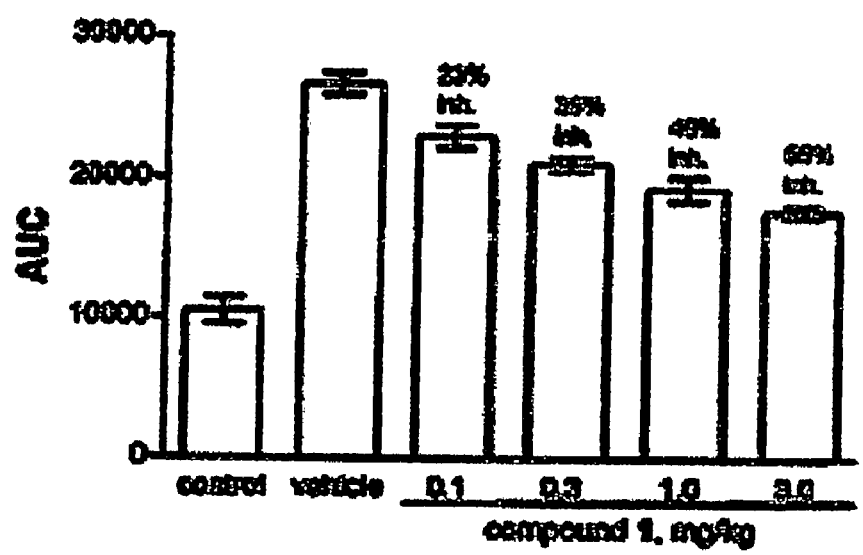
FIG. 24 depicts the results of MK0431 in an oral glucose challenge assay in normal mice. See Kim et al. *J. Med. Chem.* 2005, 48, 141-51.
Figure 25:
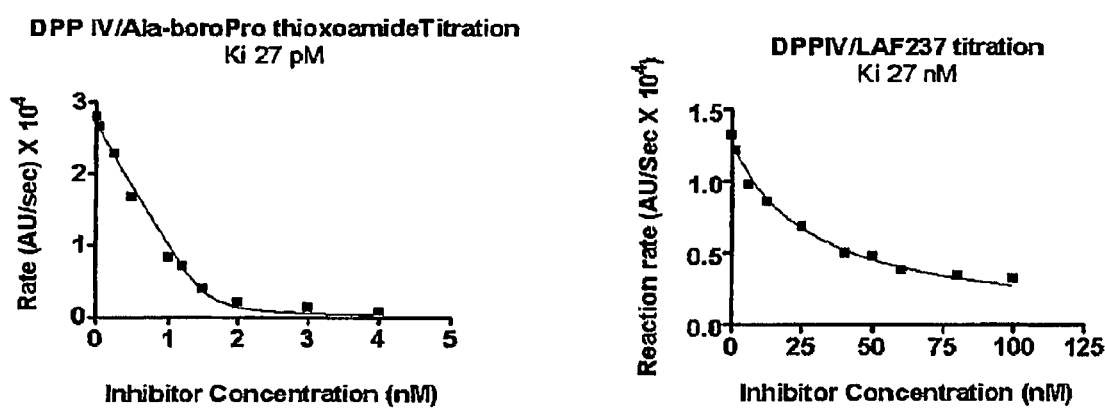
FIG. 25 depicts the $K_i$ of AbP thioamide and NVP LAF237.
Figure 26:
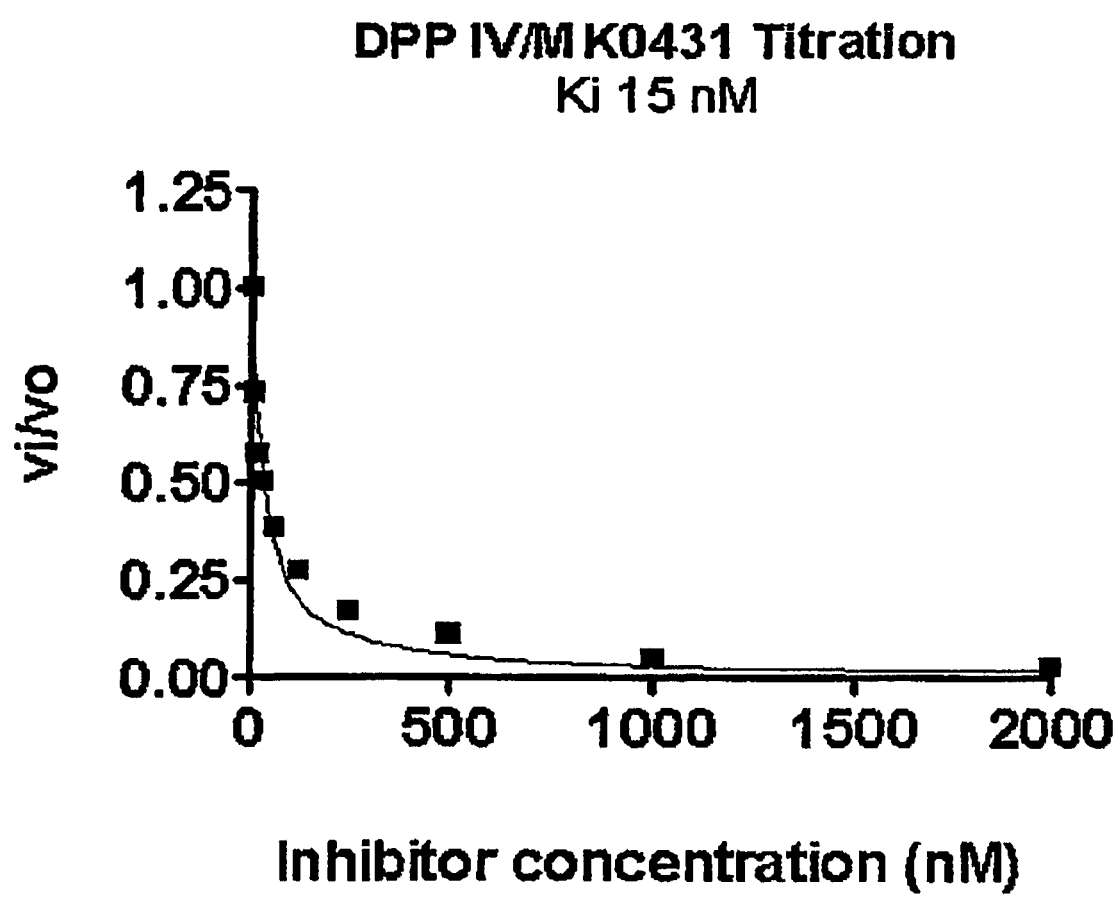
FIG. 26 depicts the $K_i$ for MK0431.
Figure 27:
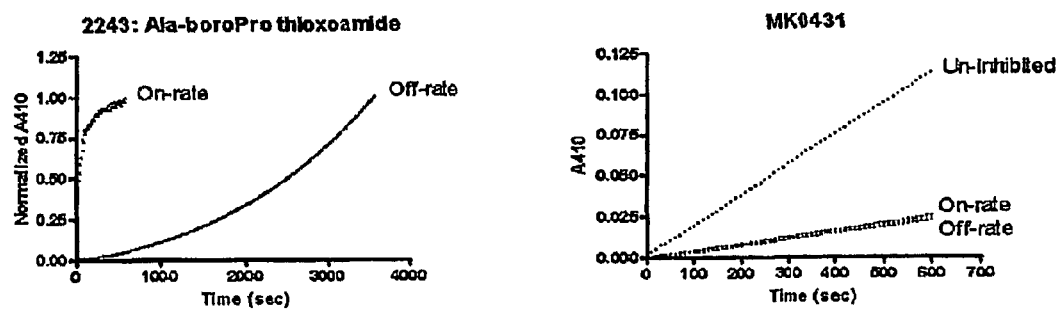
FIG. 27 depicts binding/release of MK0431 with DPP IV. On-rate: Simultaneously mix enzyme, substrate and inhibitor. Curve response represents slow binding. Off-rate: Pre-incubate enzyme with inhibitor at high concentration. Then, dilute mixture and add substrate. Curve reflects slow release of inhibitor following dilution.
Figure 28:
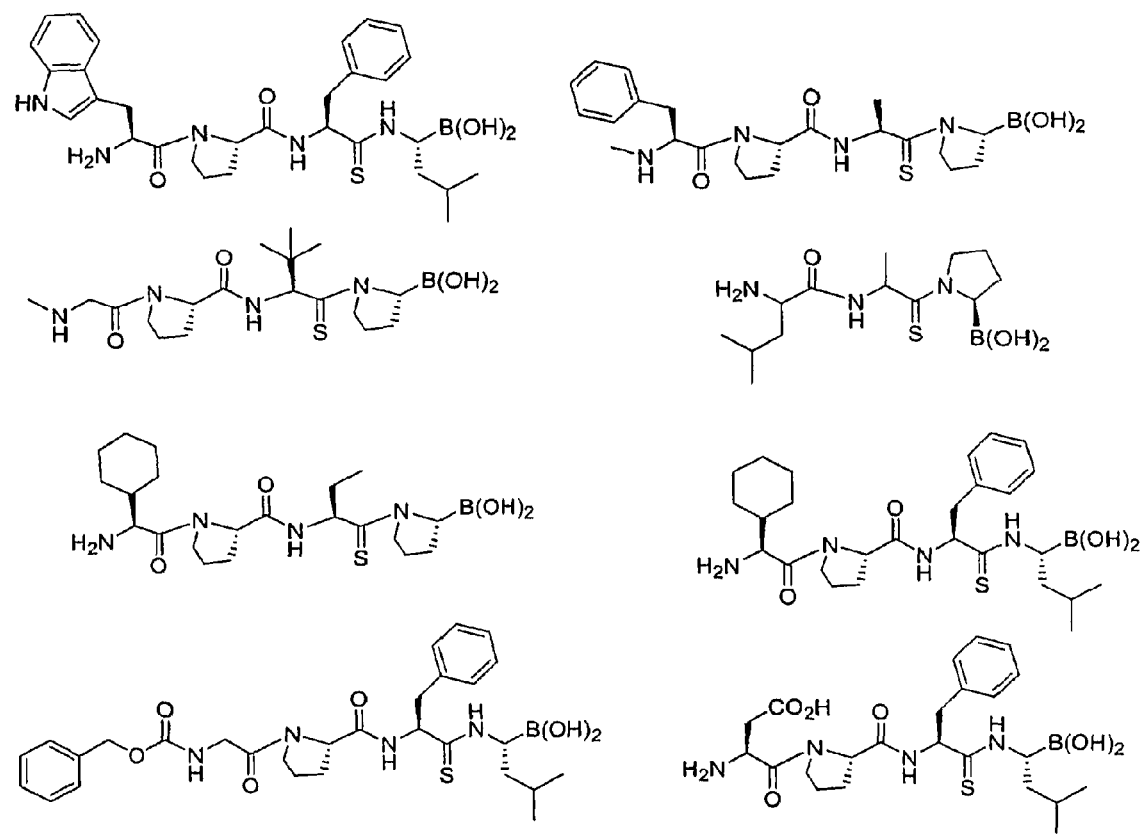
FIG. 28 depicts certain compounds of the invention.
Figure 29:
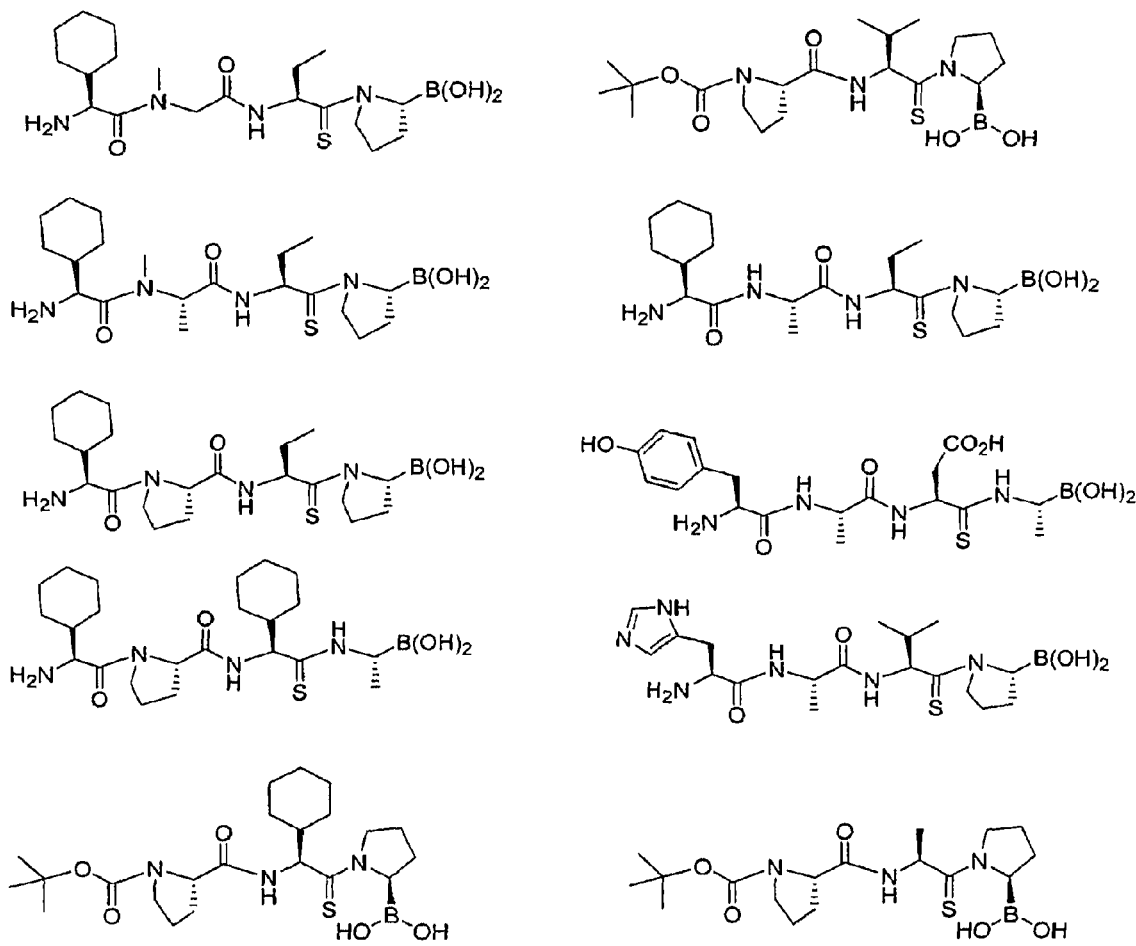
FIG. 29 depicts certain compounds of the invention.
Figure 30:
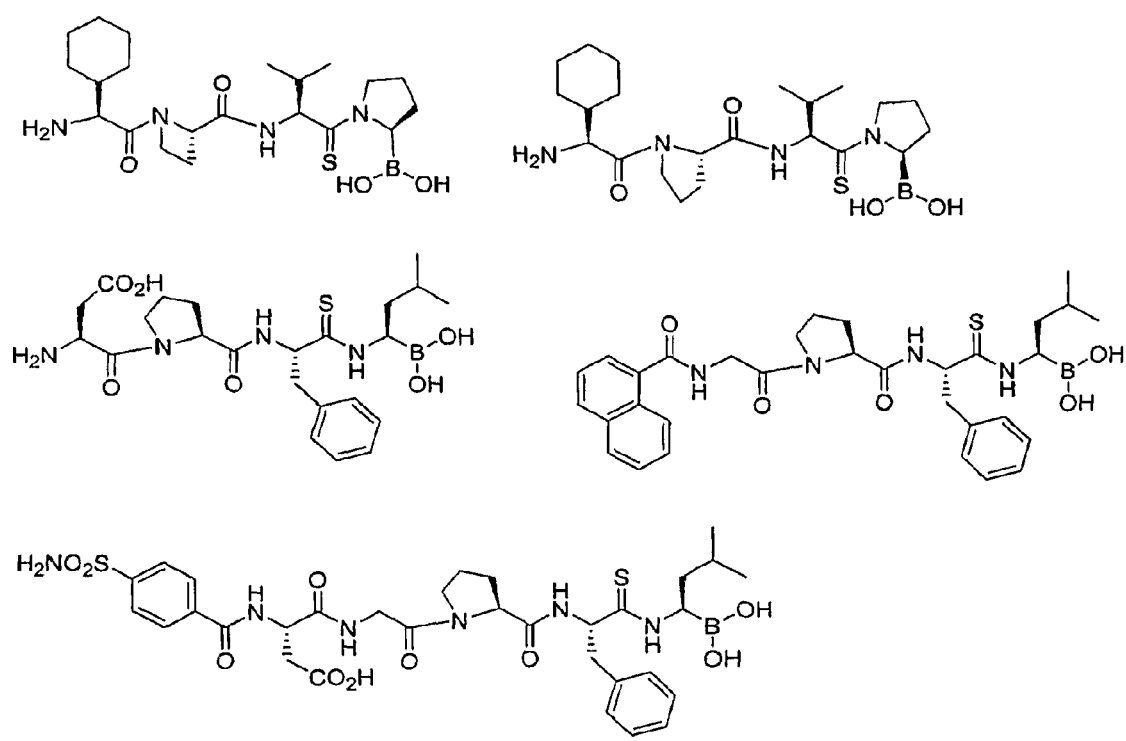
FIG. 30 depicts certain compounds of the invention.
Figure 31:
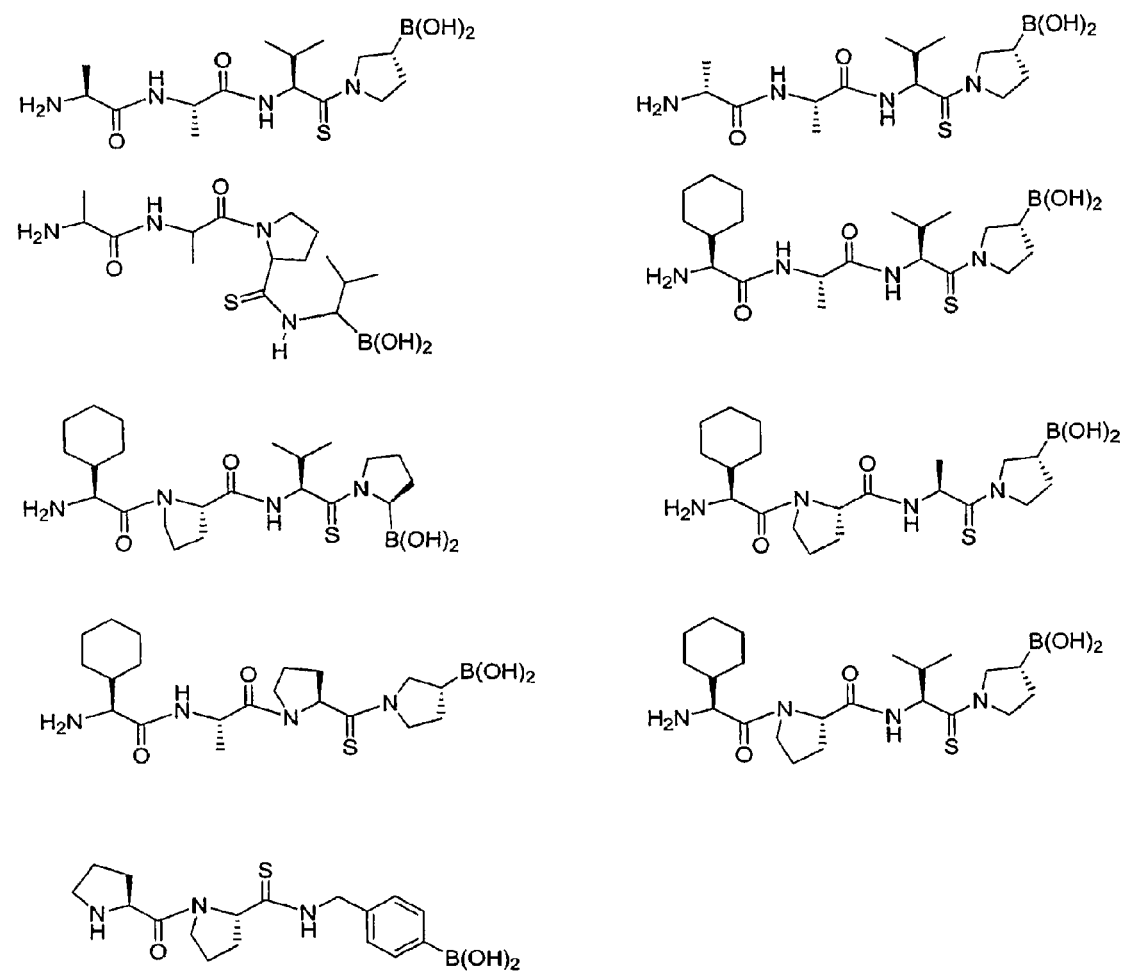
FIG. 31 depicts certain compounds of the invention.
Figure 32:
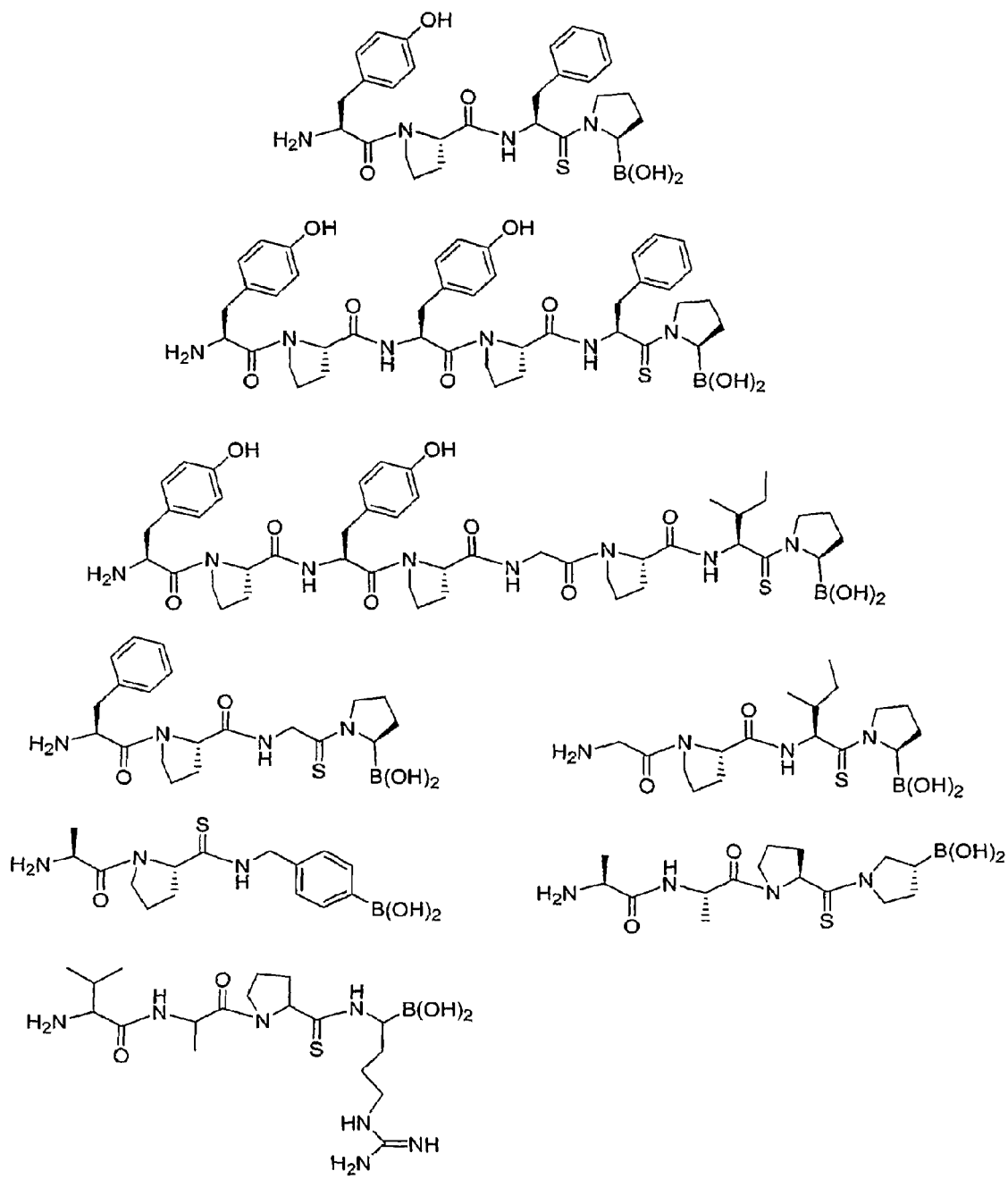
FIG. 32 depicts certain compounds of the invention.

The present invention provides protease inhibitors and methods of using protease inhibitors. The invention features inhibitors for a wide array of proteases. For example, the protease may be a post-proline cleaving enzyme (PPCE), such as dipeptidyl peptidase IV. The invention also provides compounds that inhibit proteasome activity. In certain instances, the protease inhibitor is a pro-soft inhibitor. A pro-soft inhibitor is an inactive agent that is activated, i.e., cleaved by an "activating protease," to release an active inhibitor moiety in proximity to a "target protease." The identity of the activating protease and target protease can be the same or different. After activation of the pro-soft inhibitor, the active inhibitor moiety undergoes self-inactivation by proto-deboronation. In certain instances, the invention features dipeptide boronic acid inhibitors of the type Xaa-boroPro, where Xaa refers to any natural or non-naturally occurring amino acid comprising a thioxamide moiety, and boroPro refers to the analog of proline in which the C-terminal carboxylate has been replaced by a boronyl group. Such compounds are potent inhibitors of dipeptidyl amino peptidase type IV (DPP IV). The dipeptide boronic acid compounds exist in open chain form under acidic conditions, but undergo proto-deboronation at neutral and basic conditions. The open chain form is active as an enzyme inhibitor; the compound formed from the proto-deboronation reaction is substantially inactive as an enzyme inhibitor. The pro-soft inhibitors of the present invention do not themselves undergo proto-deboronation and can be constructed such that they do not inhibit the selected target enzyme, or other enzymes to any significant extent, before being cleaved by the activating protease.

One of the features that makes the pro-soft inhibitor molecules of the current invention different from typical prodrugs is that the inhibitor moiety, after being generated in the active form near the target, undergoes inactivation over time, e.g., as it diffuses away from the target enzyme, thereby reducing the possibility of deleterious side effects that may result from inhibition of enzymes occurring in other parts of the patient. This combination of being released in an active form in the vicinity of the target enzyme together with this "programmed" deactivation mechanism makes the molecules of the invention more specific, effective, and safer (i.e., having fewer side effects) than the inhibitor moiety used on its own.

Advantageous features for compounds of the present invention include: better therapeutic indices, owing in part to reduced toxicity and/or improved specificity for the targeted protease; better oral availability; increased shelf-life; and/or increased duration of action (such as single oral dosage formulations which are effective for more than 4 hours, and even more preferably for more than 8, 12, or 16 hours). In certain instances, a compound of the invention has a $K_i$ for DPIV inhibition of about 50.0 nm or less, more preferably of about 10.0 nm or less, and even more preferably of about 1.0, 0.1, or even 0.01 nM or less. Indeed, inhibitors with $K_i$ values in the picomolar and even femtomolar range are contemplated.

Another advantageous feature for compounds of the present invention is that proto-deboronation irreversibly releases innocuous boric acid. The $LD_{50}$ of boric acid is approximately equal to that of common table salt. Accordingly, long-term chronic therapy with the compounds of the present invention is expected to yield an improved safety profile (fewer side effects).

The compounds of the present invention can be used as part of treatments for a variety of disorders/conditions, such as those which are mediated by DPIV. For instance, the compounds can be used to up-regulate GIP and GLP-1 activities, e.g., by increasing the half-life of those hormones, as part of a treatment for regulating glucose levels and/or metabolism, e.g., to reduce insulin resistance, treat hyperglycemia, hyperinsulinemia, obesity, hyperlipidemia, hyperlipoproteinemia (such as chylomicrons, VLDL and LDL), and to regulate body fat and more generally lipid stores, and, more generally, for the improvement of metabolism disorders, especially those associated with diabetes, obesity and/or atherosclerosis.

Certain of the subject compounds have extended duration. Accordingly, in certain certain embodiments, the compound is selected, and the amount of compound formulated, to provide a dosage which inhibits serum PPCE (e.g., DPIV) levels by at least 50% for at least 4 hours after a single dose, and even more preferably for at least 8 hours or even 12 or 16 hours after a single dose.

For instance, in certain embodiments the method involves administration of a DPIV inhibitor, preferably at a predetermined time(s) during a 24-hour period, in an amount effective to improve one or more aberrant indices associated with glucose metabolism disorders (e.g., glucose intolerance, insulin resistance, hyperglycemia, hyperinsulinemia, and Type I and II diabetes).

In other embodiments, the method involves administration of a DPIV inhibitor in an amount effective to improve aberrant indices associated with obesity. Fat cells release the hormone leptin, which travels in the bloodstream to the brain and, through leptin receptors there, stimulates production of GLP-1. GLP-1, in turn, produces the sensation of being full. The leading theory is that the fat cells of most obese people probably produce enough leptin, but leptin may not be able to properly engage the leptin receptors in the brain, and so does not stimulate production of GLP-1. There is accordingly a great deal of research towards utilizing preparations of GLP-1 as an appetite suppressant. The subject method provides a means for increasing the half-life of both endogenous and ectopically added GLP-1 in the treatment of disorders associated with obesity.

In a more general sense, the present invention provides methods and compositions for altering the pharmacokinetics of a variety of different polypeptide hormones by inhibiting the proteolysis of one or more peptide hormones by DPIV or some other proteolytic activity. Post-secretory metabolism is an important element in the overall homeostasis of regulatory peptides, and the other enzymes involved in these processes may be suitable targets for pharmacological intervention by the subject method. For example, the subject method can be used to increase the half-life of other proglucagon-derived peptides, such as glicentin (corresponding to PG 1-69), oxyntomodulin (PG 33-69), glicentin-related pancreatic polypeptide (GRPP, PG 1-30), intervening peptide-2 (IP-2, PG 111-122amide), and glucagon-like peptide-2 (GLP-2, PG 126-158).

GLP-2, for example, has been identified as a factor responsible for inducing proliferation of intestinal epithelium. See, for example, Drucker et al. *Proc. Natl. Acad. Sci. USA* 1996, 93, 7911. The subject method can be used as part of a regimen for treating injury, inflammation or resection of intestinal tissue, e.g., where enhanced growth and repair of the intestinal mucosal epithelial is desired, such as in the treatment of Crohn's disease or Inflammatory Bowel Disease (IBD).

DPIV has also been implicated in the metabolism and inactivation of growth hormone-releasing factor (GHRF). GHRF is a member of the family of homologous peptides that includes glucagon, secretin, vasoactive intestinal peptide (VIP), peptide histidine isoleucine (PHI), pituitary adenylate cyclase activating peptide (PACAP), gastric inhibitory peptide (GIP), and helodermin (Kubiak et al. *Peptide Res.* 1994, 7, 153). GHRF is secreted by the hypothalamus, and stimulates the release of growth hormone (GH) from the anterior pituitary. Thus, the subject method can be used to improve clinical therapy for certain growth hormone deficient children, and in clinical therapy of adults to improve nutrition and to alter body composition (muscle vs. fat). The subject method can also be used in veterinary practice, for example, to develop higher yield milk production and higher yield, leaner livestock.

Likewise, the DPIV inhibitors of the subject invention can be used to alter the plasma half-life of secretin, VIP, PHI, PACAP, GIP, and/or helodermin. Additionally, the subject method can be used to alter the pharmacokinetics of Peptide YY and neuropeptide Y, both members of the pancreatic polypeptide family, as DPIV has been implicated in the processing of those peptides in a manner which alters receptor selectivity.

In other embodiments, the compounds can be used to stimulate hematopoiesis. In still other embodiments, the compounds can be used to inhibit growth or vascularization of transformed cells/tissues, e.g., to inhibit cell proliferation such as that associated with tumor growth and metastasis, and for inhibiting angiogenesis in an abnormal proliferative cell mass. In yet other embodiments, the compounds can be used to reduce immunological responses, e.g., as an immunosuppressant.

In yet other examples, the DPIV inhibitors according to the present invention can be used to treat CNS maladies such as strokes, tumors, ischemia, Parkinson's disease, memory loss, hearing loss, vision loss, migraines, brain injury, spinal cord injury, Alzheimer's disease, and amyotrophic lateral sclerosis (which has a CNS component). Additionally, the DPIV inhibitors can be used to treat disorders having a more peripheral nature, including multiple sclerosis and diabetic neuropathy.

Another aspect of the present invention relates to pharmaceutical compositions of the subject post-proline cleaving enzyme inhibitors, particularly DPIV inhibitors, and their uses in treating and/or preventing disorders which can be improved by altering the homeostasis of peptide hormones. In a certain embodiment, the compounds have hypoglycemic and antidiabetic activities, and can be used in the treatment of disorders marked by aberrant glucose metabolism (including storage). In particular embodiments, the compositions of the subject methods are useful as insulinotropic agents, or to potentiate the insulinotropic effects of such molecules as GLP-1. In this regard, certain embodiments of the present compositions can be useful for the treatment and/or prophylaxis of a variety of disorders, including one or more of: hyperlipidemia, hyperglycemia, obesity, glucose tolerance insufficiency, insulin resistance, and diabetic complications.

In certain instances, the compounds of the subject method are small molecules, e.g., with molecular weights less than 7500 amu, preferably less than 5000 amu, and even more preferably less than 2000 or even less than 1000 amu. In certain embodiments, the compounds are orally active.

In certain instances, the compounds of the invention are used on combination with one or more pharmaceutical agents. A large number of pharmaceutical agents are known in the art and are amenable for use in the pharmaceutical compositions of the invention. The term "pharmaceutical agent" includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Non-limiting examples of broad categories of useful pharmaceutical agents include the following therapeutic categories: anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, and prodrugs.

More specifically, non-limiting examples of useful pharmaceutical agents include the following therapeutic categories: analgesics, such as nonsteroidal anti-inflammatory drugs, opiate agonists and salicylates; antihistamines, such as $H_1$-blockers and $H_2$-blockers; anti-infective agents, such as anthelmintics, antianaerobics, antibiotics, aminoglycoside antibiotics, antifungal antibiotics, cephalosporin antibiotics, macrolide antibiotics, miscellaneous beta-lactam antibiotics, penicillin antibiotics, quinolone antibiotics, sulfonamide antibiotics, tetracycline antibiotics, antimycobacterials, anti-tuberculosis antimycobacterials, antiprotozoals, antimalarial antiprotozoals, antiviral agents, anti-retroviral agents, scabicides, and urinary anti-infectives; antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor para-sympathomimetics, sympatholytics, alpha-blocker sympatholytics, beta-blocker sympatholytics, sympathomimetics, and adrenergic agonist sympathomimetics; cardiovascular agents, such as antianginals, beta-blocker antianginals, calcium-channel blocker antianginals, nitrate antianginals, antiarrhythmics, cardiac glycoside antiarrhythmics, class I antiarrhythmics, class II antiarrhythmics, class III antiarrhythmics, class IV antiarrhythmics, antihypertensive agents, alpha-blocker antihypertensives, angiotensin-converting enzyme inhibitor (ACE inhibitor) antihypertensives, beta-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, HMG-CoA reductase inhibitor antilipemics, inotropes, cardiac glycoside inotropes, and thrombolytic agents; dermatological agents, such as antihistamines, anti-inflammatory agents, corticosteroid anti-inflammatory agents, antipruritics/local anesthetics, topical anti-infectives, antifungal topical anti-infectives, antiviral topical anti-infectives, and topical antineoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, $H_2$-blocker anti-ulcer agents, cholelitholytic agents, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, anti-androgens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immuno-suppressive anti-inflammatory agents, nonsteroidal anti-inflammatory drugs (NSAIDs), salicylate anti-inflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, such as anti-glaucoma agents, beta-blocker anti-glaucoma agents, miotic anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs (NSAIDs); psychotropic agents, such as antidepressants, heterocyclic antidepressants, monoamine oxidase inhibitors (MAOIs), selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti-inflammatory agents, and respiratory corticosteroid anti-inflammatory agents; toxicology agents, such as antidotes, heavy metal antagonists/chelating agents, substance abuse agents, deterrent substance abuse agents, and withdrawal substance abuse agents; minerals; and vitamins, such as vitamin A, vitamin B, vitamin C, vitamin D, vitamin E, and vitamin K.

Preferred classes of useful pharmaceutical agents from the above categories include: (1) nonsteroidal anti-inflammatory drugs (NSAIDs) analgesics, such as diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) $H_1$-blocker antihistamines, such as clemastine and terfenadine; (5) $H_2$-blocker antihistamines, such as cimetidine, famotidine, nizadine, and ranitidine; (6) anti-infective agents, such as mupirocin; (7) antianaerobic anti-infectives, such as chloramphenicol and clindamycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous beta-lactam antibiotic anti-infectives, such as aztreonam and imipenem; (11) penicillin antibiotic anti-infectives, such as nafcillin, oxacillin, penicillin G, and penicillin V; (12) quinolone antibiotic anti-infectives, such as ciprofloxacin and norfloxacin; (13) tetracycline antibiotic anti-infectives, such as doxycycline, minocycline, and tetracycline; (14) antituberculosis antimycobacterial anti-infectives such as isoniazid (INH), and rifampin; (15) antiprotozoal anti-infectives, such as atovaquone and dapsone; (16) antimalarial antiprotozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon alpha, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antimetabolite antineoplastic agents, such as fluorouracil (5-FU) and gemcitabine; (23) hormonal antineoplastics, such as goserelin, leuprolide, and tamoxifen; (24) natural antineoplastics, such as aldesleukin, interleukin-2, docetaxel, etoposide (VP-16), interferon alpha, paclitaxel, and tretinoin (ATRA); (25) antibiotic natural antineoplastics, such as bleomycin, dactinomycin, daunorubicin, doxorubicin, and mitomycin; (26) vinca alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) alpha-blocker sympatholytics, such as prazosin; (34) beta-blocker sympatholytics, such as atenolol; (35) adrenergic agonist sympathomimetics, such as albuterol and dobutamine; (36) cardiovascular agents, such as aspirin (ASA) (enteric coated ASA); (37) beta-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as digoxin; (41) class I antiarrhythmics, such as lidocaine, mexiletine, phenyloin, procainamide, and quinidine; (42) class II antiarrhythmics, such as atenolol, metoprolol, propranolol, and timolol; (43) class III antiarrhythmics, such as amiodarone; (44) class IV antiarrhythmics, such as diltiazem and verapamil; (45) alpha-blocker antihypertensives, such as prazosin; (46) angiotensin-converting enzyme inhibitor (ACE inhibitor) antihypertensives, such as captopril and enalapril; (47) beta.-blocker antihypertensives, such as atenolol, metoprolol, nadolol, and propanolol; (48) calcium-channel blocker antihypertensive agents, such as diltiazem and nifedipine; (49) central-acting adrenergic antihypertensives, such as clonidine and methyldopa; (50) diuretic antihypertensive agents, such as amiloride, furosemide, hydrochlorothiazide (HCTZ), and spironolactone; (51) peripheral vasodilator antihypertensives, such as hydralazine and minoxidil; (52) antilipemics, such as gemifibrozil and probucol; (53) bile acid sequestrant antilipemics, such as cholestyramine; (54) HMG-CoA reductase inhibitor antilipemics, such as lovastatin and pravastatin; (55) inotropes, such as amrinone, dobutamine, and dopamine; (56) cardiac glycoside inotropes, such as digoxin; (57) thrombolytic agents, such as alteplase (TPA), anistreplase, streptokinase, and urokinase; (58) dermatological agents, such as colchicine, isotretinoin, methotrexate, minoxidil, tretinoin (ATRA); (59) dermatological corticosteroid anti-inflammatory agents, such as betamethasone and dexamethasone; (60) antifungal topical anti-infectives, such as amphotericin B, clotrimazole, miconazole, and nystatin; (61) antiviral topical anti-infectives, such as acyclovir; (62) topical antineoplastics, such as fluorouracil (5-FU); (63) electrolytic and renal agents, such as lactulose; (64) loop diuretics, such as furosemide; (65) potassium-sparing diuretics, such as triamterene; (66) thiazide diuretics, such as hydro-chlorothiazide (HCTZ); (67) uricosuric agents, such as probenecid; (68) enzymes such as RNase and DNase; (69) thrombolytic enzymes, such as alteplase, anistreplase, streptokinase and urokinase; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) $H_2$-blocker anti-ulcer agents, such as cimetidine, famotidine, nizatidine, and ranitidine; (74) digestants, such as pancrelipase; (75) prokinetic agents, such as erythromycin; (76) opiate agonist intravenous anesthetics such as fentanyl; (77) hematopoietic antianemia agents, such as erythropoietin, filgrastim (G-CSF), and sargramostim (GM-CSF); (78) coagulation agents, such as antihemophilic factors 1-10 (AHF 1-10); (79) anticoagulants, such as warfarin; (80) thrombolytic enzyme coagulation agents, such as alteplase, anistreplase, streptokinase and urokinase; (81) hormones and hormone modifiers, such as bromocriptine; (82) abortifacients, such as methotrexate; (83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadotropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-1b and interferon gamma-1b; (93) immunoglobulins, such as immune globulin 1M, IMIG, IGIM and immune globulin IV, IVIG, IGIV; (94) amide local anesthetics, such as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs (NSAIDs), such as diclofenac, ibuprofen, ketoprofen, ketorlac, and naproxen; (99) skeletal muscle relaxants, such as baclofen, cyclobenzaprine, and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenyloin, and valproic acid; (103) barbiturate anticonvulsants, such as phenobarbital and primidone; (104) benzodiazepine anticonvulsants, such as clonazepam, diazepam, and lorazepam; (105) anti-parkinsonian agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) .beta.-blocker anti-glaucoma agents, such as timolol; (110) miotic anti-glaucoma agents, such as pilocarpine; (111) ophthalmic aminoglycoside antiinfectives, such as gentamicin, neomycin, and tobramycin; (112) ophthalmic quinolone anti-infectives, such as ciprofloxacin, norfloxacin, and ofloxacin; (113) ophthalmic corticosteroid anti-inflammatory agents, such as dexamethasone and prednisolone; (114) ophthalmic nonsteroidal anti-inflammatory drugs (NSAIDs), such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) antitussives, such as codeine; (119) bronchodilators, such as theophylline; (120) adrenergic agonist bronchodilators, such as albuterol; (121) respiratory corticosteroid anti-inflammatory agents, such as dexamethasone; (122) antidotes, such as flumazenil and naloxone; (123) heavy metal antagonists/chelating agents, such as penicillamine; (124) deterrent substance abuse agents, such as disulfuram, naltrexone, and nicotine; (125) withdrawal substance abuse agents, such as bromocriptine; (126) minerals, such as iron, calcium, and magnesium; (127) vitamin B compounds, such as cyanocobalamin (vitamin B12) and niacin (vitamin B3); (128) vitamin C compounds, such as ascorbic acid; and (129) vitamin D compounds, such as calcitriol.

In addition to the foregoing, the following less common drugs may also be used: chlorhexidine; estradiol cypionate in oil; estradiol valerate in oil; flurbiprofen; flurbiprofen sodium; ivermectin; levodopa; nafarelin; and somatropin. Further, the following drugs may also be used: recombinant beta-glucan; bovine immunoglobulin concentrate; bovine superoxide dismutase; the formulation comprising fluorouracil, epinephrine, and bovine collagen; recombinant hirudin (r-Hir), HIV-1 immunogen; human anti-TAC antibody; recombinant human growth hormone (r-hGH); recombinant human hemoglobin (r-Hb); recombinant human mecasermin (r-IGF-1); recombinant interferon beta-1a; lenograstim (G-CSF); olanzapine; recombinant thyroid stimulating hormone (r-TSH); and topotecan.

Further still, the following intravenous products may be used: acyclovir sodium; aldesleukin; atenolol; bleomycin sulfate, human calcitonin; salmon calcitonin; carboplatin; carmustine; dactinomycin, daunorubicin HCl; docetaxel; doxorubicin HCl; epoetin alpha; etoposide (VP-16); fluorouracil (5-FU); ganciclovir sodium; gentamicin sulfate; interferon alpha; leuprolide acetate; meperidine HCl; methadone HCl; methotrexate sodium; paclitaxel; ranitidine HCl; vinblastin sulfate; and zidovudine (AZT).

Further specific examples of useful pharmaceutical agents from the above categories include: (a) anti-neoplastics such as androgen inhibitors, antimetabolites, cytotoxic agents, and immunomodulators; (b) anti-tussives such as dextromethorphan, dextromethorphan hydrobromide, noscapine, carbetapentane citrate, and chlorphedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate and morphine; (f) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines, and other bioactive peptidic compounds, such as interleukins 1-18 including mutants and analogues, RNase, DNase, luteinizing hormone releasing hormone (LHRH) and analogues, gonadotropin releasing hormone (GnRH), transforming growth factor-beta (TGF-beta), fibroblast growth factor (FGF), tumor necrosis factor-alpha & beta (TNF-alpha & beta), nerve growth factor (NGF), growth hormone releasing factor (GHRF), epidermal growth factor (EGF), fibroblast growth factor homologous factor (FGFHF), hepatocyte growth factor (HGF), insulin growth factor (IGF), invasion inhibiting factor-2 (IIF-2), bone morphogenetic proteins 1-7 (BMP 1-7), somatostatin, thymosin-alpha-1, gamma-globulin, superoxide dismutase (SOD), complement factors, hGH, tPA, calcitonin, ANF, EPO and insulin; and (n) anti-infective agents such as antifungals, anti-virals, antiseptics and antibiotics.

Alternatively, the pharmaceutical agent may be a radiosensitizer, such as metoclopramide, sensamide or neusensamide (manufactured by Oxigene); profiromycin (made by Vion); RSR13 (made by Allos); Thymitaq (made by Agouron), etanidazole or lobenguane (manufactured by Nycomed); gadolinium texaphrin (made by Pharmacyclics); BuDR/Broxine (made by NeoPharm); IPDR (made by Sparta); CR2412 (made by Cell Therapeutic); LIX (made by Terrapin); or the like. Preferably, the biologically active substance is selected from the group consisting of the group consisting of peptides, poly-peptides, proteins, amino acids, polysaccharides, growth factors, hormones, anti-angiogenesis factors, interferons or cytokines, and pro-drugs. In a particularly certain embodiment, the biologically active substance is a therapeutic drug or pro-drug, most preferably a drug selected from the group consisting of chemotherapeutic agents and other anti-neoplastics such as paclitaxel, antibiotics, antivirals, antifungals, anti-inflammatories, and anticoagulants.

The biologically active substances are used in amounts that are therapeutically effective. While the effective amount of a biologically active substance will depend on the particular material being used, amounts of the biologically active substance from about 1% to about 65% may be desirable. Lesser amounts may be used to achieve efficacious levels of treatment for certain biologically active substances.

Definitions

The term "high affinity" as used herein means strong binding affinity between molecules with a dissociation constant $K_D$ of no greater than 1 μM. In a preferred case, the $K_D$ is less than 100 nM, 10 nM, 1 nM, 100 pM, or even 10 pM or less. In a most certain embodiment, the two molecules can be covalently linked ($K_D$ is essentially 0).

The term "boro-Ala" refers to the analog of alanine in which the carboxylate group (COOH) is replaced with a boronyl group (B(OH)$_2$). Likewise, the term "boro-Pro" refers to the analog of proline in which the carboxylate group (COOH) is replaced with a boronyl group (B(OH)$_2$). More generally, the term "boro-Xaa", where Xaa is an amino acid residue, refers to the analog of an amino acid in which the carboxylate group (COOH) is replaced with a boronyl group (B(OH)$_2$).

The term "Ala-boroPro" refers to

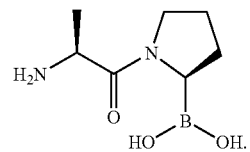

The term "Ala-boroPro thioxo amide" refers to

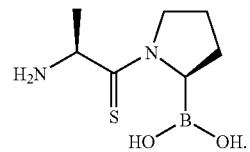

The term "Pro-boroPro" refers to

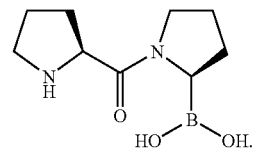

The term "thioxam" used in association with chemical nomenclature refers to a compound wherein at least one amide group has been replaced by at least one thioxamide group. For example Pro(thioxam) refers to a proline residue wherein the amide group has been replaced by a thioxamide group.

A "patient" or "subject" to be treated by the subject method can mean either a human or non-human subject. Non-human subjects include farm animals (e.g., cows, horses, pigs, sheep) and companion animals (e.g., cats, dogs).

The term "$ED_{50}$" means the dose of a drug that, in 50% of patients, will provide a clinically relevant improvement or change in a physiological measurement, such as glucose responsiveness, increase in hematocrit, decrease in tumor volume, etc.

The term "$IC_{50}$" means the dose of a drug that inhibits a biological activity by 50%, e.g., the amount of compound required to inhibit at least 50% of DPIV (or other PPCE) activity in vivo.

A compound is said to have an "insulinotropic activity" if it is able to stimulate, or cause the stimulation of, the synthesis or expression of the hormone insulin.

The term "interact" as used herein is meant to include all interactions (e.g., biochemical, chemical, or biophysical interactions) between molecules, such as protein-protein, protein-nucleic acid, nucleic acid-nucleic acid, protein-small molecule, nucleic acid-small molecule, or small molecule-small molecule interactions.

The term "$LD_{50}$" means the dose of a drug that is lethal in 50% of test subjects.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, delays the onset of, or otherwise inhibits symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "therapeutic index" refers to the therapeutic index of a drug defined as $LD_{50}/ED_{50}$.

A "therapeutically effective amount" of a compound, e.g., such as a DPIV inhibitor of the present invention, with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

A "single oral dosage formulation" is a dosage which provides an amount of drug to produce a serum concentration at least as great as the $EC_{50}$ for that drug, but less than the $LD_{50}$. Another measure for a single oral dosage formulation is that it provides an amount of drug necessary to produce a serum concentration at least as great as the $IC_{50}$ for that drug, but less than the $LD_{50}$. By either measure, a single oral dosage formulation is preferably an amount of drug which produces a serum concentration at least 10% less than the $LD_{50}$, and even more preferably at least 50%, 75%, or even 90% less than the drug's the $LD_{50}$.

An aliphatic chain comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6, or 7 carbons in the ring structure.

Unless the number of carbons is otherwise specified, "lower alkyl," as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In certain embodiments, a substituent designated herein as alkyl is a lower alkyl.

The term "alkylthio" refers to an alkyl group, as defined above, having a sulfur moiety attached thereto. In certain embodiments, the "alkylthio" moiety is represented by one of —(S)-alkyl, —(S)-alkenyl, —(S)-alkynyl, and —(S)—($CH_2$)$_m$—$R^1$, wherein m and $R^1$ are defined below. Representative alkylthio groups include methylthio, ethylthio, and the like.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located anywherein the moiety and can have either the (Z) or the (E) configuration about the double bond(s).

"Alkynyl" refers to hydrocarbyl moieties of the scope of alkenyl, but having one or more triple bonds in the moiety.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls, or alkynyls.

The terms "alkoxyl" or "alkoxy" as used herein refers to an alkyl group, as defined below, having an oxygen moiety attached thereto. Representative alkoxyl groups include methoxy, ethoxy, propoxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R^1$, where m and $R_1$ are described below.

The terms "amine" and "amino" are art-recognized and refer to both unsubstituted and substituted amines, e.g., a moiety that can be represented by the formulae:

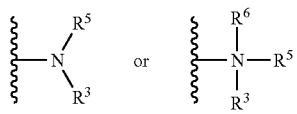

wherein $R^3$, $R^5$ and $R^6$ each independently represent a hydrogen, an alkyl, an alkenyl, —$(CH_2)_m$—$R^1$, or $R^3$ and $R^5$ taken together with the N atom to which they are attached complete a heterocycle having from 4 to 8 atoms in the ring structure; $R^1$ represents an alkenyl, aryl, cycloalkyl, a cycloalkenyl, a heterocyclyl, or a polycyclyl; and m is zero or an integer in the range of 1 to 8. In certain embodiments, only one of $R^3$ or $R^5$ can be a carbonyl, e.g., $R^3$, $R^5$, and the nitrogen together do not form an imide. In even more certain embodiments, $R^3$ and $R^5$ (and optionally $R^6$) each independently represent a hydrogen, an alkyl, an alkenyl, or —$(CH_2)_m$—R. Thus, the term "alkylamine" as used herein means an amine group, as defined above, having a substituted or unsubstituted alkyl attached thereto, i.e., at least one of $R_3$ and $R_5$ is an alkyl group. In certain embodiments, an amino group or an alkylamine is basic, meaning it has a conjugate acid with a $pK_a$>7.00, i.e., the protonated forms of these functional groups have $pK_a$s relative to water above about 7.00.

The term "aryl" as used herein includes 5-, 6-, and 7-membered substituted or unsubstituted single-ring aromatic groups in which each atom of the ring is carbon (i.e., carbocyclic aryl) or where one or more atoms are heteroatoms (i.e., heteroaryl). The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carbocyclic aryl groups include benzene, naphthalene, phenanthrene, phenol, aniline, and the like. Heteroaryl groups include substituted or unsubstituted aromatic 5- to 7-membered ring structures, more preferably 5- to 6-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like.

The term "carbonyl" is art-recognized and includes such moieties as can be represented by the formula:

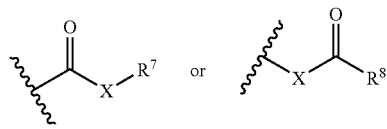

wherein X is a bond or represents an oxygen or a sulfur, and $R^7$ represents a hydrogen, an alkyl, an alkenyl, —$(CH_2)_m$—$R^1$ or a pharmaceutically acceptable salt, $R^8$ represents a hydrogen, an alkyl, an alkenyl or —$(CH_2)_m$—$R^1$, where m and $R^1$ are as defined above. Where X is an oxygen and $R^7$ or $R^8$ is not hydrogen, the formula represents an "ester." Where X is an oxygen, and $R^7$ is as defined above, the moiety is referred to herein as a carboxyl group, and particularly when $R^7$ is a hydrogen, the formula represents a "carboxylic acid". Where X is an oxygen, and $R^8$ is a hydrogen, the formula represents a "formate." In general, where the oxygen atom of the above formula is replaced by a sulfur, the formula represents a "thiocarbonyl" group. Where X is a sulfur and $R^7$ or $R^8$ is not hydrogen, the formula represents a "thioester" group. Where X is a sulfur and $R^7$ is a hydrogen, the formula represents a "thiocarboxylic acid" group. Where X is a sulfur and $R^8$ is a hydrogen, the formula represents a "thioformate" group. On the other hand, where X is a bond, and $R^7$ is not hydrogen, the above formula represents a "ketone" group. Where X is a bond, and $R^7$ is a hydrogen, the above formula represents an "aldehyde" group.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —$CF_3$, —CN, and the like.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "hydrocarbyl" refers to a monovalent hydrocarbon moiety comprised of carbon chains or rings of up to 26 carbon atoms to which hydrogen atoms are attached. The term includes alkyl, cycloalkyl, alkenyl, alkynyl, and aryl groups, groups which have a mixture of saturated and unsaturated bonds, carbocyclic rings, and includes combinations of such groups. It may refer to straight chain, branched-chain, cyclic structures, or combinations thereof.

The term "hydrocarbylene" refers to a divalent hydrocarbyl moiety. Representative examples include alkylene, phenylene, or cyclohexylene. Preferably, the hydrocarbylene chain is fully saturated and/or has a chain of 1 to 10 carbon atoms.

As used herein, the term "nitro" means $-NO_2$; the term "halogen" designates $-F$, $-Cl$, $-Br$, or $-I$; the term "sulfhydryl" means $-SH$; the term "hydroxyl" means $-OH$; the term "sulfonyl" means $-SO_2-$; the term "azido" means $-N_3$; the term "cyano" means $-CN$; the term "isocyanato" means $-NCO$; the term "thiocyanato" means $-SCN$; the term "isothiocyanato" means $-NCS$; and the term "cyanato" means $-OCN$.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the formula:

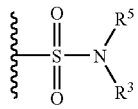

in which $R^3$ and $R^5$ are as defined above.

The term "sulfate" is art recognized and includes a moiety that can be represented by the formula:

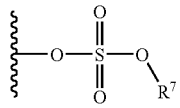

in which $R^7$ is as defined above.

The term "sulfonamide" is art recognized and includes a moiety that can be represented by the formula:

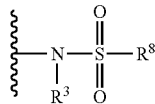

in which $R^3$ and $R^8$ are as defined above.

The term "sulfonate" is art-recognized and includes a moiety that can be represented by the formula:

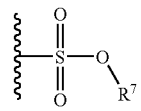

in which $R^7$ is an electron pair, hydrogen, alkyl, cycloalkyl, or aryl.

The terms "sulfoxido" or "sulfinyl", as used herein, refers to a moiety that can be represented by the formula:

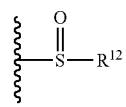

in which $R^{12}$ is selected from the group consisting of the group consisting of hydrogen, alkyl, alkenyl, alkynyl, cycloalkyl, heterocyclyl, aralkyl, or aryl.

The term "thioxamide," as used herein, refers to a moiety that can be represented by the formula:

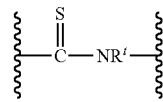

in which $R^t$ is selected from the group consisting of the group consisting of hydrogen, alkyl, cycloalkyl, aralkyl, or aryl, preferably hydrogen or alkyl. Moreover, "thioxamide-derived" compounds or "thioxamide analogs" refer to compounds in which one or more amide groups have been replaced by one or more corresponding thioxamide groups. Thioxamides are also referred to in the art as "thioamides."

As used herein, the definition of each expression, e.g., alkyl, m, n, etc., when it occurs more than once in any structure, is intended to be independent of its definition elsewherein the same structure.

"Biohydrolyzable amide" refers to an amide moiety that is cleaved (e.g., to form a hydroxyl and a carboxylic acid) under physiological conditions. Physiological conditions include the acidic and basic environments of the digestive tract (e.g., stomach, intestines, etc.), enzymatic cleavage, metabolism, and other biological processes, and preferably refer to physiological conditions in a vertebrate, such as a mammal.

"Biohydrolyzable ester" refers to an ester moiety that is cleaved (e.g., to form a hydroxyl and a carboxylic acid) under physiological conditions. Physiological conditions include the acidic and basic environments of the digestive tract (e.g., stomach, intestines, etc.), enzymatic cleavage, metabolism, and other biological processes, and preferably refer to physiological conditions in a vertebrate, such as a mammal.

"Biohydrolyzable imide" refers to an imide moiety that is cleaved (e.g., to form a hydroxyl and a carboxylic acid) under physiological conditions. Physiological conditions include the acidic and basic environments of the digestive tract (e.g., stomach, intestines, etc.), enzymatic cleavage, metabolism, and other biological processes, and preferably refer to physiological conditions in a vertebrate, such as a mammal.

The terms "amino acid residue" and "peptide residue" mean an amino acid or peptide molecule without the $-OH$ of its carboxyl group. In general the abbreviations used herein for designating the amino acids and the protective groups are based on recommendations of the IUPAC-IUB Commission on Biochemical Nomenclature (see *Biochemistry* 1972, 11, 1726-1732). For instance, Met, Ile, Leu, Ala, and Gly represent "residues" of methionine, isoleucine, leucine, alanine, and glycine, respectively. Residue means a moiety derived from the corresponding α-amino acid by eliminating the OH portion of the carboxyl group and the H portion of the α-amino group. The term "amino acid side chain" is that part of an amino acid exclusive of the —CH(NH$_2$)COOH portion, as defined by K. D. Kopple, *Peptides and Amino Acids*; Benjamin: New York, 1966; pp. 2 and 33; examples of such side chains of the common amino acids are —CH$_2$CH$_2$SCH$_3$ (the side chain of methionine), —CH$_2$(CH$_3$)—CH$_2$CH$_3$ (the side chain of isoleucine), —CH$_2$CH(CH$_3$)$_2$ (the side chain of leucine) or H-(the side chain of glycine).

For the most part, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan, and those amino acids and amino acid analogs which have been identified as constituents of peptidylglycan bacterial cell walls.

The term amino acid residue further includes analogs, derivatives and congeners of any specific amino acid referred to herein, as well as C-terminal or N-terminal protected amino acid derivatives (e.g., modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated, the amino acid or residue can have the configuration (D), (L), or (DL). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) and (L) stereoisomers.

The phrase "protecting group" as used herein means substituents which protect the reactive functional group from undesirable chemical reactions. Examples of such protecting groups include esters of carboxylic acids and boronic acids, ethers of alcohols, and acetals and ketals of aldehydes and ketones. For instance, the phrase "N-terminal protecting group" or "amino-protecting group" as used herein refers to various amino-protecting groups which can be employed to protect the N-terminus of an amino acid or peptide against undesirable reactions during synthetic procedures. Examples of suitable groups include acyl protecting groups such as, to illustrate, formyl, dansyl, acetyl, benzoyl, trifluoroacetyl, succinyl, and methoxysuccinyl; aromatic urethane protecting groups as, for example, benzyloxycarbonyl (Cbz); and aliphatic urethane protecting groups such as t-butoxycarbonyl (Boc) or 9-Fluorenylmethoxycarbonyl (Fmoc).

As noted above, certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. In certain embodiments where a particular enantiomer is preferred, a compound of the present invention is enriched to have >60%, >70%, >80%, >90%, >95%, or even greater than 98% or 99% of the preferred enantiomer, as opposed to a racemate where the two enantiomers each are present to the extent of 50%.

If, for instance, a particular enantiomer of a compound of the present invention is desired, it may be prepared by asymmetric synthesis or by derivation with a chiral auxiliary, where the resulting diastereomeric mixture is separated and the auxiliary group cleaved to provide the pure desired enantiomer. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomer.

For purposes of this invention, the chemical elements are identified in accordance with the Periodic Table of the Elements, CAS version, *Handbook of Chemistry and Physics*, 67th ed., 1986-87, inside cover.

A compound is said to have an "insulinotropic activity" if it is able to stimulate, or cause the stimulation of, the synthesis or expression of the hormone insulin.

The term "amino-terminal protecting group" as used herein, refers to terminal amino protecting groups that are typically employed in organic synthesis, especially peptide synthesis. Any of the known categories of protecting groups can be employed, including acyl protecting groups, such as acetyl, and benzoyl; aromatic urethane protecting groups, such as benzyloxycarbonyl; and aliphatic urethane protecting groups, such as tert-butoxycarbonyl. See, for example, Gross and Mienhoffer, Eds., *The Peptides*, Academic Press: New York, 1981; Vol. 3, 3-88; and Green, T. W.; Wuts, P. G. M., *Protective Groups in Organic Synthesis*, 2nd ed, Wiley: New York, 1991. Preferred protecting groups include aryl-, aralkyl-, heteroaryl- and heteroarylalkyl-carbonyl and sulfonyl moieties.

The term "amino acid analog" refers to a compound structurally similar to a naturally occurring amino acid wherein either the C-terminal carboxy group, the N-terminal amino group or side-chain functional group has been chemically modified. For example, aspartic acid-(beta-methyl ester) is an amino acid analog of aspartic acid; N-ethylglycine is an amino acid analog of glycine; or alanine carboxamide is an amino acid analog of alanine.

The terms "gastrointestinal inflammation," "inflammatory bowel disease," and "inflammation of the gastrointestinal tract" are used interchangeably herein to mean inflammation of any portion of the gastrointestinal tract, from the esophagus to the sigmoid flexure or the termination of the colon in the rectum. The inflammation can be acute, but, generally, the composition of this invention is used to treat Crohnic conditions.

A "single oral dosage formulation" is a dosage which provides an amount of drug to produce a serum concentration at least as great as the $EC_{50}$ for that drug, but less than the $LD_{50}$. Another measure for a single oral dosage formulation is that it provides an amount of drug necessary to produce a serum concentration at least as great as the $IC_{50}$ for that drug, but less than the $LD_{50}$. By either measure, a single oral dosage formulation is preferably an amount of drug which produces a serum concentration at least 10% less than the $LD_{50}$, and even more preferably at least 50%, 75%, or even 90% less than the $LD_{50}$.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the inhibitors of the present invention from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) RingeRs solution; (19) ethyl alcohol; (20) phosphate buffer solutions; and (21) other non-toxic compatible substances employed in pharmaceutical formulations.

The term "pharmaceutically acceptable salts" in these instances refers to the relatively non-toxic, inorganic and organic base addition salts of compounds of the present invention.

The term "pharmaceutically functional derivative" refers to any pharmaceutically acceptable derivative of an inhibitor of the present invention, for example, an ester or an amide, which upon administration to a mammal is capable of providing (directly or indirectly) the inhibitor. Such derivatives are recognizable to those skilled in the art, without undue experimentation. Nevertheless reference is made to the teaching of *Burger's Medicinal Chemistry and Drug Discovery*, 5th ed., Vol 1.

As used herein the term "physiological conditions" refers to temperature, pH, ionic strength, viscosity, and like biochemical parameters which are compatible with a viable organism, and/or which typically exist intracellularly in a viable mammalian cell The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The term "shelf-life" typically refers to the time period for which the performance characteristics of an inhibitor remain at peak. As used herein, the term "$T_{90}$" refers to the amount of time it takes for a preparation of the subject inhibitor to degrade to the point that it has 90% of the activity of the starting sample, e.g., a diminishment of 10%. Likewise, the term "$T_{50}$" refers to the amount of time it takes for a preparation of the subject inhibitor to degrade to the point that it has 50% of the activity of the starting sample, e.g., a diminishment of 50%. The shelf-life, whether reported as $T_{90}$ or $T_{50}$, for a given pharmaceutical preparation of an inhibitor is the measured for the preparation as it is packaged for use by a healthcare provider or patient.

As used herein the term "substantially soluble" refers to inhibitors which can be dissolved in inhalant propeller mixture to form a substantially clear to hazy solution which will not separate into layers or form a precipitate when left unagitated for a minimum of 24 hours at room temperature.

By "transdermal patch" is meant a system capable of delivery of a drug to a patient via the skin, or any suitable external surface, including mucosal membranes, such as those found inside the mouth. Such delivery systems generally comprise a flexible backing, an adhesive and a drug retaining matrix, the backing protecting the adhesive and matrix and the adhesive holding the whole on the skin of the patient. On contact with the skin, the drug-retaining matrix delivers inhibitor to the skin, the drug then passing through the skin into the patient's system.

The term "quaternizing agent" refers to a chemical compound which converts a nitrogen atom with fewer than four substituents to a positively charged nitrogen atom with four substituents. Examples of "quaternizing agents" include lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others.

The term "therapeutic index" refers to the therapeutic index of a drug defined as $LD_{50}/ED_{50}$.

A "therapeutically effective amount" of a compound, e.g., such as a dipeptidyl peptidase inhibitor of the present invention, with respect to the subject method of treatment, refers to an amount of the compound(s) in a preparation which, when administered as part of a desired dosage regimen (to a mammal, preferably a human) brings alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

A "therapeutically effective daily dosage" of a compound, e.g., such as an inhibitor of the present invention, with respect to the subject method of treatment, refers to an amount of the compound(s) in a preparation which, when administered as part of a desired daily dosage regimen (to a mammal, preferably a human) brings alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

It will be understood that all generic structures recited herein, with respect to appropriate combinations of substituents, are intended to cover those embodiments permitted by valency and stability.

Exemplary Embodiments (i). Compounds

Useful compounds will be described below using various formulae. In each case, the variables in the formula are defined specifically for each individual formulae. A definition of a variable for one formula should not be used to vary a definition provided for another formula, although a variable that has not been defined for one formula may be interpreted by analogy with a definition elsewhere for a similar formula.

Embodiment A

A representative class of compounds for use in the method of the present invention are represented by formula I:

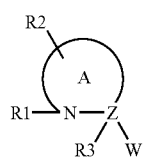

(I)

wherein

A represents a 4-8 membered heterocycle including the N and the Cα carbon;

Z represents C or N;

W represents a functional group which reacts with an active site residue of the targeted protease, as for example, —CN, —CH=NR$_5$,

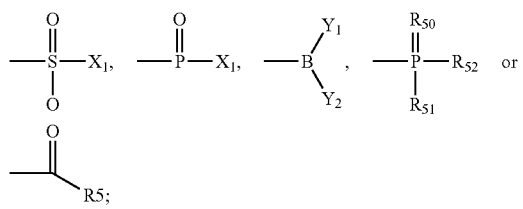

$R_1$ represents a C-terminally linked amino acid residue or amino acid analog, or a C-terminally linked peptide or peptide analog, or

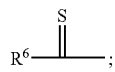

wherein the bond between $R_1$ and N is a thioxamide bond;

$R_2$ is absent or represents one or more substitutions to the ring A, each of which is independently a halogen, lower alkyl, lower alkenyl, lower alkynyl, carbonyl (such as a carboxyl, ester, formate, or ketone), thiocarbonyl (such as a thioester, thioacetate, or thioformate), amino, acylamino, amido, nitro, sulfate, sulfonate, sulfonamido, —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_7$, —(CH$_2$)$_m$—SH, —(CH$_2$)$_m$—S-lower alkyl, —(CH$_2$)$_m$—S-lower alkenyl, or —(CH$_2$)$_n$—S—(CH$_2$)$_m$—R$_7$, azido, cyano, isocyanato, thiocyanato, isothiocyanato, cyanato,

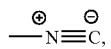

or

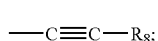

when Z is N, R$_3$ is absent;

when Z is C, R$_3$ represents hydrogen or a halogen, lower alkyl, lower alkenyl, lower alkynyl, carbonyl, thiocarbonyl, amino, acylamino, amido, nitro, sulfate, sulfonate, a sulfonamido, —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_7$, —(CH$_2$)$_m$—SH, —(CH$_2$)$_m$—S-lower alkyl, —(CH$_2$)$_m$—S-lower alkenyl, or —(CH$_2$)$_n$—S—(CH$_2$)$_m$—R$_7$, azido, cyano, isocyanato, thiocyanato, isothiocyanato, cyanato,

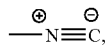

or

R$_5$ represents H, alkyl, alkenyl, alkynyl, —C(X$_1$)(X$_2$)X$_3$, —(CH$_2$)$_m$—R$_7$, —(CH$_2$)$_n$—OH, —(CH$_2$)$_n$—O-alkyl, —(CH$_2$)$_n$—O-alkenyl, —(CH$_2$)$_n$—O-alkynyl, —(CH$_2$)$_n$—O—(CH$_2$)$_m$—R$_7$, —(CH$_2$)$_n$—SH, —(CH$_2$)$_n$—S-alkyl, —(CH$_2$)$_n$—S-alkenyl, —(CH$_2$)$_n$—S-alkynyl, —(CH$_2$)$_n$—S—(CH$_2$)$_m$—R$_7$, —C(O)C(O)NH$_2$, or —C(O)C(O)OR'$_7$;

R$_6$ represents hydrogen, a halogen, alkyl, alkenyl, alkynyl, aryl, —(CH$_2$)$_m$—R$_7$, —(CH$_2$)$_m$—OH, —(CH$_2$)$_m$—O-alkyl, —(CH$_2$)$_m$—O-alkenyl, —(CH$_2$)$_m$—O-alkynyl, —(CH$_2$)$_m$—O—(CH$_2$)$_m$—R$_7$, —(CH$_2$)$_m$—SH, —(CH$_2$)$_m$—S-alkyl, —(CH$_2$)$_m$—S-alkenyl, —(CH$_2$)$_m$—S-alkynyl, —(CH$_2$)$_m$—S—(CH$_2$)$_m$—R$_7$,

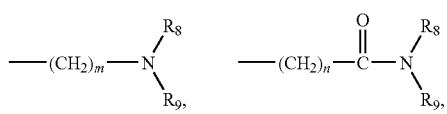

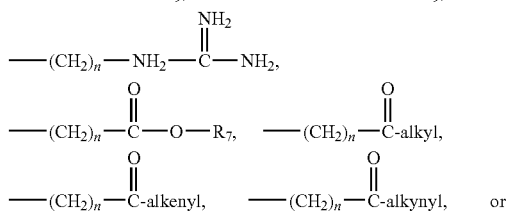

or

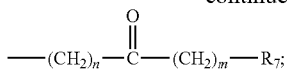

$R_7$ represents, for each occurrence, a substituted or unsubstituted aryl, aralkyl, cycloalkyl, cycloalkenyl, or heterocycle;

$R'_7$ represents, for each occurrence, hydrogen, or a substituted or unsubstituted alkyl, alkenyl, aryl, aralkyl, cycloalkyl, cycloalkenyl, or heterocycle; and $Y_1$ and $Y_2$ can independently or together be OH, or a group capable of being hydrolyzed to a hydroxyl group, including cyclic derivatives where $Y_1$ and $Y_2$ are connected via a ring having from 5 to 8 atoms in the ring structure (such as pinacol or the like), $R_{50}$ represents O or S;

$R_{51}$ represents $N_3$, $SH_2$, $NH_2$, $NO_2$ or $OR'_7$;

$R_{52}$ represents hydrogen, a lower alkyl, amine, $OR'_7$, or a pharmaceutically acceptable salt, or $R_{51}$ and $R_{52}$ taken together with the phosphorous atom to which they are attached complete a heterocyclic ring having from 5 to 8 atoms in the ring structure;

$X_1$ represents a halogen;

$X_2$ and $X_3$ each represent a hydrogen or a halogen m is zero or an integer in the range of 1 to 8; and n is an integer in the range of 1 to 8.

In certain embodiments, the ring A is a 5-, 6-, or 7-membered ring, e.g., represented by

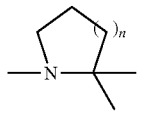

and more preferably a 5 or 6 membered ring. The ring may, optionally, be further substituted.

In certain embodiments, W represents

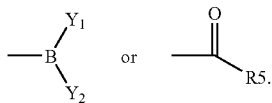

In certain embodiments, $R_1$ is

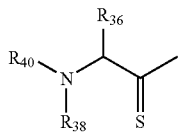

wherein $R_{36}$ is a small hydrophobic group, e.g., a lower alkyl or a halogen and $R_{38}$ is hydrogen, or, $R_{36}$ and $R_{38}$ together form a 4-7 membered heterocycle including the N and the Cα carbon, as defined for A above; and $R_{40}$ represents a C-terminally linked amino acid residue or amino acid analog, or a C-terminally linked peptide or peptide analog, or an amino-protecting group.

In certain embodiments, $R_2$ is absent, or represents a small hydrophobic group such as a lower alkyl or a halogen.

In certain embodiments, $R_3$ is a hydrogen, or a small hydrophobic group such as a lower alkyl or a halogen.

In certain embodiments, $R_5$ is a hydrogen, or a halogenated lower alkyl.

In certain embodiments, $X_1$ is a fluorine, and $X_2$ and $X_3$, if halogens, are fluorine.

Also deemed as equivalents are any compounds which can be hydrolytically converted into any of the aforementioned compounds including boronic acid esters and halides, and carbonyl equivalents including acetals, hemiacetals, ketals, and hemiketals, and cyclic dipeptide analogs.

Longer peptide sequences are needed for the inhibition of certain proteases and improve the specificity of the inhibition in some cases.

In certain embodiments, the subject method utilizes, as a DPIV inhibitor, a boronic acid analog of an amino acid or amino acid derivative, such as a thioxamide-modified amino acid. For example, the present invention contemplates the use of boro-prolyl derivatives in the subject method. Exemplary boronic acid derived inhibitors of the present invention are represented by the formula II:

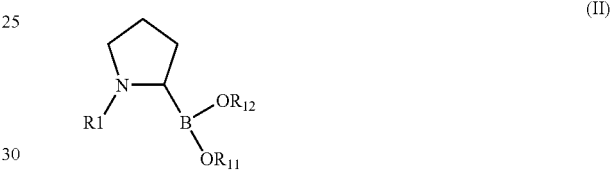

wherein $R_1$ represents a C-terminally linked amino acid residue or amino acid analog, or a C-terminally linked peptide or peptide analog, or

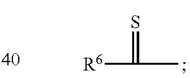

wherein the bond between $R_1$ and N is a thioxamide bond;

$R_6$ represents hydrogen, a halogen, alkyl, alkenyl, alkynyl, aryl, $-(CH_2)_m-R_7$, $-(CH_2)_m-OH$, $-(CH_2)_m-O$-alkyl, $-(CH_2)_m-O$-alkenyl, $-(CH_2)_m-O$-alkynyl, $-(CH_2)_m-O-(CH_2)_m-R_7$, $-(CH_2)_m-SH$, $-(CH_2)_m-S$-alkyl, $-(CH_2)_m-S$-alkenyl, $-(CH_2)_m-S$-alkynyl, $-(CH_2)_m-S-(CH_2)_m-R_7$,

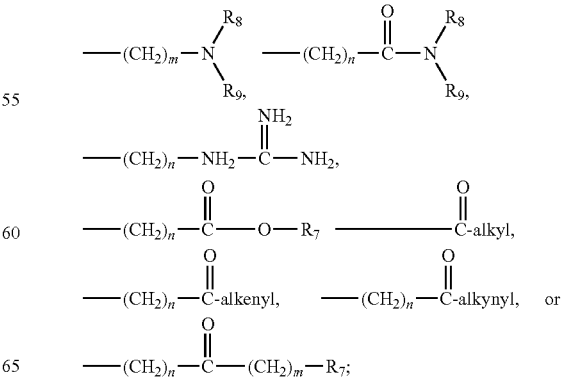

$R_7$ represents an aryl, a cycloalkyl, a cycloalkenyl, or a heterocycle;

$R_8$ and $R_9$ each independently represent hydrogen, alkyl, alkenyl, —$(CH_2)_m$—$R_7$, —$C(=O)$-alkyl, —$C(=O)$-alkenyl, —$C(=O)$-alkynyl, —$C(=O)$—$(CH_2)_m$—$R_7$, or $R_8$ and $R_9$ taken together with the N atom to which they are attached complete a heterocyclic ring having from 4 to 8 atoms in the ring structure;

$R_{11}$ and $R_{12}$ each independently represent hydrogen, a alkyl, or a pharmaceutically acceptable salt, or $R_{11}$ and $R_{12}$ taken together with the O—B—O atoms to which they are attached complete a heterocyclic ring having from 5 to 8 atoms in the ring structure;

m is zero or an integer in the range of 1 to 8; and n is an integer in the range of 1 to 8.

In other embodiments, compounds include aldehyde analogs of proline or prolyl derivatives, such as thioxamide derivatives. Exemplary aldehyde-derived compounds of the present invention are represented by the formula III:

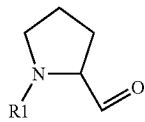

(III)

wherein $R_1$ represents a C-terminally linked amino acid residue or amino acid analog, or a C-terminally linked peptide or peptide analog, or

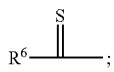

wherein the bond between $R_1$ and N is a thioxamide bond;

$R_6$ represents hydrogen, a halogen, alkyl, alkenyl, alkynyl, aryl, —$(CH_2)_m$—$R_7$, —$(CH_2)_m$—OH, —$(CH_2)_m$—O-alkyl, —$(CH_2)_m$—O-alkenyl, —$(CH_2)_m$—O-alkynyl, —$(CH_2)_m$—O—$(CH_2)_m$—$R_7$, —$(CH_2)_m$—SH, —$(CH_2)_m$—S-alkyl, —$(CH_2)_m$—S-alkenyl, —$(CH_2)_m$—S-alkynyl, —$(CH_2)_m$—S—$(CH_2)_m$—$R_7$,

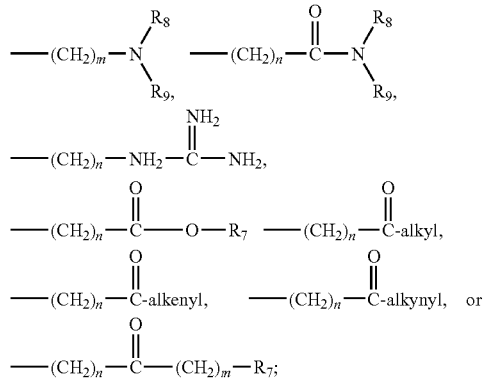

$R_7$ represents an aryl, a cycloalkyl, a cycloalkenyl, or a heterocycle;

$R_8$ and $R_9$ each independently represent hydrogen, alkyl, alkenyl, —$(CH_2)_m$—$R_7$, —$C(=O)$-alkyl, —$C(=O)$-alkenyl, —$C(=O)$-alkynyl, —$C(=O)$—$(CH_2)_m$—$R_7$, or $R_8$ and $R_9$ taken together with the N atom to which they are attached complete a heterocyclic ring having from 4 to 8 atoms in the ring structure; and m is zero or an integer in the range of 1 to 8; and n is an integer in the range of 1 to 8.

In yet further embodiments, compounds include a halomethyl ketone analog of an amino acid or amino acid derivative, such as a thioxamide-modified amino acid. Exemplary compounds of this class include compounds represented by the formula IV:

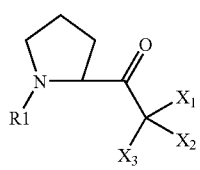

(IV)

wherein $R_1$ represents a C-terminally linked amino acid residue or amino acid analog, or a C-terminally linked peptide or peptide analog, or

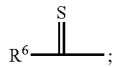

wherein the bond between $R_1$ and N is a thioxamide bond;

$R_6$ represents hydrogen, a halogen, alkyl, alkenyl, alkynyl, aryl, —$(CH_2)_m$—$R_7$, —$(CH_2)_m$—OH, —$(CH_2)_m$—O-alkyl, —$(CH_2)_m$—O-alkenyl, —$(CH_2)_m$—O-alkynyl, —$(CH_2)_m$—O—$(CH_2)_m$—$R_7$, —$(CH_2)_m$—SH, —$(CH_2)_m$—S-alkyl, —$(CH_2)_m$—S-alkenyl, —$(CH_2)_m$—S-alkynyl, —$(CH_2)_m$—S—$(CH_2)_m$—$R_7$,

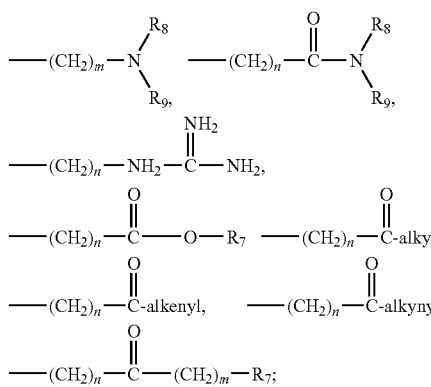

$R_7$ represents an aryl, a cycloalkyl, a cycloalkenyl, or a heterocycle;

$R_8$ and $R_9$ each independently represent hydrogen, alkyl, alkenyl, —$(CH_2)_m$—$R_7$, —$C(=O)$-alkyl, —$C(=O)$-alkenyl, —$C(=O)$-alkynyl, —$C(=O)$—$(CH_2)_m$—$R_7$, or $R_8$ and $R_9$ taken together with the N atom to which they are attached complete a heterocyclic ring having from 4 to 8 atoms in the ring structure;

$X_1$, $X_2$ and $X_3$ each represent a hydrogen or a halogen; and m is zero or an integer in the range of 1 to 8; and n is an integer in the range of 1 to 8.

In certain embodiments, compounds are peptides or peptidomimetics including a prolyl group or analog thereof in the P1 specificity position, and a nonpolar amino acid in the P2 specificity position, e.g., a nonpolar amino acid such as alanine, leucine, isoleucine, valine, proline, phenylalanine, tryptophan or methionine, or an analog thereof, such as a thioxamide analog. For example, the compound may include an Ala-Pro or Pro-Pro dipeptide sequence or equivalent thereof, and be represented in the formulas V and VI:

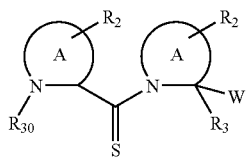
(V)

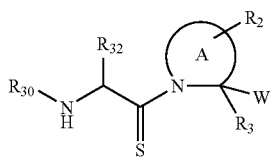
(VI)

In certain embodiments, the ring A is a 5, 6 or 7 membered ring, e.g., represented by

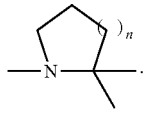

In certain embodiments, $R_{32}$ is a small hydrophobic group, e.g., a lower alkyl or a halogen.

In certain embodiments, $R_{30}$ represents a C-terminally linked amino acid residue or amino acid analog, or a C-terminally linked peptide or peptide analog, or an amino-protecting group wherein optionally where applicable the bond between $R_{30}$ and the N to which it is attached is a thioxamide bond.

In certain embodiments, $R_{30}$ is H.

In certain embodiments, $R_2$ is absent, or is or a halogen, azido, cyano, isocyanato, thiocyanato, isothiocyanato, cyanato,

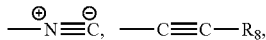

or small hydrophobic group such as a lower alkyl.

In certain embodiments, Z is C and $R_3$ is a hydrogen, or a small hydrophobic group such as a lower alkyl or a halogen.

Another representative class of compounds for use in the subject method include peptide and peptidomimetics of (D)-Ala-(L)-Ala, e.g., preserving the diasteromeric orientation, in which one or more amide groups are replaced by one or more thioxamide groups. Such compounds include compounds represented by the formula VII:

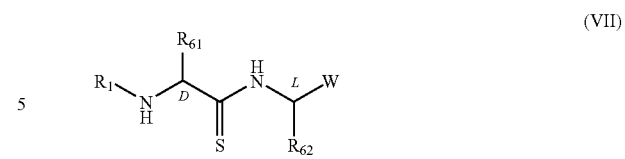
(VII)

wherein
W represents a functional group which reacts with an active site residue of the targeted protease, as for example, —CN, —CH=$NR_5$,

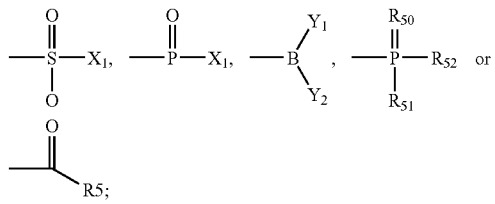

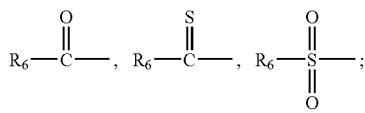

$R_1$ represents a C-terminally linked amino acid residue or amino acid analog, or a C-terminally linked peptide or peptide analog, or an amino-protecting group, or $$R_6-\overset{O}{\underset{}{C}}-, \quad R_6-\overset{S}{\underset{}{C}}-, \quad R_6-\overset{O}{\underset{O}{S}}-;$$

wherein optionally where applicable the bond between $R_1$ and the N to which it is attached is a thioxamide bond;
$R_6$ represents hydrogen, a halogen, alkyl, alkenyl, alkynyl, aryl, —$(CH_2)_m$—$R_7$, —$(CH_2)_m$—OH, —$(CH_2)_m$—O-alkyl, —$(CH_2)_m$—O-alkenyl, —$(CH_2)_m$—O-alkynyl, —$(CH_2)_m$—O—$(CH_2)_m$—$R_7$, —$(CH_2)_m$—SH, —$(CH_2)_m$—S-alkyl, —$(CH_2)_r$—S-alkenyl, —$(CH_2)_m$—S-alkynyl, —$(CH_2)_m$—S—$(CH_2)_m$—$R_7$,

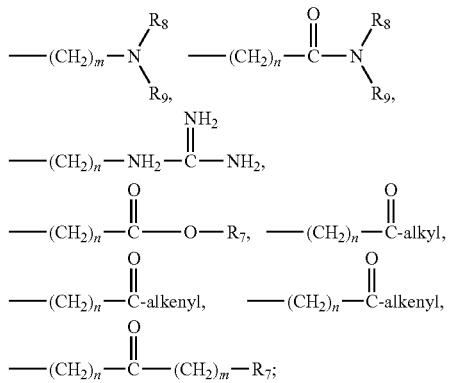

$R_7$ represents, for each occurrence, a substituted or unsubstituted aryl, aralkyl, cycloalkyl, cycloalkenyl, or heterocycle;
$R'_7$ represents, for each occurrence, hydrogen, or a substituted or unsubstituted alkyl, alkenyl, aryl, aralkyl, cycloalkyl, cycloalkenyl, or heterocycle;
$R_{61}$ and $R_{62}$, independently, represent small hydrophobic groups;

$Y_1$ and $Y_2$ can independently or together be OH, or a group capable of being hydrolyzed to a hydroxyl group, including cyclic derivatives where $Y_1$ and $Y_2$ are connected via a ring having from 5 to 8 atoms in the ring structure (such as pinacol or the like), $R_{50}$ represents O or S;

$R_{51}$ represents $N_3$, $SH_2$, $NH_2$, $NO_2$ or $OR'_7$;

$R_{52}$ represents hydrogen, a lower alkyl, an amine, $OR'_7$, or a pharmaceutically acceptable salt, or $R_{51}$ and $R_{52}$ taken together with the phosphorous atom to which they are attached complete a heterocyclic ring having from 5 to 8 atoms in the ring structure;

$X_1$ represents a halogen;

$X_2$ and $X_3$ each represent a hydrogen or a halogen m is zero or an integer in the range of 1 to 8; and n is an integer in the range of 1 to 8.

In certain embodiments, $R_1$ is

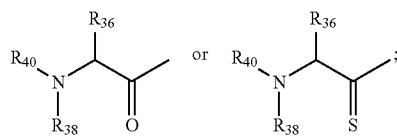

wherein $R_{36}$ is a small hydrophobic group, e.g., a lower alkyl or a halogen and $R_39$ is hydrogen, or, $R_{36}$ and $R_{38}$ together form a 4-7 membered heterocycle including the N and the Cα carbon, as defined for A above; and $R_{40}$ represents a C-terminally linked amino acid residue or amino acid analog, or a C-terminally linked peptide or peptide analog, or an amino-protecting group.

In certain embodiments, Z is C and $R_3$ is a hydrogen, or a small hydrophobic group such as a lower alkyl or a halogen.

In certain embodiments, $R_5$ is a hydrogen, or a halogenated lower alkyl.

In certain embodiments, $X_1$ is a fluorine, and $X_2$ and $X_3$, if halogens, are fluorine.

In certain embodiments, $R_{61}$ and $R_{62}$, independently, represent low alkyls, such as methyl, ethyl, propyl, isopropyl, tert-butyl or the like.

Embodiment B

Another representative class of compounds for use in the method of the present invention are represented by formula VIII:

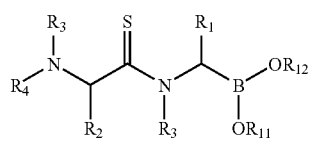

(VIII)

wherein $R_1$ represents hydrogen, halogen or lower alkyl, lower alkenyl, or lower alkynyl, preferably lower alkyl such as methyl, ethyl, etc., optionally substituted by one or more small substitutents such as halogen, hydroxy, alkoxy, etc.;

$R_2$ represents a branched lower alkyl, aralkyl, aryl, heteroaralkyl, heteroaryl, cycloalkyl, or cycloalkylalkyl, preferably a bulky hydrophobic group, such as cyclohexyl, t-butyl, etc., optionally substituted by one or more small substitutents such as halogen, hydroxy, alkoxy, etc.;

$R_3$ represents hydrogen or an amino-protecting group, preferably hydrogen;

$R_4$ represents hydrogen, a C-terminally linked amino acid residue or amino acid analog, a C-terminally linked peptide or peptide analog, an amino-protecting group, or

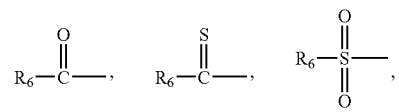

preferably hydrogen, wherein optionally where applicable the bond between $R_4$ and the N to which it is attached is a thioxamide bond;

$R_6$ represents hydrogen, a halogen, alkyl alkenyl, alkynyl, aryl, $-(CH_2)_m-R_7$, $-(CH_2)_m-OH$, $-(CH_2)_m-O$-alkyl, $-(CH_2)_m-O$-alkenyl, $-(CH_2)_m-O$-alkynyl, $-(CH_2)_m-O-(CH_2)_m-R_7$, $(CH_2)_m-SH$, $-(CH_2)_m-S$-alkyl, $-(CH_2)_m-S$-alkenyl, $-(CH_2)_m-S$-alkynyl, $-(CH_2)_m-S-(CH_2)_m-R_7$;

$R_7$ represents, for each occurrence, a substituted or unsubstituted aryl, aralkyl, cycloalkyl, cycloalkenyl, or heterocycle;

$R_{11}$ and $R_{12}$ each independently represent hydrogen, an alkyl, or a pharmaceutically acceptable salt, or $R_{11}$ and $R_{12}$ taken together with the O—B—O atoms to which they are attached complete a heterocyclic ring having from 5 to 8 atoms in the ring structure; and m is zero or an integer in the range of 1 to 8.

In other embodiments, the subject compounds include aldehyde analogs of alanine or alanyl derivatives, such as thioxamide-modified derivatives. Exemplary compounds of the present invention are represented by the formula IX:

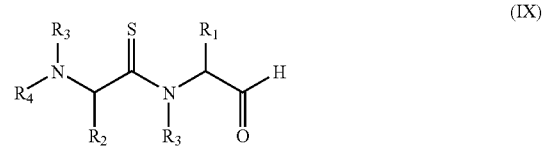

(IX)

wherein $R_1$ represents hydrogen, halogen or lower alkyl, lower alkenyl, or lower alkynyl, preferably lower alkyl such as methyl, ethyl, etc., optionally substituted by one or more small substitutents such as halogen, hydroxy, alkoxy, etc.;

$R_2$ represents a branched lower alkyl, aralkyl, aryl, heteroaralkyl, heteroaryl, cycloalkyl, or cycloalkylalkyl, preferably a bulky hydrophobic group, such as cyclohexyl, t-butyl, etc., optionally substituted by one or more small substitutents such as halogen, hydroxy, alkoxy, etc.;

$R_3$ represents hydrogen or an amino-protecting group, preferably hydrogen;

$R_4$ represents hydrogen, a C-terminally linked amino acid residue or amino acid analog, a C-terminally linked peptide or peptide analog, an amino-protecting group, or

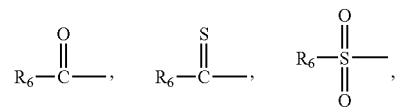

preferably hydrogen, wherein optionally where applicable the bond between $R_4$ and the N to which it is attached is a thioxamide bond;

R$_6$ represents hydrogen, a halogen, alkyl, alkenyl, alkynyl, aryl, —(CH$_2$)$_m$—R$_7$, —(CH$_2$)$_m$—OH, —(CH$_2$)$_m$—O-alkyl, —(CH$_2$)$_m$—O-alkenyl, —(CH$_2$)$_m$—O-alkynyl, —(CH$_2$)$_m$—O—(CH$_2$)$_m$—R$_7$, —(CH$_2$)$_m$—SH, —(CH$_2$)$_m$—S-alkyl, —(CH$_2$)$_m$—S-alkenyl, —(CH$_2$)$_m$—S-alkynyl, —(CH$_2$)$_m$—S—(CH$_2$)$_m$—R$_7$;

R$_7$ represents, for each occurrence, a substituted or unsubstituted aryl, aralkyl, cycloalkyl, cycloalkenyl, or heterocycle;

m is zero or an integer in the range of 1 to 8.

In yet further embodiments, the compounds are halo-methyl ketone analogs of an amino acid or thioxamide-modified amino acid. Exemplary inhibitors of this class include compounds represented by the formula X:

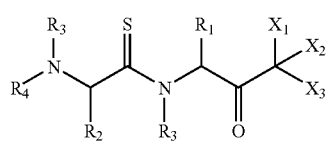

(X)

wherein

R$_1$ represents hydrogen, halogen or lower alkyl, lower alkenyl, or lower alkynyl, preferably lower alkyl such as methyl, ethyl, etc., optionally substituted by one or more small substitutents such as halogen, hydroxy, alkoxy, etc.;

R$_2$ represents a branched lower alkyl, aralkyl, aryl, heteroaralkyl, heteroaryl, cycloalkyl, or cycloalkylalkyl, preferably a bulky hydrophobic group, such as cyclohexyl, t-butyl, etc., optionally substituted by one or more small substitutents such as halogen, hydroxy, alkoxy, etc.;

R$_3$ represents hydrogen or an amino-protecting group, preferably hydrogen;

R$_4$ represents hydrogen, a C-terminally linked amino acid residue or amino acid analog, a C-terminally linked peptide or peptide analog, an amino-protecting group, or

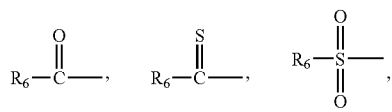

preferably hydrogen, where optionally where applicable the bond between R$_4$ and the N to which it is attached is a thioxamide bond;

R$_6$ represents hydrogen, a halogen, alkyl, alkenyl, alkynyl, aryl, —(CH$_2$)$_m$—R$_7$, —(CH$_2$)$_m$—OH, —(CH$_2$)$_m$—O-alkyl, —(CH$_2$)$_m$—O-alkenyl, —(CH$_2$)$_m$—O-alkynyl, —(CH$_2$)$_m$—O—(CH$_2$)$_{m-1}$ R$_7$, —(CH$_2$)$_m$—SH, —(CH$_2$)$_m$—S-alkyl, —(CH$_2$)$_m$—S-alkenyl, —(CH$_2$)$_m$—S-alynyl, —(CH$_2$)$_m$—S—(CH$_2$)$_m$—R$_7$;

R$_7$ represents, for each occurrence, a substituted or unsubstituted aryl, aralkyl, cycloalkyl, cycloalkenyl, or heterocycle;

X$_1$, X$_2$ and X$_3$ each represent a hydrogen or a halogen;

m is zero or an integer in the range of 1 to 8.

In certain embodiments, the compound is a peptide or peptidomimetic including a alaninyl group or analog thereof, such as a thioxamide analog, in the P1 specificity position, and a non-naturally occurring amino acid in the P2 specificity position, or an analog thereof, such as a thioxamide analog. For example, the compound may include an Cyclohexylglycine-Ala or t-butylglycine-Ala dipeptide sequence or equivalent thereof, and be represented in the formula XI:

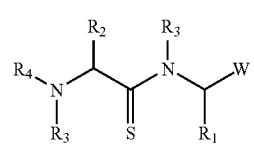

(XI)

R$_1$ represents hydrogen, halogen or lower alkyl, lower alkenyl, or lower alkynyl, preferably lower alkyl such as methyl, ethyl, etc., optionally substituted by one or more small substitutents such as halogen, hydroxy, alkoxy, etc.;

R$_2$ represents a branched lower alkyl, aralkyl, aryl, heteroaralkyl, heteroaryl, cycloalkyl, or cycloalkylalkyl, preferably a bulky hydrophobic group, such as cyclohexyl, t-butyl, etc., optionally substituted by one or more small substitutents such as halogen, hydroxy, alkoxy, etc.;

R$_3$ represents hydrogen or an amino-protecting group, preferably hydrogen;

R$_4$ represents hydrogen, a C-terminally linked amino acid residue or amino acid analog, a C-terminally linked peptide or peptide analog, an amino-protecting group, or

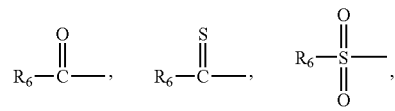

preferably hydrogen, where optionally where applicable the bond between R$_4$ and the N to which it is attached is a thioxamide bond;

R$_6$ represents hydrogen, a halogen, alkyl, alkenyl, alkynyl, aryl, —(CH$_2$)$_m$—R$_7$, —(CH$_2$)$_m$—OH, —(CH$_2$)$_m$—O-alkyl, —(CH$_2$)$_m$—O-alkenyl, —(CH$_2$)$_m$—O-alkynyl, (CH$_2$)$_m$—O—(CH$_2$)$_m$—R$_7$, —(CH$_2$)$_m$—SH, —(CH$_2$)$_m$—S-alkyl, —(CH$_2$)$_m$—S-alkenyl, —(CH$_2$)$_m$—S-alkynyl, —(CH$_2$)$_m$—S—(CH$_2$)$_m$—R$_7$;

R$_7$ represents, for each occurrence, a substituted or unsubstituted aryl, aralkyl, cycloalkyl, cycloalkenyl, or heterocycle;

W represents a functional group which reacts with an active site residue of the targeted protease, as for example, —CN, —CH—NR$_{53}$,

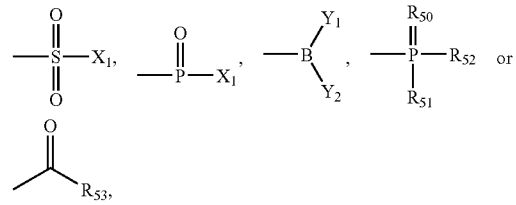

preferably

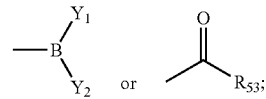

$Y_1$ and $Y_2$ are, independently, OH, or a group capable of being hydrolyzed, e.g., under physiologic conditions to a hydroxyl group, such as alkoxy, aryloxy, etc., including cyclic derivatives where $Y_1$ and $Y_2$ are connected via a ring having from 5 to 8 atoms in the ring structure (such as pinacol or the like);

$R_{50}$ represents O or S;

$R_{51}$ represents $N_3$, SH, $NH_2$, $NO_2$ or $OR'_7$;

$R_{52}$ represents hydrogen, a lower alkyl, an amine, $OR'_7$, or a pharmaceutically acceptable salt, or $R_{51}$ and $R_{52}$ taken together with the phosphorous atom to which they are attached complete a heterocyclic ring having from 5 to 8 atoms in the ring structure;

$R_{53}$ represents hydrogen, an alkyl, an alkenyl, an alkynyl, $-C(X_1)(X_2)-X_3$, $-(CH_2)_m-R_7$, $-(CH_2)_n-OH$, $-(CH_2)_n-$O-alkyl, $-(CH_2)_n-$O-alkenyl, $-(CH_2)_n-$O-alkynyl, $-(CH_2)_n-$O$-(CH_2)_m-R_7$, $-(CH_2)_n-$SH, $-(CH_2)_n-$S-alkyl, $-(CH_2)_n-$S-alkenyl, $-(CH_2)_n-$S-alkynyl, $-(CH_2)_n-$S$-(CH_2)_m-R_7$, $-C(O)C(O)NH_2$, $-C(O)C(O)OR'_7$, preferably a hydrogen, or a halogenated lower alkyl;

$X_1$ represents a halogen, preferably a fluorine;

m is zero or an integer in the range of 1 to 8; and n is an integer in the range of 1 to 8.

Another representative class of compounds for use in the subject method include peptide and peptidomimetics of (L)-Ala-(L)-Cyclohexylglycine or thioxamide analogs thereof, e.g., preserving the steric disposition of moieties. Such inhibitors include compounds represented by the formula XII:

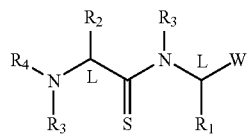

(XII)

wherein $R_1$ represents hydrogen, halogen or lower alkyl, lower alkenyl, or lower alkynyl, preferably lower alkyl such as methyl, ethyl, etc., optionally substituted by one or more small substitutents such as halogen, hydroxy, alkoxy, etc.;

$R_2$ represents a branched lower alkyl, aralkyl, aryl, heteroaralkyl, heteroaryl, cycloalkyl, or cycloalkylalkyl, preferably a bulky hydrophobic group, such as cyclohexyl, t-butyl, etc., optionally substituted by one or more small substituents such as halogen, hydroxy, alkoxy, etc.;

$R_3$ represents hydrogen or an amino-protecting group, preferably hydrogen;

$R_4$ represents hydrogen, a C-terminally linked amino acid residue or amino acid analog, a C-terminally linked peptide or peptide analog, an amino-protecting group, or

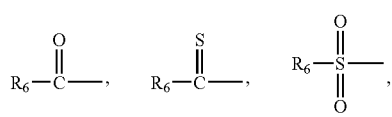

preferably hydrogen, wherein optionally where applicable the bond between $R_4$ and the N to which it is attached is a thioamide bond;

$R_6$ represents hydrogen, a halogen, alkyl, alkenyl, alkynyl, aryl, $-(CH_2)_m-R_7$, $-(CH_2)_m-OH$, $-(CH_2)_m-$O-alkyl, $-(CH_2)_m-$O-alkenyl, $-(CH_2)_m-$O-alkynyl, $-(CH_2)_m-$O$-(CH_2)_m-R_7$, $-(CH_2)_m-$SH, $-(CH_2)_m-$S-alkyl, $-(CH_2)_m-$S-alkenyl, $-(CH_2)_m-$S-alkynyl, $-(CH_2)_m-$S$-(CH_2)_m-R_7$;

$R_7$ represents, for each occurrence, a substituted or unsubstituted aryl, aralkyl, cycloalkyl, cycloalkenyl, or heterocycle;

W represents a functional group which reacts with an active site residue of the targeted protease, as for example, $-CN$, $-CH=NR_{53}$,

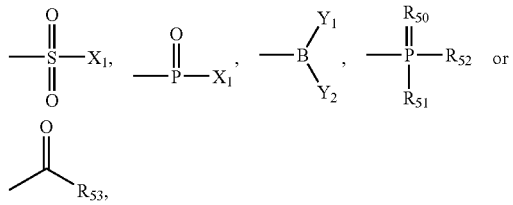

preferably

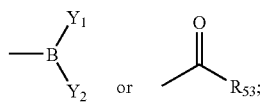

$Y_1$ and $Y_2$ are, independently, OH, or a group capable of being hydrolyzed, e.g., under physiologic conditions to a hydroxyl group, such as alkoxy, aryloxy, etc., including cyclic derivatives where $Y_1$ and $Y_2$ are connected via a ring having from 5 to 8 atoms in the ring structure (such as pinacol or the like);

$R_{50}$ represents O or S;

$R_5$, represents $N_3$, SH, $NH_2$, $NO_2$ or $OR'_7$;

$R_{52}$ represents hydrogen, a lower alkyl, amine, $OR'_7$, or a pharmaceutically acceptable salt, or $R_{51}$ and $R_{52}$ taken together with the phosphorous atom to which they are attached complete a heterocyclic ring having from 5 to 8 atoms in the ring structure;

$R_{53}$ represents hydrogen, alkyl, alkenyl, alkynyl, $-C(X_1)(X_2)-X_3$, $-(CH_2)_m-R_7$, $-(CH_2)_n-OH$, $-(CH_2)_n-$O-alkyl, $-(CH_2)_n-$O-alkenyl, $-(CH_2)_n-$O-alkynyl, $-(CH_2)_n-$O$-(CH_2)_m-R_7$, $-(CH_2)_n-$SH, $-(CH_2)_n-$S-alkyl, $-(CH_2)_n-$S-alkenyl, $-(CH_2)_n-$S-alkynyl, $-(CH_2)_n-$S$-(CH_2)_m-R_7$, $-C(O)C(O)NH_2$, $-C(O)C(O)OR'_7$, preferably a hydrogen, or a halogenated lower alkyl;

$X_1$ represents a halogen, preferably a fluorine;

m is zero or an integer in the range of 1 to 8;

and n is an integer in the range of 1 to 8.

Embodiment C

A representative class of compounds for use in the method of the present invention are represented by formula XIII:

A-G    (XIII)

or a pharmaceutically acceptable salt thereof, wherein

A represents a peptidyl moiety which is a substrate for an activating protease;

A and G are covalently linked by a bond that is cleaved by the activating protease;

G represents an inhibitor of a target protease which, when cleaved from A by the activating serine protease, is characterized by one or both of the following: undergoes protodeboronation and/or inhibits the target protease with a Ki of 100 nM or less; and the compound of Formula XIII comprises one or more thioxamide groups.

In certain embodiments, the activating protease can be a serine protease, a cysteine protease or a metalloprotease. Likewise, the target protease can be a serine protease, a cysteine protease or a metalloprotease. In certain certain embodiments, the target and activating proteases are serine proteases.

In certain certain embodiments, the activating protease is a post-prolyl cleaving protease, such as selected from the group consisting of DPP IV, DPP II, Prolyl oligopeptidase (PO), Fibroblast Activating Protein (FAP), and prolyl carboxypeptidase. In certain embodiments, the post-prolyl cleaving protease is an endopeptidase, and A includes a blocked amino terminus.

In other embodiments, the activating protease is selected from the group consisting of the group consisting of thrombin (Factor X), matriptase, falcipain, prostate specific antigen (PSA), and proteases homologous thereto.

In certain certain embodiments, the target protease is a post-prolyl cleaving protease, such as selected from the group consisting of DPP IV, DPP II, Prolyl oligopeptidase (PO), Fibroblast Activating Protein (FAP), and prolyl carboxypeptidase.

In certain embodiments, G is a dipeptidyl moiety, e.g., derived from naturally occurring amino acids or analogs thereof.

In certain embodiments, G represents an inhibitor of a target protease which, when cleaved from A by the activating serine protease, inhibits the target protease with a Ki of 100 nM or less, and certain certain embodiments, 10, 1 or 0.1 nM or less.

In certain certain embodiments, the half-life time ($T_{1/2}$) in serum for the inhibitor G is less than 24 hours, and even more preferably less than 10 hours, 1 hour or even 10 min.

In certain embodiments, the address moiety A represents a C-terminally linked peptide or peptide analog, e.g., of 2-10 amino acid residues, more preferably 2-4 residues, which is a substrate for the activating enzyme. In certain certain embodiments, A is a dipeptidyl or tripepidyl moiety. In certain embodiments, A is derived from naturally occurring amino acids or analogs thereof and in certain certain embodiments, at least one residue of A is a non-naturally occurring amino acid analog.

In certain certain embodiments, such as when the address moiety A is a substrate of DPP IV, the amino terminus of the peptide or peptide analog is blocked with an amino-terminal protecting group, preferably a lower alkyl such as a methyl group.

In certain embodiments, the inhibitor moiety G is a dipeptidyl moiety and a electrophilic functional group that can form a covalent adduct with a residue in the active site of a protease replacing the carboxyl terminus of the dipeptidyl moiety. For instance, the inhibitor moiety G can be represented in the formula XIV:

$Xaa_1$-$Xaa_2$-W    (XIV)

wherein $Xaa_1$ is a naturally occurring amino acid or analog thereof, wherein $Xaa_1$ contains a thioxamide group;

$Xaa_2$ is a naturally occurring amino acid or analog thereof;

W represents a functional group which reacts with an active site residue of the targeted protease to form a covalent adduct, as for example, —CN, —CH=NR$_5$,

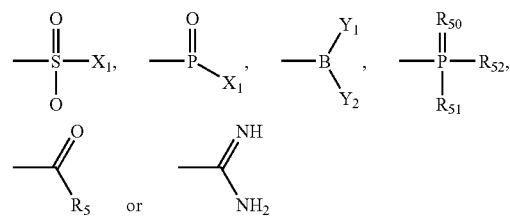

$R_5$ represents H, alkyl, alkenyl, alkynyl, —C(X$_1$)(X$_2$)X$_3$, —(CH$_2$)m—R$_6$, —(CH$_2$)n—OH, —(CH$_2$)n—O-alkyl, —(CH$_2$)n—O-alkenyl, —(CH$_2$)n—O-alkynyl, —(CH$_2$)n—O—(CH$_2$)m—R$_6$, —(CH$_2$)n—SH, —(CH$_2$)n—S-alkyl, —(CH$_2$)n—S-alkenyl, —(CH$_2$)n—S-alkynyl, —(CH$_2$)n—S—(CH$_2$)m—R$_6$, —C(O)C(O)NH$_2$, or —C(O)C(O)OR$_7$;

$R_6$ represents a substituted or unsubstituted aryl, aralkyl, cycloalkyl, cycloalkenyl, or heterocycle;

$R_7$ represents independently for each occurrence hydrogen, or a substituted or unsubstituted alkyl, alkenyl, aryl, aralkyl, cycloalkyl, cycloalkenyl, or heterocycle; and $Y_1$ and $Y_2$ can independently or together be —OH, or a group capable of being hydrolyzed to a hydroxyl group, including cyclic derivatives where $Y_1$ and $Y_2$ are connected via a ring having from 5 to 8 atoms in the ring structure (such as pinacol or the like), $R_{50}$ represents O or S;

$R_{51}$ represents N$_3$, SH$_2$, NH$_2$, NO$_2$ or —OR$_7$;

$R_{52}$ represents hydrogen, a lower alkyl, an amine, —OR$_7$, or a pharmaceutically acceptable salt, or $R_{51}$ and $R_{52}$ taken together with the phosphorous atom to which they are attached complete a heterocyclic ring having from 5 to 8 atoms in the ring structure $X_1$ represents a halogen;

$X_2$ and $X_3$ each represent a hydrogen or a halogen;

m is zero or an integer in the range of 1 to 8; and n is an integer in the range of 1 to 8.

The pro-soft inhibitors of the present invention do not themselves undergo proto-deboronation and can be constructed such that they do not inhibit the selected target enzyme, or other enzymes to any significant extent, before being cleaved by the activating protease. That is, the pro-soft inhibitors are themselves inactive, but produce an active inhibitor moiety G in the body when the address moiety A is removed from the pro-soft inhibitor.

One of the features that makes the pro-soft inhibitor molecules of the current invention different from typical prodrugs is that the inhibitor moiety, after being generated in the active form near the target, undergoes inactivation over time, e.g., as it diffuses away from the target enzyme, thereby reducing the possibility of deleterious side effects that may result from inhibition of enzymes occurring in other parts of the patient. This combination of being released in an active form in the vicinity of the target enzyme together with this "programmed" deactivation mechanism makes the molecules of the invention more specific, effective, and safer (i.e., having fewer side effects) than the inhibitor moiety used on its own.

In certain embodiments, the inhibitor moiety G is a dipeptidyl moiety, e.g., derived from naturally occurring amino acids or amino acid analogs comprising a thioamide moiety.

In certain embodiments, the inhibitor moiety G is an inhibitor of a target protease which, when cleaved from pro-soft inhibitor by the activating protease, inhibits the target protease with a $K_i$ of 100 nM ($10^{-7}$M) or less, and even more preferably, a Ki less than equal to 25 nM, 10 nM ($10^{-8}$M), mM ($10^{-9}$M), or 0.1 nM ($10^{-10}$M). In certain embodiments, $K_i$'s of less than $10^{-11}$M and even $10^{-12}$M have been measured or estimated for the subject inhibitor moieties.

In certain certain embodiments, the therapeutic index for the pro-soft inhibitor is at least 2 times greater than the therapeutic index for the inhibitor moiety alone, and even more preferably 5, 10, 50 or even 100 times greater.

For many of the subject pro-soft inhibitors, another improvement over the inhibitor moiety itself is increased stability in pharmaceutical preparations, such as in solution, oils or solid formulations. Such stability can be expressed in terms of shelf-life. In certain certain embodiments, the subject pro-soft inhibitor has a $T_{90}$ of at least 7 days, and even more preferably of at least 20, 50, 100 or even 200 days. In certain certain embodiments, the subject pro-soft inhibitor has a $T_{50}$ of at least 20 days, and even more preferably of at least 50, 100, 200 or even 400 days. In certain certain embodiments, the subject pro-soft inhibitor has a $T_{90}$ as a solid, single oral dosage formulation of at least 20, 50, 100 or even 200 days. In certain certain embodiments, the subject pro-soft inhibitor has a $T_{90}$ as a liquid, single dosage suspension of at least 20, 50, 100 or even 200 days.

Preferred pharmaceutical preparations of the subject pro-soft inhibitors are substantially pyrogen-free. For example, in certain certain embodiments, the endotoxin concentration of the subject preparation, as assayed by the via the gel-clot method (as a limits test with comparison to the maximum allowed FDA limit, as stated in appendix E of the Endotoxin Guidance), is less than 10 EU/mL or EU/single dosage formulation, and even more preferably less than 5, 1, or even 0.1 EU/mL or EU/single dosage formulation.

In certain embodiments, a single administration of the pro-soft inhibitor, such as bolus injection, oral dosage or inhaled dosage, can produce a sustained in vivo effect, such as to provide a therapeutically effective amount (>$ED_{50}$ concentration) of the inhibitor moiety G for a period of at least 4 hours, and even more preferably at least 8, 12 or even 16 hours.

In certain certain embodiments, the released inhibitor moiety G, and particularly the inactive compound, has half-life (e.g., relative to decomposition into lower molecular weight fragments) in serum or other biologically relevant fluid of greater than 10 hours, and even more preferably a half-life greater than 24, 48 or 120 hours.

Formulations of the present invention include those especially formulated for oral, buccal, parental, transdermal, inhalation, intranasal, transmucosal, implant, or rectal administration. In certain certain embodiments, the subject inhibitors are orally available, and can be provided in the form of solid dosage formulations suitable for oral administration to a human patient. In certain certain embodiments, the subject inhibitors are transdermally active, and can be provided in the form of topical cream or suspension or a transdermal patch.

Another aspect of the invention provides a pharmaceutical package including one or more of the subject pro-soft inhibitors, and instructions (written and/or pictorial) describing the administration of the formulation to a patient. Merely to illustrate, exemplary packages are appropriately dosed and include instructions for one or more of: treatment or prophylaxis of metabolic disorders, gastrointestinal disorders, viral disorders, inflammatory disorders, diabetes, obesity, hyperlipidemia, dermatological or mucous membrane disorders, psoriasis, intestinal distress, constipation, autoimmune disorders, encephalomyelitis, complement mediated disorders, glomerulonephritis, lipodystrophy; tissue damage, psychosomatic, depressive, and neuropsychiatric disorders, HIV infection, allergies, inflammation, arthritis, transplant rejection, high blood pressure, congestive heart failure, tumors, and stress-induced abortions.

Preferably, the package includes the one or more pro-soft inhibitors provided as a single oral dosage formulation.

Where the pro-soft inhibitor includes one more chiral centers, in certain embodiments, the pro-soft inhibitor is provided as at least 75 mol % of the eutomer (relative to the distomer) of that pro-soft inhibitor, and even more preferably at least 85, 90, 95 or even 99 mol %. Generally, the eutomer with the L-enantiomer (with respect to the Cα carbon) of an amino acid or amino acid analog.

In certain embodiments, the pro-soft inhibitor is a tetrapeptidyl moiety represented in the formula XV:

$$Xaa_1'\text{-}Xaa_2'\text{-}Xaa_1\text{-}Xaa_2\text{-}W \qquad (XV)$$

wherein $Xaa_1'$, $Xaa_2'$, and $Xaa_2$ each independently represent a naturally occurring amino acid or analog thereof;

$Xaa_1$ is a naturally occurring amino acid or analog thereof, wherein $Xaa_1$ contains a thioxamide group;

W represents a functional group which reacts with an active site residue of the targeted protease to form a covalent adduct, as for example, —CN, —CH=$NR_5$,

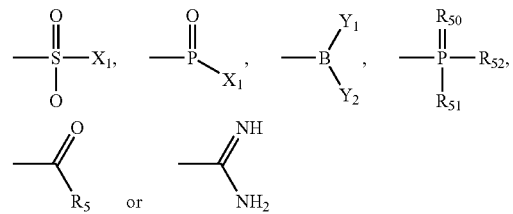

$R_5$ independently for each occurrence H, alkyl, alkenyl, alkynyl, —C($X_1$)($X_2$)$X_3$, —($CH_2$)m-$R_6$, —($CH_2$)n—OH, —($CH_2$)n—O-alkyl, —($CH_2$)n—O-alkenyl, —($CH_2$)n—O-alkynyl, —($CH_2$)n—O—($CH_2$)m-$R_6$, —($CH_2$)n—SH, —($CH_2$)n—S-alkyl, —($CH_2$)n—S-alkenyl, —($CH_2$)n—S-alkynyl, —($CH_2$)n—S—($CH_2$)m-$R_6$, —C(O)C(O)$NH_2$, or —C(O)C(O)$OR_7$;

$R_6$ represents independently for each occurrence a substituted or unsubstituted aryl, aralkyl, cycloalkyl, cycloalkenyl, or heterocycle;

$R_7$ represents independently for each occurrence hydrogen, or a substituted or unsubstituted alkyl, alkenyl, aryl, aralkyl, cycloalkyl, cycloalkenyl, or heterocycle;

$Y_1$ and $Y_2$ can independently or together be OH, or a group capable of being hydrolyzed to a hydroxyl group, including cyclic derivatives where $Y_1$ and $Y_2$ are connected via a ring having from 5 to 8 atoms in the ring structure (such as pinacol or the like), $R_{50}$ represents O or S;

$R_{51}$ represents $N_3$, $SH_2$, $NH_2$, $NO_2$ or —$OR_7$;

$R_{52}$ represents hydrogen, a lower alkyl, an amine, —$OR_7$, or a pharmaceutically acceptable salt, or $R_{51}$ and $R_{52}$ taken together with the phosphorous atom to which they are attached complete a heterocyclic ring having from 5 to 8 atoms in the ring structure $X_1$ represents a halogen;

$X_2$ and $X_3$ each represent a hydrogen or a halogen;

m is zero or an integer in the range of 1 to 8; and n is an integer in the range of 1 to 8.

In certain certain embodiments, $Xaa_1'$ includes an amino-terminal protecting group.

In certain certain embodiments, Xaa$_1$' is an amino acid analog having a tetrasubstituted Cβ carbon, e.g., a carbon having four substituents none of which is a hydrogen. For instance, Xaa$_1$' can be an amino acid analog represented in the formula:

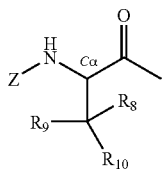

wherein: R$_8$ and R$_9$ each independently represent a lower alkyl or a halogen; R$_{10}$ represents a lower alkyl, an aryl, a hydroxyl group or —(CH$_2$)$_m$—COOH; Z represents a hydrogen or an amino terminal protecting group; and m=0, 1 or 2. In certain certain embodiments, R$_8$ and R$_9$ each independently represents a lower alkyl, more preferably methyl, ethyl or propyl, and even more preferably a methyl. In certain certain embodiments, R$_{10}$ represents a lower alkyl, more preferably methyl, ethyl or propyl, and even more preferably a methyl. In other certain embodiments, R$_{10}$ represents an aryl, such as phenyl or hydroxyphenyl (preferably para-hydroxy). In yet other certain embodiments, R$_{10}$ represents a hydroxyl group. In certain certain embodiments, R$_{10}$ represents —(CH$_2$)$_m$—COOH, where m=0, 1 or 2, and preferably where m is 0 or 1.

In certain embodiments, W is —B(Y$_1$)(Y$_2$).

In certain embodiments, R$_2$ is absent or represents halogen or lower alkyl.

In certain embodiments, R$_4$ represents hydrogen or lower alkyl.

In certain embodiments, R$_5$ represents H or alkyl.

In certain embodiments, Y$_1$ and Y$_2$ are OH.

In certain embodiments, W is —B(OH)$_2$.

In general, the subject pro-soft inhibitors can be divided into two distinct types on the basis of whether they are activated by the same, or by a different enzyme as the target enzyme of the inhibitor moiety. The first type will be referred to as Type 1 or Target-Activated Smart Protease Inhibitors (TASPI), the second as Type 2 or Target-Directed Smart Protease Inhibitors (TDSPI). Both embodiments of the pro-soft inhibitors provide for the specific delivery of the active component to the targeted enzyme and provide for attenuation of the inhibitor activity as the inhibitor moiety diffuses away from the target enzyme.

TDSPIs of the present invention offer the additional prospects for tissue, or cellular specific inhibition of targeted enzymes. In other words TDSPIs offer the prospect of inhibiting a given enzyme in one given cell or tissue type but not in another. For example, every cell of the body contains a proteasome protease complex. Inhibition of proteasome function has a number of practical therapeutic and prophylactic applications. However, it is difficult to provide for inhibition of proteasome activity in a cell- or tissue-type selective manner. In certain embodiments of the current invention, TDSPIs can be constructed to deliver a proteasome inhibitor moiety in selective manner by using a pro-soft inhibitor having an address moiety for a protease that is expressed in or adjacent to the intended target cells or tissue. To illustrate, it can be activated by FAP or Prostate Specific Antigen (PSA) and the resulting inhibitor moiety G is an inhibitor of the proteasome.

In certain embodiments of TDSPIs, the address moiety A is not an efficient substrate for the target protease. For instance, as a substrate, address moiety A preferably has a turnover number as a substrate for the target protease of less than 1/second, and even more preferably less than 0.1/second, 0.001/second or even 0.0001/second.

In certain embodiments of the subject pro-soft inhibitors, the address moiety is a substrate for an activating protease selected from amongst serine proteases, cysteine proteases and metalloproteases. Likewise, the inhibitor moiety can be an dipeptidyl inhibitor for a target protease selected from serine proteases, cysteine proteases and metalloproteases. In certain certain embodiments, the target protease is a serine proteases.

The pro-soft inhibitors of the present invention can be designed to work with target and activating serine proteases including, but not limited to, dipeptidyl peptidase-11 (DPP-XI), dipeptidyl peptidase IV (DPP IV), dipeptidyl peptidase (DPP VIII), dipeptidyl peptidase 9 (DPP IX), aminopeptidase P, fibroblast activating protein alpha (seprase), prolyl tripeptidyl peptidase, prolyl oligopeptidase (endoproteinase Pro-C), attractin (soluble dipeptidyl-aminopeptidase), acylaminoacyl-peptidase (N-acylpeptide hydrolase; fMet aminopeptidase) and lysosomal Pro-X carboxypeptidase (angiotensinase C, prolyl carboxypeptidase).

The pro-soft inhibitors of the present invention can be designed to work with target and activating metalloproteases including membrane Pro-X carboxypeptidase (carboxypeptidase P), angiotensin-converting enzyme (Peptidyl-dipeptidase A multipeptidase], collagenase I (interstitial collagenase; matrix metalloproteinase 1; MMP-1; Mcol-A), ADAM 10 (alpha-secretase, myelin-associated disintegrin metalloproteinase), neprilysin (atriopeptidase; CALLA; CD10; endopeptidase 24.11; enkephalinase), Macrophage elastase (metalloelastase; matrix metalloproteinase 12; MMP-12], Matrilysin (matrix metalloproteinase 7; MMP-7), and neurolysin (endopeptidase 24.16; microsomal endopeptidase; mitochondrial oligopeptidase).

In certain certain embodiments, the activating protease is a post-prolyl cleaving protease, such as selected from the group consisting of DPP IV, DPP II, Prolyl oligopeptidase (PO), Fibroblast Activating Protein (FAP), and prolyl carboxypeptidase. In certain embodiments where the post-prolyl cleaving protease is an endopeptidase, the amino terminus of A is blocked with an amino-terminal protecting group, preferably a lower alkyl such as a methyl group.

In certain certain embodiments, the subject compound is represented by the formula XVI:

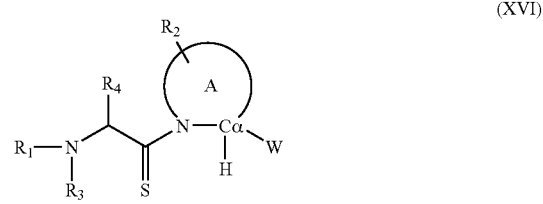

wherein

A represents a 4-8 membered heterocycle including the N and the Cα carbon;

W represents a functional group which reacts with an active site residue of the targeted protease to form a covalent adduct, as for example, —CN, —CH=NR$_5$,

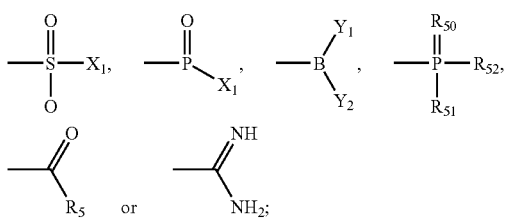

R$_1$ represents a C-terminally linked peptide or peptide analog which is a substrate for an activating enzyme;

R$_2$ is absent or represents one or more substitutions to the ring A, each of which is independently a halogen, lower alkyl, lower alkenyl, lower alkynyl, carbonyl (such as a carboxyl, ester, formate, or ketone), thiocarbonyl (such as a thioester, thioacetate, or thioformate), amino, acylamino, amido, nitro, sulfate, sulfonate, sulfonamido, —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_7$, —(CH$_2$)$_m$—SH, —(CH$_2$)$_m$—S-lower alkyl, —(CH$_2$)$_m$—S-lower alkenyl, or —(CH$_2$)$_n$—S—(CH$_2$)$_m$—R$_7$ azido, cyano, isocyanato, thiocyanato, isothiocyanato, cyanato,

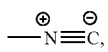

or

R$_3$ represents a hydrogen or a substituent which does not conjugate the electron pair of the nitrogen to which it is attached, such as a lower alkyl;

R$_4$ represents hydrogen, halogen, a lower alkyl, lower alkenyl, lower alkynyl, aryl, or aralkyl;

R$_5$ represents H, alkyl, alkenyl, alkynyl, —C(X$_1$)(X$_2$)X$_3$, —(CH$_2$)m-R$_6$, —(CH$_2$)n—OH, —(CH$_2$)n—O-alkyl, —(CH$_2$)n—O-alkenyl, —(CH$_2$)n—O-alkynyl, —(CH$_2$)n—O—(CH$_2$)m-R$_6$, —(CH$_2$)n—SH, —(CH$_2$)n—S-alkyl, —(CH$_2$)n—S-alkenyl, —(CH$_2$)n—S-alkynyl, —(CH$_2$)n—S—(CH$_2$)m-R$_6$, —C(O)C(O)NH$_2$, or —C(O)C(O)OR$_7$;

R$_6$ represents independently for each occurrence a substituted or unsubstituted aryl, aralkyl, cycloalkyl, cycloalkenyl, or heterocycle;

R$_7$ represents independently for each occurrence hydrogen, or a substituted or unsubstituted alkyl, alkenyl, aryl, aralkyl, cycloalkyl, cycloalkenyl, or heterocycle;

R$_8$ represents hydrogen, —CH$_3$, or —(CH$_2$)$_n$—CH$_3$;

Y$_1$ and Y$_2$ can independently or together be OH, or a group capable of being hydrolyzed to a hydroxyl group, including cyclic derivatives where Y$_1$ and Y$_2$ are connected via a ring having from 5 to 8 atoms in the ring structure (such as pinacol or the like);

R$_{50}$ represents O or S;

R$_{51}$ represents N$_3$, SH$_2$, NH$_2$, NO$_2$ or —OR$_7$;

R$_{52}$ represents hydrogen, a lower alkyl, an amine, —OR$_7$, or a pharmaceutically acceptable salt, or R$_{51}$ and R$_{52}$ taken together with the phosphorous atom to which they are attached complete a heterocyclic ring having from 5 to 8 atoms in the ring structure;

X$_1$ represents a halogen;

X$_2$ and X$_3$ each represent a hydrogen or a halogen;

m is zero or an integer in the range of 1 to 8; and n is an integer in the range of 1 to 8.

In certain certain embodiments, R$_2$ is absent, or represents a small hydrophobic group.

In certain embodiments, A represents a 5-membered heterocycle including the N and the Cα carbon.

In certain embodiments, W is —B(Y$_1$)(Y$_2$).

In certain embodiments, R$_2$ is absent or represents halogen or lower alkyl.

In certain embodiments, R$_4$ represents hydrogen or lower alkyl.

In certain embodiments, R$_5$ represents H or alkyl.

In certain embodiments, Y$_1$ and Y$_2$ are OH.

In certain embodiments, W is —B(OH)$_2$.

In certain embodiments, W is —B(OH)$_2$, and A represents a 5-membered heterocycle including the N and the Cα carbon.

In certain embodiments, W is —B(OH)$_2$, A represents a 5-membered heterocycle including the N and the Cα carbon, and R$_2$ is absent or represents halogen or lower alkyl.

In certain embodiments, W is —B(OH)$_2$, A represents a 5-membered heterocycle including the N and the Cα carbon, R$_2$ is absent or represents halogen or lower alkyl, and R$_4$ represents hydrogen or lower alkyl.

In other embodiments, W is —B(OH)$_2$, A represents a S-membered heterocycle including the N and the Cα carbon, R$_4$ represents hydrogen or lower alkyl, and R$_2$ is azido, cyano, isocyanato, thiocyanato, isothiocyanato, cyanato,

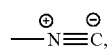

or

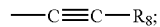

In certain embodiments, R$_1$ is one of the following:

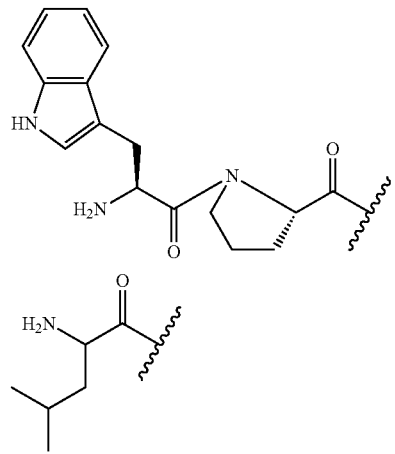

49
-continued

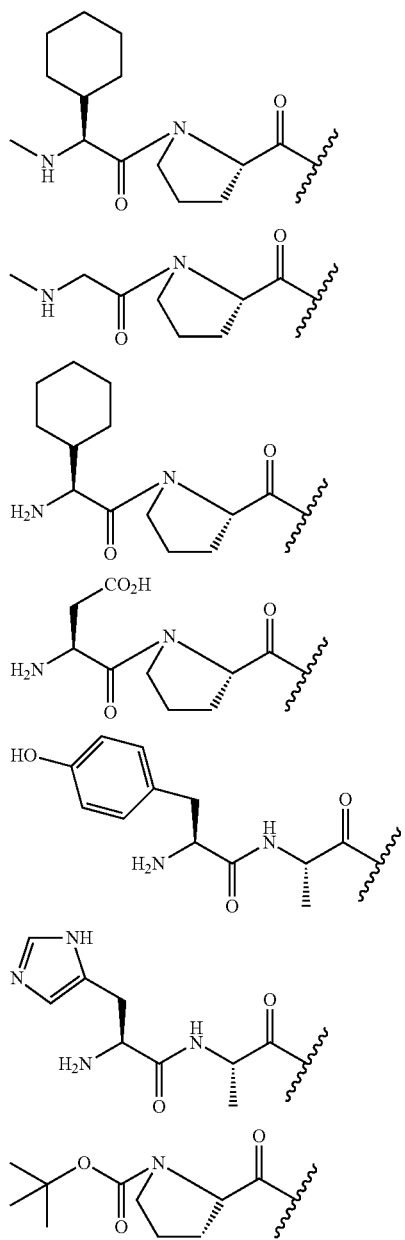

In certain embodiments, W is —B(OH)$_2$, A represents a 5-membered heterocycle including the N and the Cα carbon, R$_2$ is absent or represents halogen or lower alkyl, and R$_1$ is one of the following:

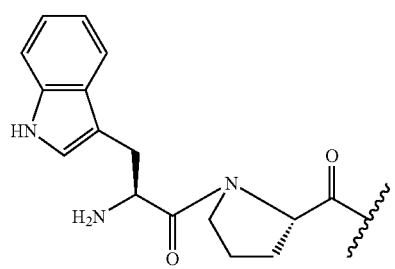

50
-continued

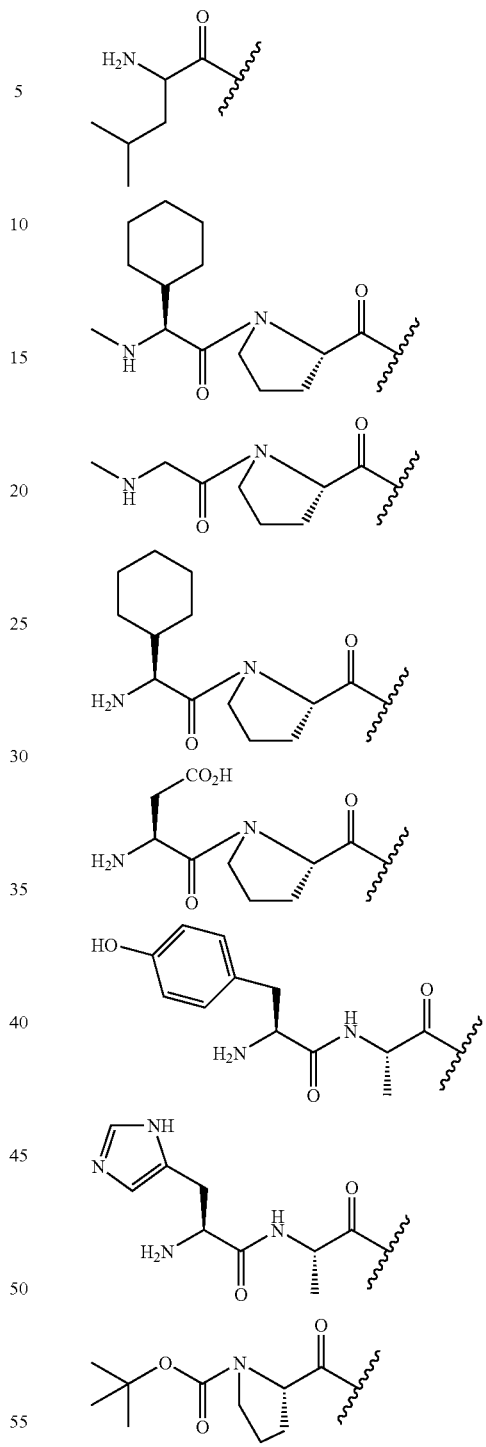

In other embodiments, W is —B(OH)$_2$, A represents a 5-membered heterocycle including the N and the Cα carbon, R$_4$ represents hydrogen or lower alkyl, and R$_2$ is azido, cyano, isocyanato, thiocyanato, isothiocyanato, cyanato,

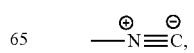

or

and R₁ is one of the following:

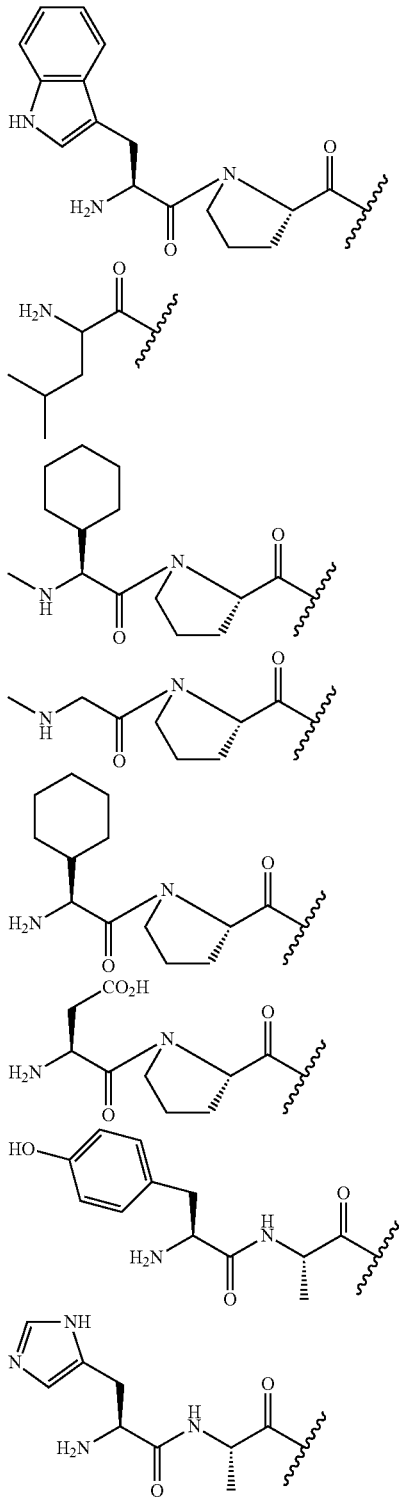

-continued

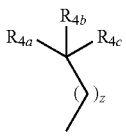

In certain embodiments, the compound is represented in the formula XVII:

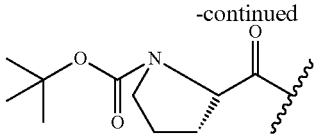

(XVII)

wherein $R_1$, $R_3$, $R_4$ and W are as defined above, and p is an integer from 1 to 3. In certain certain embodiments, p is 1, and $R_3$ is a hydrogen in each occurrence.

In certain certain embodiments of the compound structures above, W represents:

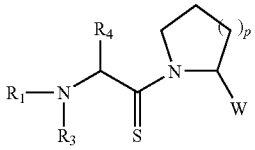

In certain certain embodiments of the compound structures above, $R_5$ is a hydrogen or $-C(X_1)(X_2)X_3$, wherein $X_1$ is a fluorine, and $X_2$ and $X_3$, if halogens, are also fluorine.

In certain certain embodiments of the compound structures above, $R_4$ is a lower alkyl. In certain certain embodiments of the compound structures above, $R_4$ represents a side chain of an amino acid residue selected from Gly, Ala, Val, Ser, Thr, Ile and Leu.

In certain certain embodiments of the compound structures above, $R_1$ is a peptidyl moiety which is a substrate for a post-proline cleaving enzyme.

In certain certain embodiments of the subject pro-soft inhibitor structures XVI and XVII, $R_4$ represents a side chain of an amino acid residue represented in the formula:

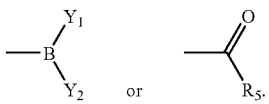

wherein $R_{4a}$ and $R_{4b}$ each independently represent a hydrogen, lower alkyl, heteroalkyl, cycloalkyl, heterocycloalkyl, aryl, heteroaryl, alkoxyl, carboxyl, carboxamide, carbonyl, or cyano, with the caveat that either both or neither of $R_{4a}$ and $R_{4b}$ are hydrogen;

$R_{4c}$ represents a halogen, an amine, an alkyl, heteroalkyl, cycloalkyl, heterocycloalkyl, aryl, heteroaryl, alkoxyl, carboxyl, carboxamide, carbonyl, or cyano; and z is zero or an integer in the range of 0 to 3.

In certain certain embodiments of structures XIV and XV, $R_4$ represents a side chain of an amino acid residue represented in the formula:

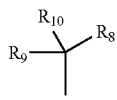

wherein: $R_8$ and $R_9$ each independently represent a lower alkyl or a halogen; $R_{10}$ represents a lower alkyl, an aryl, a hydroxyl group or —$(CH_2)$, —COOH. In certain certain embodiments, $R_8$ and $R_9$ each independently represents a lower alkyl, more preferably methyl, ethyl or propyl, and even more preferably a methyl. In certain certain embodiments, $R_{10}$ represents a lower alkyl, more preferably methyl, ethyl or propyl, and even more preferably a methyl. In other certain embodiments, $R_{10}$ represents an aryl, such as phenyl or hydroxyphenyl (preferably para-hydroxy). In yet other certain embodiments, $R_{10}$ represents a hydroxyl group. In certain certain embodiments, $R_{10}$ represents —$(CH_2)_m$—COOH, where m=0, 1 or 2, and preferably where m is 0 or 1.

In certain embodiments, the pro-soft inhibitor is activated by one protease and inhibits a different protease. For example, it can be activated by FAP and the resulting inhibitor G is selective for the proteasome. In certain embodiments of the compound structures above, $R_1$ is not an efficient substrate for the target protease. For instance, as a substrate, $R_1$ preferably has a turnover number as a substrate for the target protease of less than 1/second, and even more preferably less than 0.1/second, 0.001/second or even 0.0001/second.

In certain embodiments, A is a peptidyl moiety of 2 to 5 amino acid residues or the equivalents thereof. In certain embodiments, A is a dipeptidyl moiety, e.g., derived from naturally occurring amino acids or analogs thereof.

In certain embodiments, the backbone of the peptidyl moiety A can include one or more be a non-hydrolyzable analogs of a peptide bond, except for the bond linking A to G.

In certain certain embodiments, A is represented by:

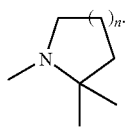

In certain embodiments of the present invention, compounds represented by the formula: A-G do not inhibit the selected target enzyme, or other enzymes to an appreciable extent. In certain embodiments of the present invention, the pro-soft inhibitor are themselves inactive, but become activated in the body when the R-A group is removed to liberate the enzyme inhibitory moiety G.

In certain embodiments, the present invention relates to the aforementioned compound, wherein $R_1$ is one of the following:

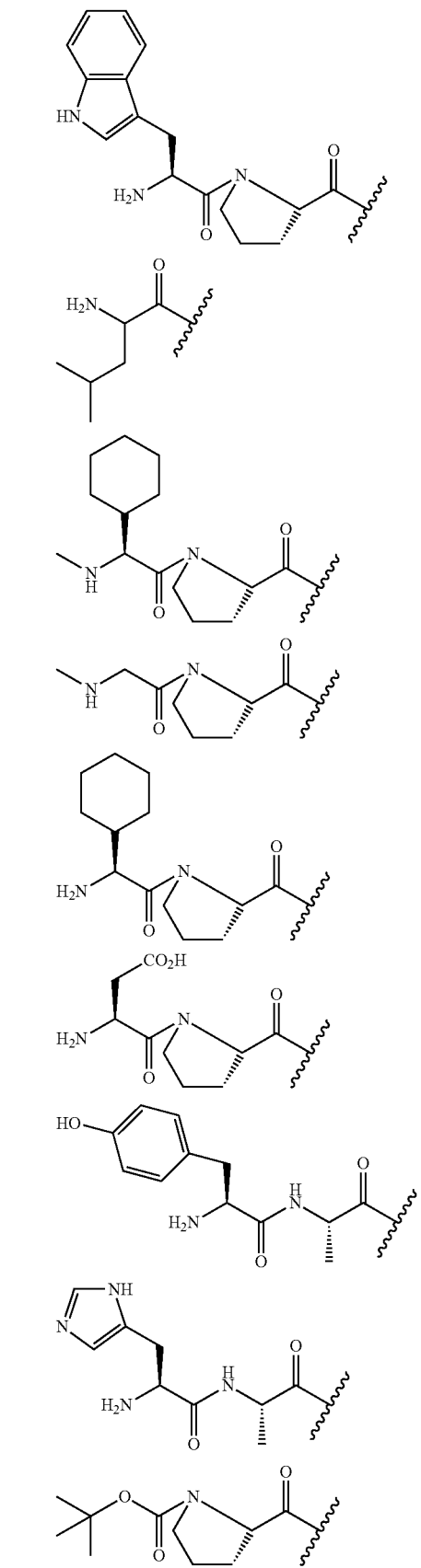

Embodiment D

A representative class of compounds for use in the method of the present invention are represented by formula XVIII:

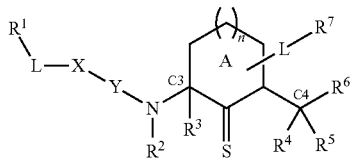

(XVIII)

or a pharmaceutically acceptable salt thereof, wherein:

$R^1$ represents H, alkyl, alkoxy, alkenyl, alkynyl, amino, alkylamino, acylamino, cyano, sulfonylamino, acyloxy, aryl, cycloalkyl, heterocyclyl, heteroaryl, or a polypeptide chain of 1 to 8 amino acid residues;

$R^2$ and $R^3$ each independently represent H, lower alkyl, and aralkyl, or $R^2$ and $R^3$ together with the atoms to which they are attached, form a 4- to 6-membered heterocyclic ring;

$R^4$ and $R^5$ each independently represent H, halogen, or alkyl, or $R^4$ and $R^5$, together with the carbon to which they are attached, form a 3- to 6-membered carbocyclic or heterocyclic ring;

$R^6$ represents a functional group that reacts with an active site residue of a targeted protease to form a covalent adduct;

$R^7$ is absent or represents one or more substituents on ring A, each of which is independently selected from H, lower alkyl, lower alkenyl, lower alkynyl, hydroxyl, oxo, ether, thioether, halogen, carbonyl, thiocarbonyl, amino, amido, cyano, nitro, azido, alkylamino, acylamino, aminoacyl, cyano, sulfate, sulfonate, sulfonyl, sulfonylamino, aminosulfonyl, alkoxycarbonyl, acyloxy, aryl, cycloalkyl, heterocyclyl, heteroaryl, or polypeptide chains of 1 to 8 amino acid residues;

$R^5$ represents H, aryl, alkyl, aralkyl, cycloalkyl, heterocyclyl, heteroaryl, heteroaralkyl, or a polypeptide chain of 1 to 8 amino acid residues;

L is absent or represents alkyl, alkenyl, alkynyl, $-(CH_2)_m-O-(CH_2)_m-$, $-(CH_2)_mNR_2(CH_2)_m-$, or $-(CH_2)_mS(CH_2)_m-$, X is absent or represents $-N(R^8)-$, $-O-$, or $-S-$;

Y is absent or represents $-C(=O)-$, $-C(=S)-$, or $-SO_2-$;

m is, independently for each occurrence, an integer from 0 to 10; and n is an integer from 0 to 3, preferably 0 or 1.

In certain certain embodiments, $R^1$ represents H or lower alkyl, $R^2$ and $R^3$ each independently represent H, lower alkyl, or aralkyl, or $R^2$ and $R^3$ together with the atoms to which they are attached, form a 5-membered heterocyclic ring, $R^4$ represents H or lower alkyl, and $R^5$ represents H.

In a further certain embodiment, the stereochemical designations at C3 and C4 are R and S respectively.

In certain other embodiments, $R^6$ represents cyano, boronic acid, $-SO_2Z^1$, $-P(=O)Z^1$, $-P(=R^9)R^{10}R^{11}$, $-C(=NH)NH_2$, $-CH-NR^{12}$, or $-C(=O)-R^{12}$, wherein:

$R^9$ represents O or S;

$R^{10}$ represents $N_3$, $SH_2$, $NH_2$, $NO_2$, or $OLR^{13}$, and $R^{11}$ represents lower alkyl, amino, $OLR^{13}$, or a pharmaceutically acceptable salt thereof, or $R^{10}$ and $R^{11}$, together with the phosphorus to which they are attached, form a 5- to 8-membered heterocyclic ring;

$R^{12}$ represents H, alkyl, alkenyl, alkynyl, $-(CH_2)_p-R^{13}$, $-(CH_2)_q-OH$, $-(CH_2)_q-O$-alkyl, $-(CH_2)_q-O$-alkenyl, $-(CH_2)_q-O$-alkynyl, $-(CH_2)_q-O-(CH_2)_p-R^{13}$, $-(CH_2)_q-SH$, $-(CH_2)_q-S$-alkyl, $-(CH_2)_q-S$-alkenyl, $-(CH_2)_q-S$-alkynyl, $-(CH_2)_q-S-(CH_2)_p-R^{13}$, $-C(O)C(O)NH_2$, $-C(O)C(O)OR^{14}$, or $-C(Z)(Z^2)(Z^3)$;

$R^{13}$ represents H, alkyl, alkenyl, aryl, cycloalkyl, cycloalkenyl, or heterocyclyl;

$R^{14}$ represents H, alkyl, alkenyl, or $LR^{13}$;

$Z^1$ represents a halogen;

$Z^2$ and $Z^3$ independently represent H or halogen;

p is, independently for each occurrence, an integer from 0 to 8; and q is, independently for each occurrence, an integer from 1 to 8.

In another embodiment, $R^6$ represents CN, CHO, or $C(=O)C(Z^1)(Z^2)(Z^3)$, wherein $Z^1$ represents a halogen, and $Z^2$ and $Z^3$ represent H or halogen. In certain such embodiments, $R^r$ represents $C(=O)C(Z^1)(Z^2)(Z^3)$, wherein $Z^1$ represents fluorine, and $Z^2$ and $Z^3$ represent H or fluorine.

In certain certain embodiments, $R^6$ is a group represented by $B(Y^1)(Y^2)$ wherein $Y^1$ and $Y^2$ are independently OH or a group that is hydrolysable to OH (i.e., to form a boronic acid), or together with the boron atom to which they are attached form a 5- to 8-membered ring that is hydrolysable to a boronic acid.

Embodiment E

A representative class of compounds for use in the method of the present invention are represented by formula XIX:

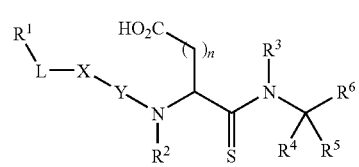

(XIX)

wherein $R^1$ represents H, alkyl, alkoxy, alkenyl, alkynyl, amino, alkylamino, acylamino, cyano, sulfonylamino, acyloxy, aryl, cycloalkyl, heterocyclyl, heteroaryl, or a polypeptide chain of 1 to 8 amino acid residues;

$R^2$ represents H, lower alkyl, or aralkyl;

$R^3$ and $R^4$ independently represent H, halogen, or alkyl, or $R^3$ and $R^4$ together with the atoms to which they are attached, form a 3- to 6-membered heterocyclic ring;

$R^5$ represents H, halogen, lower alkyl, or aralkyl;

$R^6$ represents a functional group that reacts with an active site residue of a targeted protease to form a covalent adduct;

$R^7$ represents H, aryl, alkyl, aralkyl, cycloalkyl, heterocyclyl, heteroaryl, heteroaralkyl, or polypeptide chains of 1 to 8 amino acid residues;

L is absent or represents alkyl, alkenyl, alkynyl, $-(CH_2)_m-O-(CH_2)_m-$, $-(CH_2)_mNR_2(CH_2)_m-$, and $-(CH_2)_mS(CH_2)_m-$;

X is absent or represents $-N(R^7)-$, $-O-$, or $-S-$;

Y is absent or represents $-C(=O)-$, $-C(=S)-$, or $-SO_2-$;

m is, independently for each occurrence, an integer from 0 to 10; and n is an integer from 1 to 6.

In certain certain embodiments, $R^1$ represents H or lower alkyl, $R^3$ and $R^4$ together with the atoms to which they are attached form a 5-membered ring, and n is 2.

In certain other certain embodiments $R^1$ represents H or lower alkyl, $R^3$ represents H, $R^4$ represents H or lower alkyl, $R^5$ represents H, and n is 2.

In certain certain embodiments, $R^1$ is a polypeptide chain of 2 to 8 amino acid residues, wherein proline is the residue that is directly attached. Most preferably $R^1$ is a polypeptide chain of 2 amino acid residues In certain above embodiments, $R^6$ represents cyano, boronic acid, $-SO_2Z^1$, $-P(=O)Z^1$, $-P(=R^8)R^9R^{10}$, $-C(=NH)NH_2$, $-CH=NR^{11}$, and $-C(=O)-R^{11}$, wherein $R^8$ represents O or S;

$R^9$ represents $N_3$, $SH_2$, $NH_2$, $NO_2$, and $OLR^{12}$, and $R^{10}$ represents lower alkyl, amino, $OLR^{12}$, or a pharmaceutically acceptable salt thereof, or $R^9$ and $R^{10}$, together with the phosphorus to which they are attached, form a 5- to 8-membered heterocyclic ring;

$R^{11}$ represents H, alkyl, alkenyl, alkynyl, $-(CH_2)_p-R^{12}$, $-(CH_2)_q-OH$, $-(CH_2)_q-O$-alkyl, $-(CH_2)_q-O$-alkenyl, $-(CH_2)_q-O$-alkynyl, $-(CH_2)_q-O-(CH_2)_p-R^2$, $-(CH_2)_q-SH$, $-(CH_2)_q-S$-alkyl, $-(CH_2)_q-S$-alkenyl, $-(CH_2)_q-S$-alkynyl, $-(CH_2)_q-S-(CH_2)_p-R^{12}$, $-C(O)C(O)NH_2$, $-C(O)C(O)OR^{13}$, or $-C(Z^1)(Z^2)(Z^3)$;

$R^{12}$ represents H, alkyl, alkenyl, aryl, cycloalkyl, cycloalkenyl, and heterocyclyl;

$R^{13}$ represents H, alkyl, alkenyl, and $LR^{12}$;

$Z^1$ represents a halogen;

$Z^2$ and $Z^3$ independently represent H or halogen;

p is, independently for each occurrence, an integer from 0 to 8; and q is, independently for each occurrence, an integer from 1 to 8.

In another embodiment, $R^6$ represents CN, CHO, or $C(=O)C(Z^1)(Z^2)(Z^3)$, wherein $Z^1$ represents a halogen, and $Z^2$ and $Z^3$ represent H or halogen. In certain such embodiments, $R^6$ represents $C(=O)C(Z^1)(Z^2)(Z^3)$, wherein $Z^1$ represents fluorine, and $Z^2$ and $Z^3$ represent H or fluorine.

In certain certain embodiments, $R^6$ represents a group $-B(Y^1)(Y^2)$, wherein Yt and $Y^2$ are independently OH or a group that is hydrolysable to OH (i.e., thereby forming a boronic acid), or together with the boron atom to which they are attached form a 5- to 8-membered ring that is hydrolysable to a boronic acid.

In certain certain embodiments, $R^3$ and $R^4$ together with the atoms to which they are attached form a 5-membered ring, which is substituted with one or more groups selected from hydroxyl, lower alkyl (e.g., methyl), lower alkenyl, lower alkynyl, lower alkoxy, lower hydroxyalkyl (e.g., hydroxymethyl), and lower alkoxyalkyl.

In more certain embodiments, the substituent group is selected from the group consisting of lower alkyl, lower hydroxyalkyl and lower alkoxyalkyl. In more preferred such embodiments, the substituent group is located at the 5-position of the ring.

In other more certain embodiments, the substituent group is hydroxyl, which is preferably located at the 4-position of the ring.

In certain embodiments, the substituent group on the 5-membered ring containing $R^3$ and $R^4$ is selected from the group consisting of lower alkyl (e.g., methyl), hydroxyl, lower hydroxyalkyl (e.g., hydroxymethyl) and lower alkoxyalkyl. In certain preferred such embodiments, the substituent group has a cis-stereochemical relationship to $R^6$. Such stereochemical relationships are particularly advantageous for compounds having substituents at the 4- or 5-position of the 5-membered ring, as discussed immediately above.

In certain embodiments of the invention, a subject compound has a structure of Formula XX:

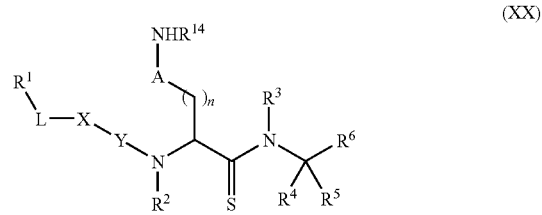

(XX)

or a pharmaceutically acceptable salt thereof, where:

$R^1$ represents H, alkyl, alkoxy, alkenyl, alkynyl, amino, alkylamino, acylamino, cyano, sulfonylamino, acyloxy, aryl, cycloalkyl, heterocyclyl, heteroaryl, or a polypeptide chain of 1 to 8 amino acid residues;

$R^2$ represents H, lower alkyl, or aralkyl;

$R^3$ and $R^4$ independently represent H, halogen, or alkyl, or $R^3$ and $R^4$ together with the carbon to which they are attached, form a 3- to 6-membered heterocyclic ring;

$R^5$ represents H, halogen, lower alkyl, or aralkyl, preferably H or lower alkyl;

$R^6$ represents a functional group that reacts with an active site residue of the targeted protease to form a covalent adduct;

$R^7$ represents H, aryl, alkyl, aralkyl, cycloalkyl, heterocyclyl, heteroaryl, heteroaralkyl, or a polypeptide chain of 1 to 8 amino acid residues;

$R^{14}$ represents H, alkyl, alkoxy, alkenyl, alkynyl, or aralkyl, preferably H;

A is absent or represents $-NHC(=NH)-$, or $R^{14}$ and A together with the nitrogen to which they are attached form a heterocyclic ring;

L is absent or represents alkyl, alkenyl, alkynyl, $(CH_2)_m-O-(CH_2)_m-$, $-(CH_2)_mNR_2(CH_2)_m-$, and $-(CH_2)_mS(CH_2)_m-$;

X is absent or represents $-N(R^7)-$, $-O-$, or $-S-$;

Y is absent or represents $-C(=O)-$, $-C(=S)-$, or $-SO_2-$;

m is, independently for each occurrence, an integer from 0 to 10; and n is an integer from 1 to 6.

In certain certain embodiments, $R^1$ represents H or lower alkyl, $R^3$ and $R^4$ together with the carbon to which they are attached form a 5-membered ring, and n is an integer from 1 to 4.

In certain certain embodiments, $R^{14}$ is H, A is absent, and n is 4. In certain other embodiments, $R^{14}$ is H, A is $-NHC(=NH)-$, and n is 3.

In certain certain embodiments, A and $R^{14}$ together with the nitrogen to which they are attached form an imidazole ring, and n is 1.

In certain embodiments, $R^6$ represents boronic acid, CN, $-SO_2Z^1$, $-P(=O)Z^1$, $-P(=R^8)R^9R^{10}$, $-C(=NH)NH_2$, $-CH=NR^{11}$, or $-C(=O)-R^{11}$ wherein $R^8$ is O or S;

$R^9$ represents $N_3$, $SH_2$, $NH_2$, $NO_2$, or $OLR^{12}$, and $R^{10}$ represents lower alkyl, amino, $OLR^2$, or a pharmaceutically acceptable salt thereof, or $R^9$ and $R^{10}$, together with the phosphorus to which they are attached, form a 5- to 8-membered heterocyclic ring;

$R^{11}$ represents H, alkyl, alkenyl, alkynyl, $NH_2$, $-(CH_2)_p-R^2$, $-(CH_2)_q-OH$, $-(CH_2)_q-O$-alkyl, $-(CH_2)_q-O$-alkenyl, $-(CH_2)_q-O$-alkynyl, $-(CH_2)_q-O-(CH_2)_p-R^{12}$, $-(CH_2)_q-SH$, $-(CH_2)_q-S$-alkyl, —(CH$_2$)$_q$—S-alkenyl, —(CH$_2$)$_q$—S-alkynyl, —(CH$_2$)$_q$—S—(CH$_2$)$_p$—R$^{12}$, —C(O)NH$_2$, —C(O)OR$^{13}$, or C(Z$^1$)(Z$^2$)(Z$^3$);

R$^{12}$ represents H, alkyl, alkenyl, aryl, heteroaryl, cycloalkyl, cycloalkenyl, or heterocyclyl;

R$^{13}$ represents H, alkyl, alkenyl, or LR$^{12}$;

Z$^1$ represents a halogen;

Z$^2$ and Z$^3$ independently represent H or halogen;

p is, independently for each occurrence, an integer from 0 to 8; and q is, independently for each occurrence, an integer from 1 to 8.

In certain certain embodiments, R$^6$ represents CN, CHO, or C(=O)C(Z$^1$)(Z$^2$)(Z$^3$), wherein Z$^1$ represents a halogen, and Z$^2$ and Z$^3$ represent H or halogen. In another embodiment, R$^6$ represents C(=O)C(Z$^1$)(Z$^2$)(Z$^3$), wherein Z$^1$ represents fluorine, and Z$^2$ and Z$^3$ represent H or fluorine.

In certain certain embodiments, R$^6$ represents a group —B(Y$^1$)(Y$^2$), wherein Y$^1$ and Y$^2$ are independently OH or a group that is hydrolysable to OH, or together with the boron atom to which they are attached form a 5- to 8-membered ring that is hydrolysable to a boronic acid.

In certain certain embodiments, R$^3$ and R$^4$ together with the atoms to which they are attached form a 5-membered ring, which is substituted with one or more groups selected from hydroxyl, lower alkyl (e.g., methyl), lower alkenyl, lower alkynyl, lower alkoxy, lower hydroxyalkyl (e.g., hydroxymethyl), and lower alkoxyalkyl.

In more certain embodiments, the substituent group is selected from the group consisting of lower alkyl, lower hydroxyalkyl and lower alkoxyalkyl. In more preferred such embodiments, the substituent group is located at the 5-position of the ring.

In other more certain embodiments, the substituent group is hydroxyl, which is preferably located at the 4-position of the ring.

In certain embodiments, the substituent group on the 5-membered ring containing R$^3$ and R$^4$ is selected from the group consisting of lower alkyl (e.g., methyl), hydroxyl, lower hydroxyalkyl (e.g., hydroxymethyl) and lower alkoxyalkyl. In certain preferred such embodiments, the substituent group has a cis-stereochemical relationship to R$^6$. Such stereochemical relationships are particularly advantageous for compounds having substituents at the 4- or 5-position of the 5-membered ring, as discussed immediately above.

In certain embodiments of the invention, a subject compound has a structure of Formula XXI:

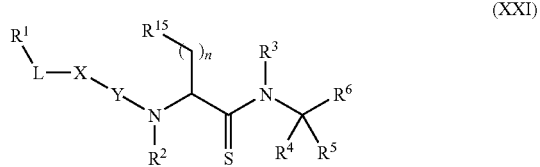

(XXI)

or a pharmaceutically acceptable salt thereof, where:

R$^1$ represents H, alkyl, alkoxy, alkenyl, alkynyl, amino, alkylamino, acylamino, cyano, sulfonylamino, acyloxy, aryl, cycloalkyl, heterocyclyl, heteroaryl, or a polypeptide chain of 1 to 8 amino acid residues;

R$^2$ represents H, lower alkyl, or aralkyl;

R$^3$ and R$^4$ independently represent H, halogen, or alkyl, or R$^3$ and R$^4$ together with the carbon to which they are attached, form a 3- to 6-membered heterocyclic ring;

R$^5$ represents H, halogen, lower alkyl, or aralkyl, preferably H or lower alkyl;

R$^6$ represents a functional group that reacts with an active site residue of a targeted protease to form a covalent adduct;

R$^7$ represents H, aryl, alkyl, aralkyl, cycloalkyl, heterocyclyl, heteroaryl, heteroaralkyl, or a polypeptide chain of 1 to 8 amino acid residues;

R$^{15}$ is a functional group that has either a positive or negative charge at physiological pH, preferably an amine or carboxylic acid;

L is absent or represents alkyl, alkenyl, alkynyl, —(CH$_2$)$_m$—O—(CH$_2$)$_m$—, —(CH$_2$)$_m$NR$_2$(CH$_2$)$_m$—, and —(CH$_2$)$_m$S(CH$_2$)$_m$—;

X is absent or represents —N(R$^7$)—, —O—, or —S—;

Y is absent or represents —C(=O)—, —C(=S)—, or —SO$_2$—;

m is, independently for each occurrence, an integer from 0 to 10; and n is an integer from 1 to 6.

In certain certain embodiments, R$^1$ represents H or lower alkyl, R$^3$ is H and R$^4$ is lower alkyl, or R$^3$ and R$^4$ together with the carbon to which they are attached form a 5-membered ring, and n is an integer from 1 to 4.

In certain certain embodiments, n is an integer from 1 to 4 and R$^{15}$ is a functional group that has either a positive or negative charge at physiological pH. In more certain embodiments n is an integer from 1 to 4 and R's is selected from the group consisting of amine, carboxylic acid, imidazole, or guanidine functionality.

In certain embodiments, R$^6$ represents boronic acid, CN, —SO$_2$Z$^1$, —P(=O)Z$^1$, —P(=R$^8$)R$^9$R$^{10}$, —C(=NH)NH$_2$, —CH=NR$^{11}$, or —C(=O)—R$^{11}$ wherein R$^8$ is O or S;

R$^9$ represents N$_3$, SH$_2$, NH$_2$, NO$_2$, or OLR$^2$, and

R$^{10}$ represents lower alkyl, amino, OLR$^2$, or a pharmaceutically acceptable salt thereof, or R$^9$ and R$^{10}$, together with the phosphorus to which they are attached, form a 5- to 8-membered heterocyclic ring;

R$^{11}$ represents H, alkyl, alkenyl, alkynyl, NH$_2$, —(CH$_2$)$_n$—R$^{12}$, —(CH$_2$)$_q$—OH, —(CH$_2$)$_q$—O-alkyl, —(CH$_2$)$_q$—O-alkenyl, —(CH$_2$)$_q$—O-alkynyl, —(CH$_2$)$_q$—O—(CH$_2$)$_p$—R$^2$, —(CH$_2$)$_q$—SH, —(CH$_2$)$_q$—S-alkyl, —(CH$_2$)$_q$—S-alkenyl, —(CH$_2$)$_q$—S-alkynyl, —(CH$_2$)$_q$—S—(CH$_2$)$_p$—R$^{12}$, —C(O)NH$_2$, —C(O)OR$^{13}$, or —C(Z$^1$)(Z$^2$)(Z$^3$);

R$^{12}$ represents H, alkyl, alkenyl, aryl, heteroaryl, cycloalkyl, cycloalkenyl, or heterocyclyl;

R$^{13}$ represents H, alkyl, alkenyl, or LR$^{12}$;

Z$^1$ represents a halogen;

Z$^2$ and Z$^3$ independently represent H or halogen;

p is, independently for each occurrence, an integer from 0 to 8; and q is, independently for each occurrence, an integer from 1 to 8.

In certain certain embodiments, R$^6$ represents CN, CHO, or C(=O)C(Z$^1$)(Z$^2$)(Z$^3$), wherein Z$^1$ represents a halogen, and Z$^2$ and Z$^3$ represent H or halogen. In another embodiment, R$^6$ represents C(=O)C(Z$^1$)(Z$^2$)(Z$^3$), wherein Z$^1$ represents fluorine, and Z$^2$ and Z$^3$ represent H or fluorine.

In certain certain embodiments, R$^6$ represents a group —B(Y$^1$)(Y$^2$), wherein Y$^1$ and Y$^2$ are independently OH or a group that is hydrolysable to OH, or together with the boron atom to which they are attached form a 5- to 8-membered ring that is hydrolysable to a boronic acid.

In certain certain embodiments, R$^3$ and R$^4$ together with the atoms to which they are attached form a 5-membered ring substituted with one or more groups selected from hydroxyl, lower alkyl (e.g., methyl), lower alkenyl, lower alkynyl, lower alkoxy, lower hydroxyalkyl (e.g., hydroxymethyl), and lower alkoxyalkyl.

In more certain embodiments, the substituent group is selected from the group consisting of lower alkyl, lower hydroxyalkyl and lower alkoxyalkyl. In more preferred such embodiments, the substituent group is located at the 5-position of the ring.

In other more certain embodiments, the substituent group is hydroxyl, which is preferably located at the 4-position of the ring.

In certain embodiments, the substituent group on the 5-membered ring containing $R^3$ and $R^4$ is selected from the group consisting of lower alkyl (e.g., methyl), hydroxyl, lower hydroxyalkyl (e.g., hydroxymethyl) and lower alkoxyalkyl. In certain preferred such embodiments, the substituent group has a cis-stereochemical relationship to $R^6$. Such stereochemical relationships are particularly advantageous for compounds having substituents at the 4- or 5-position of the 5-membered ring, as discussed immediately above.

Another aspect of the invention relates to inhibitors having a structure of Formula XXII:

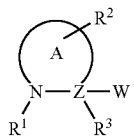

(XXII)

or a pharmaceutically acceptable salt thereof, wherein

A is selected from the group consisting of a 4-8 membered heterocycle including the N and a Cα carbon;

Z is C or N;

W is selected from the group consisting of CN, —CH=NR$^{15}$, a functional group which reacts with an active site residue of the targeted protease,

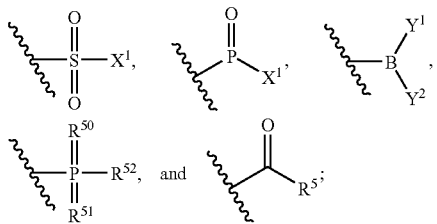

$R^1$ is selected from the group consisting of a C-terminally linked amino acid residue or amino acid analog, a C-terminally linked peptide or peptide analog, or

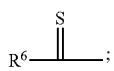

wherein the bond between $R^1$ and N is a thioamide bond;

$R^2$ represents one or more substitutions to the ring A, each of which is independently a halogen, lower alkyl, lower alkenyl, lower alkynyl, carbonyl, carboxyl, ester, formate, ketone, thiocarbonyl, thioester, thioacetate, thioformate, amino, acylamino, amido, nitro, sulfate, sulfonate, sulfonamido, —(CH$_2$)$_m$—R$^7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$^7$, —(CH$_2$)$_m$—SH, —(CH$_2$)$_m$—S-lower alkyl, —(CH$_2$)$_m$—S-lower alkenyl, or —(CH$_2$)$_n$—S—(CH$_2$)$_m$—R$^7$, azido, cyano, isocyanato, thiocyanato, isothiocyanato, cyanato,

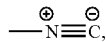

or

wherein at least one $R^2$ is selected from the group consisting of —OH, lower alkyl, lower alkoxy, lower hydroxyalkyl, and lower alkoxyalkyl, preferably at least one of lower alkyl (e.g., methyl), lower alkoxy, lower hydroxyalkyl (e.g., hydroxymethyl), and lower alkoxyalkyl;

when Z is N, $R^3$ is absent;

when Z is C, $R^3$ is selected from the group consisting of hydrogen, halogen, lower alkyl, lower alkenyl, lower alkynyl, carbonyl, thiocarbonyl, amino, acylamino, amido, cyano, nitro, azido, sulfate, sulfonate, sulfonamido, —(CH$_2$)$_m$—R$^7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$^7$, (CH$_2$)$_m$—SH, —(CH$_2$)$_m$—S-lower alkyl, —(CH$_2$)$_n$—S-lower alkenyl, and —(CH$_2$)$_n$—S—(CH$_2$)$_m$—R$^7$;

$R^5$ is selected from the group consisting of hydrogen, alkyl, alkenyl, alkynyl, —C(X$^1$)(X$^2$)X$^3$, (CH$_2$)$_m$—R$^7$, —(CH$_2$)$_n$—OH, —(CH$_2$)$_n$—O-alkyl, (CH$_2$)$_n$—O-alkenyl, —(CH$_2$)$_n$—O-alkynyl, —(CH$_2$)$_n$—O—(CH$_2$)$_m$—R$^7$, —(CH$_2$)$_n$—SH, —(CH$_2$)$_n$—S-alkyl, —(CH$_2$)$_n$—S-alkenyl, —(CH$_2$)$_n$—S-alkynyl, —(CH$_2$)$_n$—S—(CH$_2$)$_m$—R$^7$, —C(O)C(O)NH$_2$, and —C(O)C(O)OR$^7$;

$R^6$ is selected from the group consisting of hydrogen, halogen, alkyl, alkenyl, alkynyl, aryl, —(CH$_2$)$_m$—R$^7$—(CH$_2$)$_m$—OH, —(CH$_2$)$_m$—O-alkyl, —(CH$_2$)$_m$—O-alkenyl, —(CH$_2$)$_m$—O-alkynyl, —(CH$_2$)$_m$—O—(H$_2$)$_m$—R$^7$, —(CH$_2$)$_m$—SH, —(CH$_2$)$_m$—S-alkyl, —(CH$_2$)$_m$—S-alkenyl, —(CH$_2$)$_m$—S-alkynyl, —(CH$_2$)$_m$—S—(CH$_2$)$_m$—R$^7$,

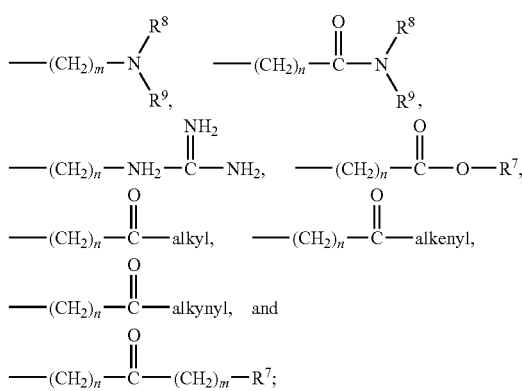

each $R^7$ is independently selected from aryl, aralkyl, cycloalkyl, cycloalkenyl, and heterocyclyl;

each $R^{7'}$ is independently selected from hydrogen, alkyl, alkenyl, aryl, aralkyl, cycloalkyl, cycloalkenyl and heterocyclyl;

$R^8$ and $R^9$ are each independently selected from hydrogen, alkyl, alkenyl, —(CH$_2$)$_m$—R$^7$, —C(═O)-alkyl, —C(═O)-alkenyl, —C(═O)-alkynyl, and —C(═O)—(CH$_2$)$_m$—R$^7$; or $R^8$ and $R^9$ taken together with the N atom to which they are attached complete a heterocyclic ring having from 4 to 8 atoms in the ring structure;

$R^{10}$ represents hydrogen, —CH$_3$, or —(CH$_2$)$_n$—CH$_3$;

$R^{50}$ is O or S;

$R^{51}$ is selected from the group consisting of N$_3$, SH, NH$_2$, NO$_2$, and OR$^7$;

$R^{52}$ is selected from the group consisting of hydrogen, lower alkyl, amine, OR$^7$, or a pharmaceutically acceptable salt thereof, or $R^{51}$ and $R^{52}$ taken together with the P atom to which they are attached complete a heterocyclic ring having from 5 to 8 atoms in the ring structure;

$X^1$ is a halogen;

$X^2$ and $X^3$ are each selected from hydrogen and halogen;

$Y^1$ and $Y^2$ are each independently selected from OH and a group capable of being hydrolyzed to OH, including cyclic derivatives where $Y^1$ and $Y^2$ are connected via a ring having from 5 to 8 atoms in the ring structure;

m is zero or an integer in the range of 1 to 8; and n is an integer in the range of 1 to 8.

In certain embodiments, W is selected from the group consisting of CN and B(Y$^1$)(Y$^2$). In certain certain embodiments, A is a five-membered ring, Z is C, and W is B(Y$^1$)(Y$^2$). In more certain embodiments, Z has the absolute stereochemical configuration of L-proline.

In certain embodiments, A is a five-membered ring, Z is C, and $R^2$ is selected from the group consisting of hydroxyl, lower alkyl, lower alkenyl, lower alkynyl, lower alkoxy, lower hydroxyalkyl, and lower alkoxyalkyl. In certain preferred such embodiments, $R^2$ is selected from the group consisting of lower hydroxyalkyl and lower alkoxyalkyl. In more preferred such embodiments, $R^2$ is located at the 5-position of the ring.

In certain embodiments, A is a five-membered ring, Z is C, and $R^2$ is selected from the group consisting of hydroxyl, lower alkyl (such as methyl), lower hydroxyalkyl (such as hydroxymethyl) and lower alkoxyalkyl. In certain preferred such embodiments, Z has the absolute stereochemical configuration of L-proline and $R^2$ is located at the 5-position of the ring for lower alkyl, lower hydroxyalkyl and lower alkoxyalkyl and at the 4-position for hydroxyl. In more preferred such embodiments, $R^2$ has a cis-stereochemical relationship to W.

Another aspect of the invention relates to inhibitors having a structure of Formula XXIII:

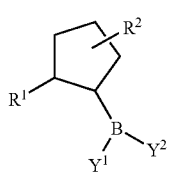

(XXIII)

or a pharmaceutically acceptable salt thereof, wherein $R^1$ is selected from the group consisting of a C-terminally linked amino acid residue or amino acid analog, a C-terminally linked peptide or peptide analog, or

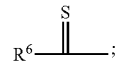

wherein the bond between $R^1$ and N is a thioxamide bond;

$R^2$ represents one or more substitutions to the ring A, each of which is independently a halogen, lower alkyl, lower alkenyl, lower alkynyl, carbonyl (such as a carboxyl, ester, formate, or ketone), thiocarbonyl (such as a thioester, thioacetate, or thioformate), amino, acylamino, amido, nitro, sulfate, sulfonate, sulfonamido, —(CH$_2$)$_m$—R$^7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$^7$, —(CH$_2$)$_m$—SH, —(CH$_2$)$_m$—S-lower alkyl, —(CH$_2$)$_m$—S-lower alkenyl, or —(CH$_2$)$_n$—S—(CH$_2$)$_m$—R$^7$ azido, cyano, isocyanato, thiocyanato, isothiocyanato, cyanato,

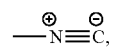

or

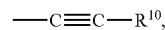

wherein at least one $R^2$ is selected from the group consisting of —OH, lower alkyl, lower alkoxy, lower hydroxyalkyl, and lower alkoxyalkyl, preferably at least one of lower alkyl (e.g., methyl), lower alkoxy, lower hydroxyalkyl (e.g., hydroxymethyl), and lower alkoxyalkyl;

$R^6$ is selected from the group consisting of hydrogen, halogen, alkyl, alkenyl, alkynyl, aryl, —(CH$_2$)$_m$—R$^7$, —(CH$_2$)$_m$—OH, —(CH$_2$)$_n$—O-alkyl, —(CH$_2$)$_m$—O-alkenyl, —(CH$_2$)$_m$—O-alkynyl, —(CH$_2$)$_m$—O—(CH$_2$)$_m$—R$^7$, —(CH$_2$)$_m$—SH, —(CH$_2$)$_m$—S-alkyl, —(CH$_2$)$_m$—S-alkenyl, —(CH$_2$)$_m$—S-alkynyl, —(CH$_2$)$_m$—S—(CH$_2$)$_m$—R$^7$,

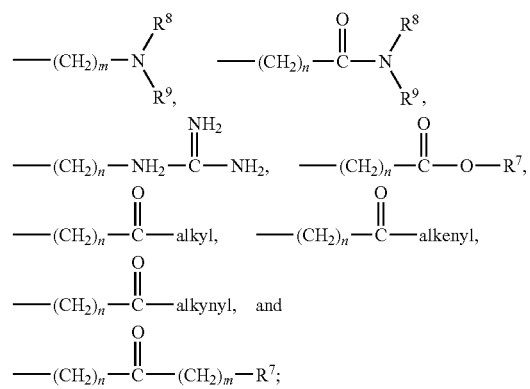

$R^7$ is selected from the group consisting of aryl, cycloalkyl, cycloalkenyl, and heterocyclyl;

$R^8$ and $R^9$ are each independently selected from hydrogen, alkyl, alkenyl, —(CH$_2$)$_m$—R$^7$, —C(═O)-alkyl, —C(═O)-alkenyl, —C(═O)-alkynyl, and —C(═O)—(CH$_2$)$_m$—R$^7$;

or $R^8$ and $R^9$ taken together with the N atom to which they are attached complete a heterocyclic ring having from 4 to 8 atoms in the ring structure;

$R^{10}$ represents hydrogen, —CH$_3$, or —(CH$_2$)$_n$—CH$_3$;

$Y^1$ and $Y^2$ are each independently selected from OH and a group capable of being hydrolyzed to OH, including cyclic derivatives where $Y^1$ and $Y^2$ are connected via a ring having from 5 to 8 atoms in the ring structure;

m is zero or an integer in the range of 1 to 8; and n is an integer in the range of 1 to 8.

In certain embodiments, the carbon bearing $B(Y^1)(Y^2)$ has the absolute stereochemical configuration of L-proline. In certain preferred such embodiments, $R^2$ is selected from the group consisting of hydroxyl, lower alkyl, lower hydroxyalkyl and lower alkoxyalkyl. In more preferred such embodiments, $R^2$ is located at the 5-position of the ring for lower alkyl (such as methyl), lower hydroxyalkyl (such as hydroxymethyl) and lower alkoxyalkyl or at the 4-position for hydroxyl. In most preferred such embodiments, $R^2$ has a cis-stereochemical relationship to $B(Y^1)(Y^2)$.

Another aspect of the invention relates to compounds having a structure of Formula XXIV:

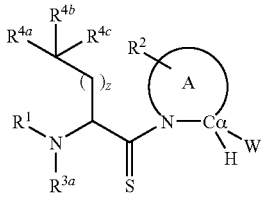

(XXIV)

or a pharmaceutically acceptable salt thereof, wherein

A is a 3-8 membered heterocycle including the N and the Cα carbon;

W is a functional group which reacts with an active site residue of a targeted protease to form a covalent adduct;

$R^1$ is selected from the group consisting of hydrogen, a C-terminally linked amino acid or peptide or analog thereof, and an amino protecting group; wherein optionally where applicable the bond between $R^1$ and the N to which it is attached is a thioamide bond;

$R^2$ represents one or more substitutions to the ring A, each of which is independently a halogen, lower alkyl, lower alkenyl, lower alkynyl, carbonyl (such as a carboxyl, ester, formate, or ketone), thiocarbonyl (such as a thioester, thioacetate, or thioformate), amino, acylamino, amido, nitro, sulfate, sulfonate, sulfonamido, $-(CH_2)_m-R^7$, $-(CH_2)_m-$OH, $-(CH_2)_m-$O-lower alkyl, $-(CH_2)_m-$O-lower alkenyl, $-(CH_2)_n-$O$-(CH_2)_m-R^7$, $-(CH_2)_m-$SH, $-(CH_2)_m-$S-lower alkyl, $-(CH_2)_m-$S-lower alkenyl, or $-(CH_2)_n-$S$-(CH_2)_m-R^7$, azido, cyano, isocyanato, thiocyanato, isothiocyanato, cyanato,

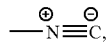

or

wherein at least one $R^2$ is selected from the group consisting of —OH, lower alkyl, lower alkoxy, lower hydroxyalkyl, and lower alkoxyalkyl, preferably at least one of lower alkyl (e.g., methyl), lower alkoxy, lower hydroxyalkyl (e.g., hydroxymethyl), and lower alkoxyalkyl;

$R^{3a}$ is selected from the group consisting of hydrogen and a substituent which does not conjugate the electron pair of the nitrogen from which it pends;

$R^{4a}$ and $R^{4b}$ are each independently selected from hydrogen, lower alkyl, heteroalkyl, cycloalkyl, heterocycloalkyl, aryl, heteroaryl, alkoxyl, carboxyl, carboxamide, carbonyl, and cyano, provided that either both or neither of $R^{4a}$ and $R^{4b}$ are hydrogen;

$R^{4c}$ is selected from the group consisting of halogen, amine, alkyl, heteroalkyl, cycloalkyl, heterocycloalkyl, aryl, heteroaryl, alkoxyl, carboxyl, carboxamide, carbonyl, and cyano;

each $R^6$ is independently selected from aryl, aralkyl, cycloalkyl, cycloalkenyl, and heterocyclyl;

z is zero or an integer in the range of 1 to 3;

m is zero or an integer in the range of 1 to 8; and n is an integer in the range of 1 to 8.

In certain embodiments, W is selected from the group consisting of CN and $B(Y^1)(Y^2)$, wherein $Y^1$ and $Y^2$ are each independently or OH, or a group capable of being hydrolyzed to OH, including cyclic derivatives where $Y^1$ and $Y^2$ are connected via a ring having from 5 to 8 atoms in the ring structure. In certain certain embodiments, A is a five-membered ring, and W is $B(Y^1)(Y^2)$. In more certain embodiments, Cα has the absolute stereochemical configuration of L-proline.

In certain embodiments, A is a five-membered ring and $R^2$ is selected from the group consisting of hydroxyl, lower alkyl, lower alkenyl, lower alkynyl, lower alkoxy, lower hydroxyalkyl, and lower alkoxyalkyl. In certain preferred such embodiments, $R^2$ is selected from the group consisting of lower alkyl (such as methyl), lower hydroxyalkyl (such as hydroxymethyl) and lower alkoxyalkyl. In more preferred such embodiments, $R^2$ is located at the 5-position of the ring.

In certain embodiments, A is a five-membered ring, and $R^2$ is selected from the group consisting of hydroxyl, hydroxyl, lower alkyl, lower hydroxyalkyl and lower alkoxyalkyl. In certain preferred such embodiments, Cα has the absolute stereochemical configuration of L-proline and $R^2$ is located at the 5-position of the ring for lower alkyl (such as methyl), lower hydroxyalkyl (such as hydroxymethyl) and lower alkoxyalkyl or at the 4-position for hydroxyl. In more preferred such embodiments, $R^2$ has a cis-stereochemical relationship to W.

Another aspect of the invention relates to compounds having a structure of Formula XXV:

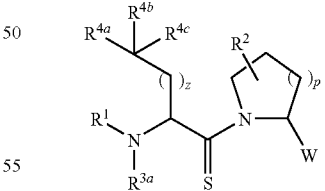

(XXV)

or a pharmaceutically acceptable salt thereof, wherein $R^1$, $R^2$, $R^{3a}$, $R^{4a}$, $R^{4b}$, $R^{4c}$ and W are as defined above for Formula XXIV, and p is an integer from 1 to 3. In certain certain embodiments, p is 1 and $R^{3a}$ is hydrogen.

In certain embodiments, W is selected from the group consisting of CN and $B(Y^1)(Y^2)$, wherein $Y^1$ and $Y^2$ are each independently or OH, or a group capable of being hydrolyzed to OH, including cyclic derivatives where $Y^1$ and $Y^2$ are connected via a ring having from 5 to 8 atoms in the ring structure. In certain certain embodiments, W is $B(Y^1)(Y^2)$. In more certain embodiments, the carbon bearing W has the absolute stereochemical configuration of L-proline.

In certain embodiments, $R^2$ is selected from the group consisting of hydroxyl, lower alkyl, lower alkenyl, lower alkynyl, lower alkoxy, lower hydroxyalkyl, and lower alkoxyalkyl. In certain certain embodiments, $R^2$ is selected from the group consisting of lower hydroxyalkyl (such as hydroxymethyl) and lower alkoxyalkyl. In more preferred such embodiments, p is 1 and $R^2$ is located at the 5-position of the ring.

In certain embodiments, $R^2$ is selected from the group consisting of hydroxyl, lower alkyl, lower hydroxyalkyl and lower alkoxyalkyl. In certain preferred such embodiments, p is 1, the carbon bearing W has the absolute stereochemical configuration of L-proline and $R^2$ is located at the 5-position of the ring for lower alkyl (such as methyl), lower hydroxyalkyl (such as hydroxymethyl) and lower alkoxyalkyl or at the 4-position for hydroxyl. In more preferred such embodiments, $R^2$ has a cis-stereochemical relationship to W.

In certain embodiments, $R^2$ is azido, cyano, isocyanato, thiocyanato, isothiocyanato, cyanato,

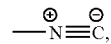

or

In certain certain embodiments, p is 1, the carbon bearing W has the absolute stereochemical configuration of L-proline and $R^2$ is located at the 5-position of the ring.

Yet another aspect of the present invention relates to a compound having a structure of Formula XXVI:

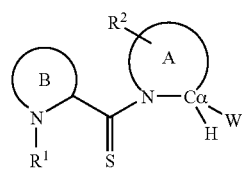

(XXVI)

or a pharmaceutically acceptable salt thereof, wherein

A is a 3 to 8-membered heterocycle including the N and the Cα carbon;

B is a $C_{3-8}$ ring, or $C_{7-14}$ fused bicyclic or tricyclic ring system;

W is a functional group which reacts with an active site residue of a targeted protease to form a covalent adduct, as for example, —CN, —CH═$NR^5$,

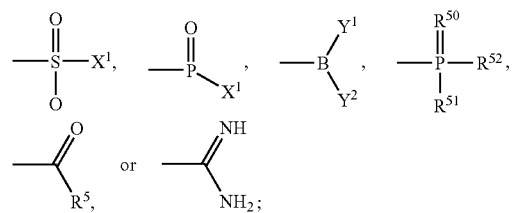

$R^1$ is selected from the group consisting of hydrogen, a C-terminally linked amino acid or peptide or analog thereof, and an amino protecting group wherein optionally where applicable the bond between $R^1$ and the N to which it is attached is a thioxamide bond;

$R^2$ represents one or more substitutions to the ring A, each of which is independently a halogen, lower alkyl, lower alkenyl, lower alkynyl, carbonyl (such as a carboxyl, ester, formate, or ketone), thiocarbonyl (such as a thioester, thioacetate, or thioformate), amino, acylamino, amido, nitro, sulfate, sulfonate, sulfonamido, —$(CH_2)_m$—$R^7$, —$(CH_2)_m$—OH, —$(CH_2)_m$—O-lower alkyl, —$(CH_2)_m$—O-lower alkenyl, —$(CH_2)_n$—O—$(CH_2)_m$—$R^7$, —$(CH_2)_m$—SH, —$(CH_2)_m$—S-lower alkyl, —$(CH_2)_m$—S-lower alkenyl, or —$(CH_2)_n$—S—$(CH_2)_m$—$R^7$, azido, cyano, isocyanato, thiocyanato, isothiocyanato, cyanato,

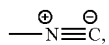

or

wherein at least one $R^2$ is selected from the group consisting of —OH, lower alkyl, lower alkoxy, lower hydroxyalkyl, and lower alkoxyalkyl, preferably at least one of lower alkyl (e.g., methyl), lower alkoxy, lower hydroxyalkyl (e.g., hydroxymethyl), and lower alkoxyalkyl;

$R^5$ is selected from the group consisting of hydrogen, alkyl, alkenyl, alkynyl, —$C(X^1)(X^2)X^3$, —$(CH_2)_m$—$R^6$, —$(CH_2)_n$—OH, —$(CH_2)_n$—O-alkyl, —$(CH_2)_n$—O-alkenyl, —$(CH_2)_n$—O-alkynyl, —$(CH_2)_n$—O—$(CH_2)_m$—$R^6$, —$(CH_2)_n$—SH, —$(CH_2)_n$—S-alkyl, —$(CH_2)_n$—S-alkenyl, —$(CH_2)_n$—S-alkynyl, —$(CH_2)_n$—S—$(CH_2)_m$—$R^6$, —C(O)C(O)$NH_2$, and —C(O)C(O)$OR^7$;

each $R^6$ is independently selected from aryl, aralkyl, cycloalkyl, cycloalkenyl, and heterocyclyl;

each $R^7$ is independently selected from hydrogen, alkyl, alkenyl, aryl, aralkyl, cycloalkyl, cycloalkenyl, and heterocycle;

$R_8$ represents hydrogen, —$CH_3$, or —$(CH_2)_n$—$CH_3$;

$Y^1$ and $Y^2$ are each independently selected from —OH, or a group capable of being hydrolyzed to a hydroxyl group, including cyclic derivatives where $Y^1$ and $Y^2$ are connected via a ring having from 5 to 8 atoms in the ring structure (such as pinacol or the like), $R^{50}$ is O or S;

$R^{51}$ is selected from the group consisting of $N_3$, $SH_2$, $NH_2$, $NO_2$ or —$OR^7$;

$R^{52}$ represents hydrogen, a lower alkyl, an amine, —$OR^7$, or a pharmaceutically acceptable salt thereof, or $R^{51}$ and $R^{52}$ taken together with the phosphorous atom to which they are attached complete a heterocyclic ring having from 5 to 8 atoms in the ring structure;

$X^1$ represents a halogen;

$X^2$ and $X^3$ are each independently selected from hydrogen and halogen;

m is zero or an integer in the range of 1 to 8; and n is an integer in the range of 1 to 8.

In certain embodiments, W is selected from the group consisting of CN and B($Y^1$)($Y^2$), wherein $Y^1$ and $Y^2$ are each independently or OH, or a group capable of being hydrolyzed to OH, including cyclic derivatives where $Y^1$ and $Y^2$ are connected via a ring having from 5 to 8 atoms in the ring structure. In certain certain embodiments, A is a five-membered ring, and W is B(Y$^1$)(Y$^2$). In more certain embodiments, Cα has the absolute stereochemical configuration of L-proline.

In certain embodiments, A is a five-membered ring and R$^2$ is selected from the group consisting of hydroxyl, lower alkyl, lower alkenyl, lower alkynyl, lower alkoxy, lower hydroxyalkyl, and lower alkoxyalkyl. In certain preferred such embodiments, R$^2$ is selected from the group consisting of lower hydroxyalkyl (hydroxymethyl) and lower alkoxyalkyl. In more preferred such embodiments, R$^2$ is located at the 5-position of the ring.

In certain embodiments, A is a five-membered ring, and R$^2$ is selected from the group consisting of hydroxyl, lower alkyl, lower hydroxyalkyl and lower alkoxyalkyl. In certain preferred such embodiments, Cα has the absolute stereochemical configuration of L-proline and R$^2$ is located at the 5-position of the ring for lower alkyl (such as methyl), lower hydroxyalkyl (such as hydroxymethyl) and lower alkoxyalkyl or at the 4-position for hydroxyl. In more preferred such embodiments, R$^2$ has a cis-stereochemical relationship to W.

In certain embodiments, R$^2$ is azido, cyano, isocyanato, thiocyanato, isothiocyanato, cyanato,

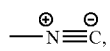

or

In certain embodiments, p Cα has the absolute stereochemical configuration of L-proline and R$^2$ is located at the 5-position of the ring.

Another aspect of the invention relates to compounds having a structure of Formula XXVII:

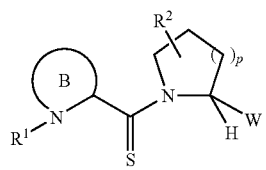

(XXVII)

or a pharmaceutically acceptable salt thereof, wherein

B, R$^1$, R$^2$ and W are as defined above for Formula XXVI, and p is an integer from 1 to 3. In certain certain embodiments, p is 1.

In certain embodiments, W is selected from the group consisting of CN and B(Y$^1$)(Y$^2$), wherein Y$^1$ and Y$^2$ are each independently or OH, or a group capable of being hydrolyzed to OH, including cyclic derivatives where Y$^1$ and Y$^2$ are connected via a ring having from 5 to 8 atoms in the ring structure. In certain certain embodiments, W is B(Y$^1$)(Y$^2$). In more certain embodiments, the carbon bearing W has the absolute stereochemical configuration of L-proline.

In certain embodiments, R$^2$ is selected from the group consisting of hydroxyl, lower alkyl, lower alkenyl, lower alkynyl, lower alkoxy, lower hydroxyalkyl, and lower alkoxyalkyl. In certain preferred such embodiments, R$^2$ is selected from the group consisting of lower hydroxyalkyl (such as hydroxymethyl) and lower alkoxyalkyl. In more preferred such embodiments, R$^2$ is located at the 5-position of the ring.

In certain embodiments, R$^2$ is selected from the group consisting of hydroxyl, lower alkyl, lower hydroxyalkyl and lower alkoxyalkyl. In certain preferred such embodiments, p is 1, the carbon bearing W has the absolute stereochemical configuration of L-proline and R$^2$ is located at the 4-position of the ring for hydroxyl or at the 5-position for lower alkyl (such as methyl), lower hydroxyalkyl (such as hydroxymethyl) and lower alkoxyalkyl. In more preferred such embodiments, R$^2$ has a cis-stereochemical relationship to W.

In certain embodiments, R$^2$ is azido, cyano, isocyanato, thiocyanato, isothiocyanato, cyanato,

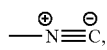

or

In certain embodiments, p is 1, the carbon bearing W has the absolute stereochemical configuration of L-proline and R$^2$ is located at the 5-position of the ring.

Another aspect of the invention relates to compounds having a structure of Formula XXVIII:

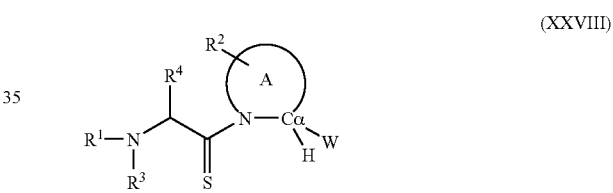

(XXVIII)

or a pharmaceutically acceptable salt thereof, wherein

A is a 4-8 membered heterocycle including the N and the Cα carbon;

W is a functional group which reacts with an active site residue of the targeted protease to form a covalent adduct, as for example, —CN, —CH=NR$^5$,

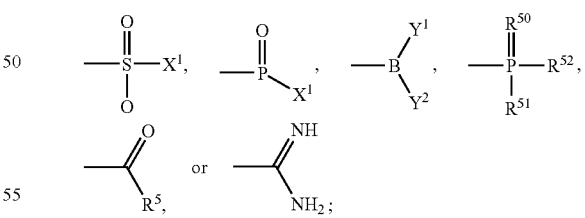

R$^1$ represents a C-terminally linked peptide or peptide analog which is a substrate for an activating enzyme; wherein optionally the bond between R$^1$ and the N to which it is bonded is a thioxamide bond;

R$^2$ represents one or more substitutions to the ring A, each of which is independently a halogen, lower alkyl, lower alkenyl, lower alkynyl, carbonyl (such as a carboxyl, ester, formate, or ketone), thiocarbonyl (such as a thioester, thioacetate, or thioformate), amino, acylamino, amido, nitro, sulfate, sulfonate, sulfonamido, —(CH$_2$)$_m$—R$^7$, —(CH$_2$)$_m$—

OH, —(CH$_2$)$_m$—O-lower alkyl, —(CH$_2$)$_m$—O-lower alkenyl, —(CH$_2$)$_n$—O—(CH$_2$)$_m$—R$^7$, —(CH$_2$)$_m$—SH, —(CH$_2$)$_m$—S-lower alkyl, —(CH$_2$)$_m$—S-lower alkenyl, or —(CH$_2$)$_n$—S—(CH$_2$)$_m$—R$^7$, azido, cyano, isocyanato, thiocyanato, isothiocyanato, cyanato, —N$\overset{\oplus}{\equiv}$C$^{\ominus}$, or

—C≡C—R$^{10}$, wherein at least one R$^2$ is selected from the group consisting of —OH, lower alkyl, lower alkoxy, lower hydroxyalkyl, and lower alkoxyalkyl, preferably at least one of lower alkyl (e.g., methyl), lower alkoxy, lower hydroxyalkyl (e.g., hydroxymethyl), and lower alkoxyalkyl;

R$^3$ is selected from the group consisting of hydrogen and a substituent which does not conjugate the electron pair of the nitrogen to which it is attached, such as a lower alkyl;

R$^4$ is selected from the group consisting of hydrogen and a small hydrophobic group such as a halogen, lower alkyl, lower alkenyl, or lower alkynyl;

R$^5$ is selected from the group consisting of hydrogen, alkyl, alkenyl, alkynyl, —C(X$^1$)(X$^2$)X$^3$, —(CH$^2$)$^m$—R$^6$, —(CH$^2$)$^n$—OH, —(CH$^2$)$^n$—O-alkyl, —(CH$^2$)$^n$-alkenyl, —(CH$^2$)$^n$—O-alkynyl, —(CH$^2$)$^n$—O—(CH$^2$)—R$^6$, —(CH$^2$)$^n$—SH, —(CH$^2$)$^n$—S-alkyl, —(CH$^2$)$^n$—S-alkenyl-(CH$^2$)$^n$—S-alkynyl, —(CH$^2$)$^n$—S—(CH$^2$)$^m$—R$^6$, —C(O)C(O)NH$^2$, —C(O)C(O)OR$^7$;

R$^6$ represents, for each occurrence, a substituted or unsubstituted aryl, aralkyl, cycloalkyl, cycloalkenyl, or heterocycle;

R$^7$ represents, for each occurrence, hydrogen, or a substituted or unsubstituted alkyl, alkenyl, aryl, aralkyl, cycloalkyl, cycloalkenyl, or heterocycle;

R$^8$ represents hydrogen, —CH$_3$, or —(CH$_2$)$_n$—CH$_3$; and

Y$^1$ and Y$^2$ are independently or together OH or a group capable of being hydrolyzed to a hydroxyl group, including cyclic derivatives where Y$^1$ and Y$^2$ are connected via a ring having from 5 to 8 atoms in the ring structure (such as pinacol or the like), R$^{50}$ is O or S;

R$^{51}$ is selected from the group consisting of N$_3$, SH$_2$, NH$_2$, NO$_2$ and —OR$^7$;

R$^{52}$ is selected from the group consisting of hydrogen, lower alkyl, amine, —OR$^7$, or a pharmaceutically acceptable salt thereof; or R$^{51}$ and R$^{52}$ taken together with the phosphorous atom to which they are attached complete a heterocyclic ring having from 5 to 8 atoms in the ring structure;

X$^1$ is a halogen;

X$^2$ and X$^3$ are each independently selected from hydrogen and halogen;

m is zero or an integer in the range of 1 to 8; and n is an integer in the range of 1 to 8.

In certain embodiments, W is selected from the group consisting of CN and B(Y$^1$)(Y$^2$). In certain certain embodiments, A is a five-membered ring, and W is B(Y$^1$)(Y$^2$). In more certain embodiments, Cα has the absolute stereochemical configuration of L-proline.

In certain embodiments, A is a five-membered ring, Z is C, and R$^2$ is selected from the group consisting of hydroxyl, lower alkyl, lower alkenyl, lower alkynyl, lower alkoxy, lower hydroxyalkyl, and lower alkoxyalkyl. In certain preferred such embodiments, R$^2$ is selected from the group consisting of lower hydroxyalkyl (such as hydroxymethyl) and lower alkoxyalkyl. In more preferred such embodiments, R$^2$ is located at the 5-position of the ring.

In certain embodiments, A is a five-membered ring and R$^2$ is selected from the group consisting of hydroxyl, lower alkyl, lower hydroxyalkyl and lower alkoxyalkyl. In certain preferred such embodiments, Cα has the absolute stereochemical configuration of L-proline and R$^2$ is located at the 4-position of the ring for hydroxyl or at the 5-position for lower alkyl, lower hydroxyalkyl and lower alkoxyalkyl. In more preferred such embodiments, R$^2$ has a cis-stereochemical relationship to W.

In certain embodiments, R$^2$ is azido, cyano, isocyanato, thiocyanato, isothiocyanato, cyanato, —N$\overset{\oplus}{\equiv}$C$^{\ominus}$, or

—C≡C—R$_8$.

In certain embodiments, Cα has the absolute stereochemical configuration of L-proline. In more certain embodiments, R$^2$ is located at the 5-position of the ring.

One aspect of the invention relates to compounds having a structure of Formula XXIX:

(XXIX)

or a pharmaceutically acceptable salt thereof, wherein

L is absent or is —XC(O)—;

R$^1$ is selected from the group consisting of H, lower alkyl, lower acyl, lower aralkyl, lower aracyl, lower heteroaracyl, carbocyclyl, aryl, and ArSO$_2$—; wherein optionally when L is absent the bond between R$^1$ and the N to which it is bonded is a thioxamide bond;

R$^2$ represents one or more substitutions to the ring A, each of which is independently a halogen, lower alkyl, lower alkenyl, lower alkynyl, carbonyl (such as a carboxyl, ester, formate, or ketone), thiocarbonyl (such as a thioester, thioacetate, or thioformate), amino, acylamino, amido, nitro, sulfate, sulfonate, sulfonamido, —(CH$_2$)$_m$—R$^7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$^7$, —(CH$_2$)$_m$—SH, —(CH$_2$)$_m$—S-lower alkyl, —(CH$_2$)$_m$—S-lower alkenyl, or —(CH$_2$)$_n$—S—(CH$_2$)$_m$—R$^7$, azido, cyano, isocyanato, thiocyanato, isothiocyanato, cyanato, —N$\overset{\oplus}{\equiv}$C$^{\ominus}$, or $$-C\equiv C-R^{10},$$

wherein at least one $R^2$ is selected from the group consisting of —OH, lower alkyl, lower alkoxy, lower hydroxyalkyl, and lower alkoxyalkyl, preferably at least one of lower alkyl (e.g., methyl), lower alkoxy, lower hydroxyalkyl (e.g., hydroxymethyl), and lower alkoxyalkyl;

$R^3$ is selected from the group consisting of hydrogen, lower alkyl, lower hydroxyalkyl, lower thioalkyl, and lower aralkyl;

$R^4$ is selected from the group consisting of H and lower alkyl, or $R^1$ and $R^4$ together are phthaloyl, thereby forming a ring;

$R^6$ represents, for each occurrence, a substituted or unsubstituted aryl, aralkyl, cycloalkyl, cycloalkenyl, or heterocycle;

$R_8$ represents hydrogen, —$CH_3$, or —$(CH_2)_n$—$CH_3$;

W is selected from the group consisting of $B(Y^1)(Y^2)$ and CN;

$Y^1$ and $Y^2$ are independently selected from OH or a group that is hydrolysable to an OH, or together with the boron atom to which they are attached form a 5- to 8-membered ring that is hydrolysable to OH;

X is selected from the group consisting of O and NH.

In certain embodiments, W is $B(Y^1)(Y^2)$. In certain certain embodiments, $R^2$ is selected from the group consisting of hydroxyl, lower alkyl, lower alkenyl, lower alkynyl, lower alkoxy, lower hydroxyalkyl, and lower alkoxyalkyl. In more preferred such embodiments, $R^2$ is selected from the group consisting of lower hydroxyalkyl and lower alkoxyalkyl. In more preferred such embodiments, $R^2$ is located at the 5-position of the ring.

In certain embodiments, $R^2$ is selected from the group consisting of hydroxyl, lower alkyl, lower hydroxyalkyl and lower alkoxyalkyl. In certain preferred such embodiments, Cα has the absolute stereochemical configuration of L-proline and $R^2$ is located at the 4-position of the ring for hydroxyl or at the 5-position for lower alkyl, lower hydroxyalkyl and lower alkoxyalkyl. In more preferred such embodiments, $R^2$ has a cis-stereochemical relationship to W.

Embodiment F

A representative class of compounds for use in the method of the present invention are represented by formula XXX:

(XXX)

wherein $R^1$ is selected from the group consisting of H, alkyl, alkoxy, alkenyl, alkynyl, amino, alkylamino, acylamino, cyano, sulfonylamino, acyloxy, aryl, cycloalkyl, heterocyclyl, heteroaryl, and polypeptide chains of 1 to 8 amino acid residues;

$R^2$ is selected from the group consisting of H, lower alkyl, and aralkyl;

$R^3$ is selected from the group consisting of
(a) lower alkyl;
(b) $R^aR^bN(CH_2)_m$— wherein
$R^a$ is a pyridinyl or pyrimidinyl moiety optionally substituted with $(C_{1-4})$alkyl, $(C_{1-4})$alkoxy, halogen, trifluoromethyl, cyano or nitro; or phenyl optionally mono- or independently disubstituted with $(C_{1-4})$alkyl, $(C_{1-4})$alkoxy or halogen;
$R^b$ is hydrogen or $(C_{1-8})$alkyl and m is 2 or 3;
(c) $(C_{3-2})$cycloalkyl optionally monosubstituted in the 1-position with $(C_{1-3})$hydroxyalkyl;
(d) $R^c(CH_2)_n$— wherein either $R^c$ is phenyl optionally substituted with $(C_{1-4})$alkyl, $(C_{1-4})$alkoxy, halogen or phenylthio optionally monosubstituted in the phenyl ring with hydroxymethyl; or is $(C_{1-8})$alkyl; a [3.1.1] bicyclic carbocyclic moiety optionally substituted with $(C_{1-8})$alkyl; a pyridinyl or naphthyl moiety optionally substituted with $(C_{1-4})$alkyl, $(C_{1-4})$alkoxy or halogen; cyclohexene; or adamantyl and n is 1 to 3; or $R^c$ is phenoxy optionally substituted with $(C_{1-4})$alkyl, $(C_{1-4})$alkoxy or halogen and n is 2 or 3;
(e) $(R^d)_2CH(CH_2)_2$— wherein each $R^d$ independently is phenyl optionally substituted with $(C_{1-4})$alkyl, $(C_{1-4})$alkoxy, or halogen;
(f) $R^e(CH_2)_p$— wherein $R^e$ is 2-oxopyrrolidinyl or $(C_{2-4})$ alkoxy and p is 2 to 4; and
(g) $R^g$ wherein $R^g$ is: indanyl; a pyrrolidinyl or piperidinyl moiety optionally substituted with benzyl; a [2.2.1]- or [3.1.1] bicyclic carbocyclic moiety optionally substituted with $(C_{1-8})$alkyl; adamantyl; or $(C_{1-8})$alkyl optionally substituted with hydroxy, hydroxymethyl or phenyl optionally substituted with $(C_{1-4})$alkyl, $(C_{1-4})$alkoxy or halogen;

$R^4$ is selected from the group consisting of H, halogen, and lower alkyl;

$R^5$ is selected from the group consisting of H, halogen lower alkyl, and aralkyl, preferably H or lower alkyl;

$R^6$ is a functional group that reacts with an active site residue of the targeted protease to form a covalent adduct;

$R^7$ is selected from the group consisting of alkyl, alkoxy, alkenyl, alkynyl, aminoalkyl, aminoacyl, acyloxy, aryl, aralkyl, cycloalkyl, heterocyclyl, heteroaryl, or heteroaralkyl;

$R^8$ is selected from the group consisting of H, aryl, alkyl, aralkyl, cycloalkyl, heterocyclyl, heteroaryl, heteroaralkyl, and polypeptide chains of 1 to 8 amino acid residues;

L is absent or is selected from the group consisting of alkyl, alkenyl, alkynyl, $(CH_2)_m$—O—$(CH_2)_m$—, —$(CH_2)_m NR_2(CH_2)_m$—, and —$(CH_2)_m S(CH_2)_m$—;

X is absent or is selected from the group consisting of —$N(R^8)$—, —O—, and —S—;

Y is absent or is selected from the group consisting of —C(=O)—, —C(=S)—, and —$SO_2$—, m is, independently for each occurrence, an integer from 0 to 10; and n is an integer from 1 to 6.

In certain embodiments, $R^1$ is H or lower alkyl and $R^4$ and $R^5$ are both hydrogen. In certain such embodiments, $R^3$ is lower alkyl. In certain preferred such embodiments, $R^3$ is selected from the group consisting of methyl, ethyl, and isopropyl.

In certain embodiments $R^3$ is a substituted lower alkyl. In certain such embodiments, $R^3$ is substituted with a group selected from halogen, hydroxyl, carbonyl, thiocarbonyl, alkoxy, amino, amido, amidine, cyano, nitro, alkylthio, heterocyclyl, aryl, and heteroaryl.

In certain embodiments, X, Y, and L are absent and $R^1$ is a polypeptide chain of 2 to 8 amino acid residues. In certain such embodiments, $R^1$ is a polypeptide chain of 2 amino acid residues. In such embodiments, the bond between $R^1$ and N may be a thioxamide bond.

In certain other embodiments, $R^6$ is selected from the group consisting of boronic acid, CN, —$SO_2Z^1$, —$P(=O)Z^1$, —$P(=R^9)R^{10}R^{11}$, —$C(=NH)NH_2$, —$CH=NR^{12}$, or —$C(=O)$—$R^{12}$ wherein $R^9$ is selected from the group consisting of O and S;

$R^{10}$ is selected from the group consisting of $N_3$, $SH_2$, $NH_2$, $NO_2$, and $OLR^{13}$, and $R^{11}$ is selected from the group consisting of lower alkyl, amino, and $OLR^3$, or a pharmaceutically acceptable salt thereof; or $R^{10}$ and $R^{11}$, together with the phosphorus to which they are attached, form a 5- to 8-membered heterocyclic ring;

$R^{12}$ is selected from the group consisting of H, alkyl, alkenyl, alkynyl, $NH_2$, —$(CH_2)_p$—$R^{13}$, —$(CH_2)_q$—OH, —$(CH_2)_q$—O-alkyl, —$(CH_2)_q$—O-alkenyl, —$(CH_2)_q$—O-alkynyl, —$(CH_2)_q$—O—$(CH_2)_p$—$R^{13}$, —$(CH_2)_q$—SH, —$(CH_2)_q$—S-alkyl, —$(CH_2)_q$—S-alkenyl, —$(CH_2)_q$—S-alkynyl, —$(CH_2)_q$—S—$(CH_2)_p$—$R^{13}$, —$C(O)NH_2$, —$C(O)OR^{14}$, and $C(Z^1)(Z^1)(Z^1)$;

$R^{13}$ is selected from the group consisting of H, alkyl, alkenyl, aryl, heteroaryl, cycloalkyl, cycloalkenyl, and heterocyclyl;

$R^{14}$ is selected from the group consisting of H, alkyl, alkenyl, and $LR^3$;

$Z^1$ is a halogen;

$Z^2$ and $Z^3$ are independently selected from H and halogen;

p is, independently for each occurrence, an integer from 0 to 8; and q is, independently for each occurrence, an integer from 1 to 8.

In certain embodiments, $R^6$ is selected from the group consisting of CN, CHO, and $C(=O)C(Z^1)(Z^2)(Z^3)$, wherein $Z^1$ is a halogen and $Z^2$ and $Z^3$ are independently selected from H and halogen. In another embodiment, $R^6$ is selected from the group consisting of $C(=O)C(Z^1)(Z^2)(Z^3)$, wherein $Z^1$ is fluorine and $Z^2$ and $Z^3$ are independently selected from H and fluorine.

In certain certain embodiments, $R^6$ is a group —$B(Y^1)(Y^2)$, wherein $Y^1$ and $Y^2$ are independently OH or a group that is hydrolysable to a boronic acid, or together with the boron atom to which they are attached form a 5- to 8-membered ring that is hydrolysable to a boronic acid.

In certain embodiments, exemplary compounds of the present invention include:

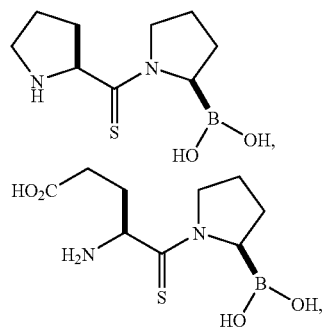

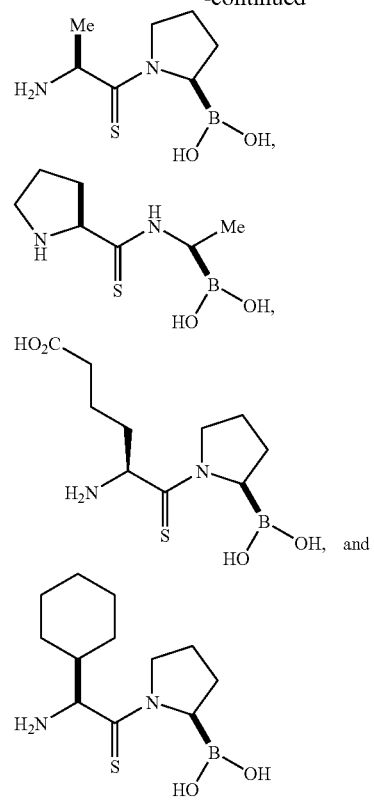

or enantiomers or diastereomers thereof.

Also included are compounds of Formulas I-XXX, wherein one or more amide groups are replaced by one or more thioxamide groups.

Also included are such peptidomimetics as olefins, phosphonates, aza-amino acid analogs and the like.

Also deemed as equivalents are any compounds which can be hydrolytically converted into any of the aforementioned compounds including boronic acid esters and halides, and carbonyl equivalents including acetals, hemiacetals, ketals, and hemiketals, and cyclic dipeptide analogs.

As used herein, the definition of each expression, e.g., alkyl, m, n, etc., when it occurs more than once in any structure, is intended to be independent of its definition elsewhere in the same structure.

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

The pharmaceutically acceptable salts of the present invention can be synthesized from the subject compound which contain a basic or acid moiety by conventional chemical methods. Generally, the salts are prepared by reacting the free base or acid with stoichiometric amounts or with an excess of the desired salt-forming inorganic or organic acid or base in a suitable solvent. The pharmaceutically acceptable salts of the acids of the subject compounds are also readily prepared by conventional procedures such as treating an acid of the present compounds with an appropriate amount of a base such as an alkali or alkaline earth methyl hydroxide (e.g., sodium, potassium, lithium, calcium or magnesium) or an organic base such as an amine, piperidine, pyrrolidine, benzylamine and the like, or a quaternary ammonium hydroxide such as tetramethylammonium hydroxide and the like.

Contemplated equivalents of the compounds described above include compounds which otherwise correspond thereto, and which have the same general properties thereof (e.g., the ability to inhibit proteolysis of GLP-1 or other peptide hormone or precursor thereof), wherein one or more simple variations of substituents are made which do not adversely affect the efficacy of the compound in use in the contemplated method. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

In certain certain embodiments, the compounds are DPIV inhibitors with a $K_i$ for DPIV inhibition of 10 nm or less, more preferably of 1.0 nm or less, and even more preferably of 0.1 or even 0.01 nM or less. Indeed, inhibitors with $K_i$ values in the picomolar and even femtomolar range are contemplated.

Another aspect of the present invention relates to pharmaceutical compositions of the dipeptidylpeptidase inhibitors disclosed herein, particularly compound(s) and their uses in treating and/or preventing (inhibiting) disorders which can be improved by altering the homeostasis of peptide hormones. In a certain embodiment, the compounds have hypoglycemic and antidiabetic activities, and can be used in the treatment of disorders marked by aberrant glucose metabolism (including storage). In particular embodiments, the compositions of the subject methods are useful as insulinotropic agents, or to potentiate the insulinotropic effects of such molecules as GLP-1. In this regard, the present method can be useful for the treatment and/or prophylaxis of a variety of disorders, including one or more of: hyperlipemia, hyperglycemia, obesity, glucose tolerance insufficiency, insulin resistance, and diabetic complications.

For instance, in certain embodiments the method involves administration of a compound(s), preferably at a predetermined interval(s) during a 24-hour period, in an amount effective to improve one or more aberrant indices associated with glucose metabolism disorders (e.g., glucose intolerance, insulin resistance, hyperglycemia, hyperinsulinemia, and Type II diabetes). The effective amount of the compound may be about 0.01, 0.1, 1, 10, 30, 50, 70, 100, 150, 200, 500, or 1000 mg/kg of the subject.

(ii). Agonism of GLP-1 Effects

The compounds useful in the subject methods possess, in certain embodiments, the ability to lower blood glucose levels, to relieve obesity, to alleviate impaired glucose tolerance, to inhibit hepatic glucose neogenesis, and to lower blood lipid levels and to inhibit aldose reductase. They are thus useful for the prevention and/or therapy of hyperglycemia, obesity, hyperlipidemia, diabetic complications (including retinopathy, nephropathy, neuropathy, cataracts, coronary artery disease and arteriosclerosis), and furthermore for obesity-related hypertension and osteoporosis.

Diabetes mellitus is a disease characterized by hyperglycemia occurring from a relative or absolute decrease in insulin secretion, decreased insulin sensitivity, or insulin resistance. The morbidity and mortality of this disease result from vascular, renal, and neurological complications. An oral glucose tolerance test is a clinical test used to diagnose diabetes. In an oral glucose tolerance test, a patient's physiological response to a glucose load or challenge is evaluated. After ingesting the glucose, the patient's physiological response to the glucose challenge is evaluated. Generally, this is accomplished by determining the patient's blood glucose levels (the concentration of glucose in the patient's plasma, serum, or whole blood) for several predetermined points in time.

In one embodiment, the present invention provides a method for agonizing the action of GLP-1. It has been determined that isoforms of GLP-1 (GLP-1(7-37) and GLP-1(7-36)), which are derived from preproglucagon in the intestine and the hind brain, have insulinotropic activity, i.e., they modulate glucose metabolism. DPIV cleaves the isoforms to inactive peptides. Thus, in certain embodiments, compound(s) of the present invention can agonize insulinotropic activity by interfering with the degradation of bioactive GLP-1 peptides.

(iii). Agonism of the Effects of Other Peptide Hormones

In another embodiment, the subject agents can be used to agonize (e.g., mimic or potentiate) the activity of peptide hormones, e.g., GLP-2, GIP and NPY.

To illustrate further, the present invention provides a method for agonizing the action of GLP-2. It has been determined that GLP-2 acts as a trophic agent, to promote growth of gastrointestinal tissue. The effect of GLP-2 is marked particularly by increased growth of the small bowel, and is therefore herein referred to as an "intestinotrophic" effect. DPIV is known to cleave GLP-2 into a biologically inactive peptide. Thus, in one embodiment, inhibition of DPIV interferes with the degradation of GLP-2, and thereby increases the plasma half-life of that hormone.

In still other embodiments, the subject method can be used to increase the half-life of other proglucagon-derived peptides, such as glicentin, oxyntomodulin, glicentin-related pancreatic polypeptide (GRPP), and/or intervening peptide-2 (IP-2). For example, glicentin has been demonstrated to cause proliferation of intestinal mucosa and also inhibits a peristalsis of the stomach, and has thus been elucidated as useful as a therapeutic agent for digestive tract diseases, thus leading to the present invention.

Thus, in one aspect, the present invention relates to therapeutic and related uses of compound(s) for promoting the growth and proliferation of gastrointestinal tissue, most particularly small bowel tissue. For instance, the subject method can be used as part of a regimen for treating injury, inflammation, or resection of intestinal tissue, e.g., where enhanced growth and repair of the intestinal mucosal epithelial is desired.

With respect to small bowel tissue, such growth is measured conveniently as an increase in small bowel mass and length, relative to an untreated control. The effect of compounds on small bowel also manifests as an increase in the height of the crypt plus villus axis. Such activity is referred to herein as an "intestinotrophic" activity. The efficacy of the subject method may also be detectable as an increase in crypt cell proliferation and/or a decrease in small bowel epithelium apoptosis. These cellular effects may be noted most significantly in relation to the jejunum, including the distal jejunum and particularly the proximal jejunum, and also in the distal ileum. A compound is considered to have "intestinotrophic effect" if a test animal exhibits significantly increased small bowel weight, increased height of the crypt plus villus axis or increased crypt cell proliferation, or decreased small bowel epithelium apoptosis when treated with the compound (or genetically engineered to express it themselves). A model suitable for determining such gastrointestinal growth is described by U.S. Pat. No. 5,834,428.

In general, patients who would benefit from either increased small intestinal mass and consequent increased small bowel mucosal function are candidates for treatment by the subject method. Particular conditions that may be treated include the various forms of sprue, including celiac sprue which results from a toxic reaction to α-gliadin from wheat, and is marked by a tremendous loss of villae of the bowel; tropical sprue which results from infection and is marked by partial flattening of the villae; hypogammaglobulinemic sprue which is observed commonly in patients with common variable immunodeficiency or hypogammaglobulinemia and is marked by significant decrease in villus height. The therapeutic efficacy of the treatment may be monitored by enteric biopsy to examine the villus morphology, by biochemical assessment of nutrient absorption, by patient weight gain, or by amelioration of the symptoms associated with these conditions. Other conditions that may be treated by the subject method, or for which the subject method may be useful prophylactically, include radiation enteritis, infectious or post-infectious enteritis, regional enteritis (Crohn's disease), small intestinal damage due to toxic or other chemotherapeutic agents, and patients with short bowel syndrome.

More generally, the present invention provides a therapeutic method for treating digestive tract diseases. The term "digestive tract" as used herein means a tube through which food passes, including stomach and intestine. The term "digestive tract diseases" as used herein means diseases accompanied by a qualitative or quantitative abnormality in the digestive tract mucosa, which include, e.g., ulceric or inflammatory disease; congenital or acquired digestion and absorption disorder including malabsorption syndrome; disease caused by loss of a mucosal barrier function of the gut; and protein-losing gastroenteropathy. The ulceric disease includes, e.g., gastric ulcer, duodenal ulcer, small intestinal ulcer, colonic ulcer, and rectal ulcer. The inflammatory disease include, e.g., esophagitis, gastritis, duodenitis, enteritis, colitis, Crohn's disease, proctitis, gastrointestinal Behcet, radiation enteritis, radiation colitis, radiation proctitis, enteritis, and medicamentosa. The malabsorption syndrome includes the essential malabsorption syndrome such as disaccharide-decomposing enzyme deficiency, glucose-galactose malabsorption, fructose malabsorption; secondary malabsorption syndrome, e.g., the disorder caused by a mucosal atrophy in the digestive tract through the intravenous or parenteral nutrition or elemental diet, the disease caused by the resection and shunt of the small intestine such as short gut syndrome, cul-de-sac syndrome; and indigestible malabsorption syndrome, such as the disease caused by resection of the stomach, e.g., dumping syndrome.

The term "therapeutic agent for digestive tract diseases" as used herein means the agents for the prevention and treatment of the digestive tract diseases, which include, e.g., the therapeutic agent for digestive tract ulcer, the therapeutic agent for inflammatory digestive tract disease, the therapeutic agent for mucosal atrophy in the digestive tract, the therapeutic agent for a digestive tract wound, the amelioration agent for the function of the digestive tract including the agent for recovery of the mucosal barrier function, and the amelioration agent for digestive and absorptive function. Ulcers include digestive ulcers and erosions, and acute ulcers, namely acute mucosal lesions.

The subject method, because of promoting proliferation of intestinal mucosa, can be used in the treatment and prevention of pathologic conditions of insufficiency in digestion and absorption, that is, treatment and prevention of mucosal atrophy, or treatment of hypoplasia of the digestive tract tissues and decrease in these tissues by surgical removal as well as improvement of digestion and absorption. Further, the subject method can be used in the treatment of pathologic mucosal conditions due to inflammatory diseases such as enteritis, Crohn's disease, and ulceric colitis and also in the treatment of reduction in function of the digestive tract after operation, for example, in damping syndrome as well as in the treatment of duodenal ulcer in conjunction with the inhibition of peristalsis of the stomach and rapid migration of food from the stomach to the jejunum. Furthermore, glicentin can effectively be used in promoting cure of surgical invasion as well as in improving functions of the digestive tract. Thus, the present invention also provides a therapeutic agent for atrophy of the digestive tract mucosa, a therapeutic agent for wounds in the digestive tract and a drug for improving functions of the digestive tract which comprise glicentin as active ingredients.

Likewise, the compound(s) of the subject invention can be used to alter the plasma half-life of secretin, VIP, PHI, PACAP, GIP, and/or helodermin. Additionally, the subject method can be used to alter the pharmacokinetics of Peptide YY and neuropeptide Y, both members of the pancreatic polypeptide family, as DPIV has been implicated in the processing of those peptides in a manner which alters receptor selectivity.

Neuropeptide Y (NPY) is believed to act in the regulation vascular smooth muscle tone, as well as regulation of blood pressure. NPY also decreases cardiac contractility. NPY is also the most powerful appetite stimulant known (Wilding et al., *J. Endocrinology* 1992, 132, 299-302). The centrally evoked food intake (appetite stimulation) effect is predominantly mediated by NPY Y1 receptors and causes increase in body fat stores and obesity (Stanley et al., *Physiology and Behavior* 1989, 46, 173-177).

According to the present invention, a method for treatment of anorexia comprises administering to a host subject an effective amount of a compound(s) to stimulate the appetite and increase body fat stores which thereby substantially relieves the symptoms of anorexia.

A method for treatment of hypotension comprises administering to a host subject an effective amount of a compound(s) of the present invention to mediate vasoconstriction and increase blood pressure which thereby substantially relieves the symptoms of hypotension.

DPIV has also been implicated in the metabolism and inactivation of growth hormone-releasing factor (GHRF). GHRF is a member of the family of homologous peptides that includes glucagon, secretin, vasoactive intestinal peptide (VIP), peptide histidine isoleucine (PHI), pituitary adenylate cyclase activating peptide (PACAP), gastric inhibitory peptide (GIP) and helodermin (Kubiak et al. *Peptide Res.* 1994, 7, 153). GHRF is secreted by the hypothalamus, and stimulates the release of growth hormone (GH) from the anterior pituitary. Thus, the subject method can be used to improve clinical therapy for certain growth hormone deficient children, and in clinical therapy of adults to improve nutrition and to alter body composition (muscle vs. fat). The subject method can also be used in veterinary practice, for example, to develop higher yield milk production and higher yield, leaner livestock.

(iv). Assays of Insulinotropic Activity

In selecting a compound suitable for use in the subject method, it is noted that the insulinotropic property of a compound may be determined by providing that compound to animal cells, or injecting that compound into animals and monitoring the release of immunoreactive insulin (IRI) into the media or circulatory system of the animal, respectively. The presence of IRI can be detected through the use of a radioimmunoassay which can specifically detect insulin.

The db/db mouse is a genetically obese and diabetic strain of mouse. The db/db mouse develops hyperglycemia and hyperinsulinemia concomitant with its development of obesity and thus serves as a model of obese type 2 diabetes (NIDDM). The db/db mice can be purchased from, for example, The Jackson Laboratories (Bar Harbor, Me.). In an exemplary embodiment, for treatment of the mice with a regimen including a compound(s) or control, sub-orbital sinus blood samples are taken before and at some time (e.g., 60 min) after dosing of each animal. Blood glucose measurements can be made by any of several conventional techniques, such as using a glucose meter. The blood glucose levels of the control and compound(s) dosed animals are compared The metabolic fate of exogenous GLP-1 can also be followed in both nondiabetic or type II diabetic subjects, and the effect of a candidate compound(s) determined. For instance, a combination of high-pressure liquid chromatography (HPLC), specific radioimmunoassays (RIAs), and an enzyme-linked immunosorbent assay (ELISA), can be used, whereby intact biologically active GLP-1 and its metabolites can be detected. See, for example, Deacon et al. *Diabetes*, 1995, 44, 1126-1131. To illustrate, after GLP-1 administration, the intact peptide can be measured using an $NH_2$-terminally directed RIA or ELISA, while the difference in concentration between these assays and a COOH-terminal-specific RIA allowed determination of $NH_2$-terminally truncated metabolites. Without compound, subcutaneous GLP-1 is rapidly degraded in a time-dependent manner, forming a metabolite which co-elutes on HPLC with GLP-1(9-36) amide and has the same immunoreactive profile. For instance, 30 min after subcutaneous GLP-1 administration to diabetic patients (n=8), the metabolite accounted for 88.5+1.9% of the increase in plasma immunoreactivity determined by the COOH-terminal RIA, which was higher than the levels measured in healthy subjects (78.4+3.2%; n=8; P<0.05). See Deacon et al., supra. Intravenously infused GLP-I was also extensively degraded.

(v). Conjoint Administration

Another aspect of the invention provides a conjoint therapy wherein one or more other therapeutic agents are administered with the compound. Such conjoint treatment may be achieved by way of the simultaneous, sequential, or separate dosing of the individual components of the treatment.

In one embodiment, a compound(s) is conjointly administered with insulin or other insulinotropic agents, such as GLP-1, peptide hormones, such as GLP-2, GIP, or NPY, or a gene therapy vector which causes the ectopic expression of said agents and peptide hormones. In certain embodiments, said agents or peptide hormones may be variants of a naturally occurring or synthetic peptide hormone, wherein one or more amino acids have been added, deleted, or substituted.

In another illustrative embodiment, the compounds can be conjointly administered with an M1 receptor antagonist. Cholinergic agents are potent modulators of insulin release that act via muscarinic receptors. Moreover, the use of such agents can have the added benefit of decreasing cholesterol levels, while increasing HDL levels. Suitable muscarinic receptor antagonists include substances that directly or indirectly block activation of muscarinic cholinergic receptors. Preferably, such substances are selective (or are used in amounts that promote such selectivity) for the M1 receptor. Non-limiting examples include quaternary amines (such as methantheline, ipratropium, and propantheline), tertiary amines (e.g., dicyclomine and scopolamine), and tricyclic amines (e.g., telenzepine). Pirenzepine and methyl scopolamine are preferred. Other suitable muscarinic receptor antagonists include benztropine (commercially available as COGENTIN from Merck), hexahydro-sila-difenidol hydrochloride (HHSID hydrochloride disclosed in Lambrecht et al. *Trends in Pharmacol. Sci.* 1989, 10(Suppl), 60; (+/−)-3-quinuclidinyl xanthene-9-carboxylate hemioxalate (QNX-hemioxalate; Birdsall et al., *Trends in Pharmacol. Sci.* 1983, 4, 459; telenzepine dihydrochloride (Coruzzi et al. *Arch. Int. Pharmacodyn. Ther.* 1989, 302, 232; and Kawashima et al. *Gen. Pharmacol.* 1990, 21, 17), and atropine. The dosages of such muscarinic receptor antagonists will be generally subject to optimization as outlined above. In the case of lipid metabolism disorders, dosage optimization may be necessary independent of whether administration is timed by reference to the lipid metabolism responsiveness window or not.

In terms of regulating insulin and lipid metabolism and reducing the foregoing disorders, the compound(s) may also act synergistically with prolactin inhibitors such as d2 dopamine agonists (e.g., bromocriptine). Accordingly, the subject method can include the conjoint administration of such prolactin inhibitors as prolactin-inhibiting ergo alkaloids and prolactin-inhibiting dopamine agonists. Examples of suitable compounds include 2-bromo-alpha-ergocriptine, 6-methyl-8-beta-carbobenzyloxyaminoethyl-10-alpha-ergoline, 8-acylaminoergolines, 6-methyl-8-alpha-(N-acyl) amino-9-ergoline, 6-methyl-8-alpha-(N-phenylacetyl) amino-9-ergoline, ergocomine, 9,10-dihydroergocornine, D-2-halo-6-alkyl-8-substituted ergolines, D-2-bromo-6-methyl-8-cyanomethylergoline, carbidopa, benserazide, and other dopadecarboxylase inhibitors, L-dopa, dopamine, and non toxic salts thereof.

The compound(s) used according to the invention can also be used conjointly with agents acting on the ATP-dependent potassium channel of the β-cells, such as glibenclamide, glipizide, gliclazide, and AG-EE 623 ZW. The compound(s) may also advantageously be applied in combination with other oral agents such as metformin and related compounds or glucosidase inhibitors as, for example, acarbose.

(vi). Hematopoietic Agonists.

In still another aspect, the present invention provides a method for stimulating hematopoietic cells in culture or in vivo. In certain embodiments, the subject DPP IV pro-inhibitors include an address moiety that is a substrate for a protease that is expressed in bone marrow.

According to one aspect of the invention, a method for stimulating hematopoietic cells in vitro is provided. The method involves (1) contacting the hematopoietic cells with a sufficient amount of an DPP IV pro-inhibitor to increase the number of hematopoietic cells and/or the differentiation of such hematopoietic cells relative to the number and differentiation of hematopoietic cells.

One important aspect of the invention involves restoring or preventing a deficiency in hematopoietic cell number in a subject. Such deficiencies can arise, for example, from genetic abnormalities, from disease, from stress, from chemotherapy (e.g. cytotoxic drug treatment, steroid drug treatment, immunosuppressive drug treatment, etc.) and from radiation treatment.

The pro-inhibitors of the invention can be administered alone, or in combination with additional agents for treating the condition, e.g., a different agent which stimulates activation or proliferation of said lymphocytes or hematopoietic cells. For example, the pro-inhibitors can be administered in conjunction with exogenous growth factors and cytokines which are specifically selected to achieve a particular outcome. For example, if it is desired to stimulate a particular hematopoietic cell type, then growth factors and cytokines which stimulate proliferation and differentiation of such cell type are used.

Thus, it is known that interleukins-1, 2, 3, 4, 5, 6, 7, 9, 10, 11, 12, 13, and 17 are involved in lymphocyte differentiation. Interleukins 3 and 4 are involved in mast cell differentiation. Granulocyte macrophage colony stimulating factor (GMCSF), interleukin-3 and interleukin-5 are involved in the eosinophil differentiation. GMCSF, macrophage colony stimulating factor (MCSF) and IL-3 are involved in macrophage differentiation.

GMCSF, GCSF and IL-3 are involved in neutrophil differentiation. GMSCF, IL-3, IL-6, IL-1 and TPO are involved in platelet differentiation. Flt3 Ligand is involved in dendritic cell growth. GMCSF, IL-3, and erythropoietin are involved in erythrocyte differentiation.

Finally, the self-renewal of primitive, pluripotent progenitor cells capable of sustaining hematopoiesis requires SCF, Flt3 Ligand, G-CSF, IL-3, IL-6 and IL-11. Various combinations for achieving a desired result will be apparent to those of ordinary skill in the art.

(vii). Proteasome Inhibitors.

In other embodiments, the pro-soft inhibitors produce inhibitor moieties that are potent and highly selective proteasome inhibitors and can be employed to inhibit proteasome function. Inhibition of proteasome function has a number of practical therapeutic and prophylactic applications. However, because the proteasome is ubiquitous to living cells, there is a desire to provide embodiments of the subject pro-inhibitor that release a proteasome inhibitor using an address moiety that is cleaved at or in proximity to the intended target cells. For instance, the proteasome pro-inhibitors embodiments can include address moieties that are substrates for proteases that are expressed in tumors or other cells which are undergoing unwanted proliferation, or expressed in the tissue surrounding the tumor or other target proliferating cells. For instance, the address moiety can be a substrate for a protease expressed in the stromal layer adjacent a tumor.

In certain embodiments, the proteasome pro-inhibitors of the present invention provide a method of reducing the rate of degradation of p53 and other tumor suppressors.

Such pro-inhibitors are contemplated as possessing important practical application in treating cell proliferative diseases, such as cancer, restenosis and psoriasis.

In certain embodiments, proteasome pro-inhibitors can be used to inhibit the processing of internalized cellular or viral antigens into antigenic peptides that bind to MHC-I molecules in an animal, and are therefore useful for treating autoimmune diseases and preventing rejection of foreign tissues, such as transplanted organs or grafts.

Finally, the present invention relates to the use of proteasome pro-inhibitors for treating specific conditions in animals that are mediated or exacerbated, directly or indirectly, by proteasome functions. These conditions include inflammatory conditions, such as tissue rejection, organ rejection, arthritis, infection, dermatoses, inflammatory bowel disease, asthma, osteoporosis, osteoarthritis and autoimmune disease such as lupus and multiple sclerosis; cell proliferative diseases, such as cancer, psoriasis and restenosis; and accelerated muscle protein breakdown that accompanies various physiological and pathological states and is responsible to a large extent for the loss of muscle mass (atrophy) that follows nerve injury, fasting, fever, acidosis, and certain endocrinopathies.

Compounds of the present invention inhibit the growth of cancer cells. Thus, the compounds can be employed to treat cancer, psoriasis, restenosis or other cell proliferative diseases in a patient in need thereof.

By the term "treatment of cancer" or "treating cancer" is intended description of an activity of compounds of the present invention wherein said activity prevents or alleviates or ameliorates any of the specific phenomena known in the art to be associated with the pathology commonly known as "cancer." The term "cancer" refers to the spectrum of pathological symptoms associated with the initiation or progression, as well as metastasis, of malignant tumors. By the term "tumor" is intended, for the purpose of the present invention, a new growth of tissue in which the multiplication of cells is uncontrolled and progressive. The tumor that is particularly relevant to the invention is the malignant tumor, one in which the primary tumor has the properties of invasion or metastasis or which shows a greater degree of anaplasia than do benign tumors.

Thus, "treatment of cancer" or "treating cancer" refers to an activity that prevents, alleviates or ameliorates any of the primary phenomena (initiation, progression, metastasis) or secondary symptoms associated with the disease. Cancers that are treatable are broadly divided into the categories of carcinoma, lymphoma and sarcoma. Examples of carcinomas that can be treated by the composition of the present invention include, but are not limited to: adenocarcinoma, acinic cell adenocarcinoma, adrenal cortical carcinomas, alveoli cell carcinoma, anaplastic carcinoma, basaloid carcinoma, basal cell carcinoma, bronchiolar carcinoma, bronchogenic carcinoma, renaladinol carcinoma, embryonal carcinoma, anometroid carcinoma, fibrolamolar liver cell carcinoma, follicular carcinomas, giant cell carcinomas, hepatocellular carcinoma, intraepidermal carcinoma, intraepithelial carcinoma, leptomanigio carcinoma, medullary carcinoma, melanotic carcinoma, menigual carcinoma, mesometonephric carcinoma, oat cell carcinoma, squamal cell carcinoma, sweat gland carcinoma, transitional cell carcinoma, and tubular cell carcinoma. Sarcomas that can be treated by the composition of the present invention include, but are not limited to: amelioblastic sarcoma, angiolithic sarcoma, botryoid sarcoma, endometrial stroma sarcoma, ewing sarcoma, fascicular sarcoma, giant cell sarcoma, granulositic sarcoma, immunoblastic sarcoma, juxaccordial osteogenic sarcoma, coppices sarcoma, leukocytic sarcoma (leukemia), lymphatic sarcoma (lympho sarcoma), medullary sarcoma, myeloid sarcoma (granulocitic sarcoma), austiogenci sarcoma, periostea sarcoma, reticulum cell sarcoma (histiocytic lymphoma), round cell sarcoma, spindle cell sarcoma, synovial sarcoma, and telangiectatic audiogenic sarcoma.

Lymphomas that can be treated by the composition of the present invention include, but are not limited to: Hodgkin's disease and lymphocytic lymphomas, such as Burkitt's lymphoma, NPDL, NML, NH and diffuse lymphomas.

In other embodiments, certain of the proteasome pro-inhibitors employed in the practice of the present invention are capable of preventing this activation of NF-kB.

Blocking NF-kB activity is contemplated as possessing important practical application in various areas of medicine, e.g., inflammation, sepsis, AIDS, and the like.

In certain embodiments, the compounds of the present invention can be formulated in topical form for treatment of skin disorders selected from psoriasis, dermatitis, Lichen planus, acne, and disorders marked by hyperproliferation of skin cells.

In certain embodiments, the compounds of the present invention can be formulated in topical form for treatment of uncontrolled hair growth.

(viii). Pharmaceutical Compositions

While it is possible for a compound of the present invention to be administered alone, in certain cases it is preferable to administer the compound as a pharmaceutical formulation (composition). Protease inhibitors according to the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Compounds prepared as described herein can be administered in various forms, depending on the disorder to be treated and the age, condition, and body weight of the patient, as is well known in the art. For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent, or a coating agent. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses.

The precise time of administration and/or amount of the compound that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, e.g., Berge et al. *J. Pharm. Sci.* 1977, 66, 1-19)

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, e.g., Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol, and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

Methods of preparing these formulations or compositions include the step of bringing into association a compound(s) with the carrier and, optionally, one or more accessory ingredients. In general, the formulations are prepared by uniformly and intimately bringing into association a ligand with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes, and the like, each containing a predetermined amount of a compound(s) as an active ingredient. A compound may also be administered as a bolus, electuary or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more compound(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of a compound(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to compound(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound(s), excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

The compound(s) can be alternatively administered by aerosol. This is accomplished by preparing an aqueous aerosol, liposomal preparation, or solid particles containing the compound. A non-aqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Medicaments which may be administered in inhalant or aerosol formulations according to the invention include protease inhibitor prodrugs useful in inhalation therapy which may be presented in a form which is soluble or substantially soluble in the selected propellant system.

The particle size of the particulate medicament should be such as to permit inhalation of substantially all of the medicament into the lungs upon administration of the aerosol formulation and will thus desirably be less than 20 microns, preferably in the range 1 to 10 microns, e.g., 1 to 5 microns. The particle size of the medicament may be reduced by conventional means, for example by milling or micronisation.

Administration of medicament may be indicated for the treatment of mild, moderate or severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example from 1 to 8 times per day, giving for example 1, 2, 3 or 4 puffs each time. Preferably, administration may be one time per day.

For administration, the drug is suitably inhaled from a nebulizer, from a pressurized metered dose inhaler, or as a dry powder from a dry powder inhaler (e.g., sold as TURBUHALER®) or from a dry powder inhaler utilizing gelatin, plastic or other capsules, cartridges or blister packs.

A diluent or carrier, generally non-toxic and chemically inert to the medicament; e.g., lactose, dextran, mannitol, glucose or any additives that will give the medicament a desired taste, can be added to the powdered medicament.

The micronized mixture may be suspended or dissolved in a liquid propellant mixture which is kept in a container that is sealed with a metering valve and fitted into a plastic actuator. The propellants used may be halocarbons of different chemical formulae. The most frequently used halocarbon propellants are trichlorofluoromethane, dichlorodifluoromethane, dichlorotetrafluoroethane, tetrafluoroethane, and 1,1-difluoroethane. Low concentrations of a surfactant such as sorbitan trioleate, lecithin, disodium dioctylsulphosuccinate, or oleic acid may also be used to improve the physical stability.

Transdermal patches have the added advantage of providing controlled delivery of a compound(s) to the body. Such dosage forms can be made by dissolving or dispersing the agent in the proper medium. Absorption enhancers can also be used to increase the flux of the compound(s) across the skin. The rate of such flux can be controlled by either providing a rate controlling membrane or dispersing the peptidomimetic in a polymer matrix or gel.

Ophthalmic formulations, eye ointments, powders, solutions, and the like, are also contemplated as being within the scope of this invention.

Pharmaceutical compositions of this invention suitable for parenteral administration comprise one or more compounds(s) in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of compound(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds(s) of the present invention are administered as pharmaceuticals to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of agents may be given orally, parenterally, topically, or rectally. They are of course given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

These compounds(s) may be administered to humans and other animals for therapy by any suitable route of administration, including orally, nasally, as by, for example, a spray, rectally, intravaginally, parenterally, intracistemally, and topically, as by powders, ointments or drops, including buccally and sublingually.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as *Applied Animal Nutrition*; San Francisco: Freedman, 1969; or *Livestock Feeds and Feeding*; Corvallis: O & B Books, 1977).

Regardless of the route of administration selected, the compound(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

(ix). Pharmaceutical Packages and Manufacture.

One aspect of the present invention provides a packaged pharmaceutical comprising one or more inhibitors of the present invention formulated in a pharmaceutically acceptable excipient, in association with instructions (written and/or pictorial) describing the recommended dosage and/or administration of the formulation to a patient. Such instructions may include details for treating or preventing a diseases, and optionally, warnings of possible side effects and drug-drug or drug-food interactions.

Another aspect of the invention relates to the use of the subject inhibitors in the manufacture of a medicament for the treatment of a disorder for which inhibition of the target protease of the inhibitor moiety G provides a therapeutic benefit to a patient. Exemplary disorders are enumerated below.

Yet another aspect of the invention relates to a method for conducting a pharmaceutical business, which includes:
  a. manufacturing one or more of the subject inhibitors; and
  b. marketing to healthcare providers the benefits of using the preparation to treat or prevent any of the diseases or indications cited herein.

In certain embodiments, the subject business method can include providing a distribution network for selling the preparation. It may also include providing instruction material to patients or physicians for using the preparation to treat and prevent any of the diseases or indications cited herein.

(x). Combinatorial Libraries

The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g., a variegated library of compounds represented above, can be screened rapidly in high throughput assays in order to identify potential protease inhibitor lead compounds, as well as to refine the specificity, toxicity, and/or cytotoxic-kinetic profile of a lead compound.

Simply for illustration, a combinatorial library for the purposes of the present invention is a mixture of chemically related compounds which may be screened together for a desired property. The preparation of many related compounds in a single reaction greatly reduces and simplifies the number of screening processes which need to be carried out. Screening for the appropriate physical properties can be done by conventional methods.

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject protease inhibitors. See, for example, Blondelle et al. *Trends Anal. Chem.* 1995, 14, 83; the Affymax U.S. Pat. Nos. 5,359,115 and 5,362,899: the Ellman U.S. Pat. No. 5,288,514: the Still et al. PCT publication WO 94/08051; the ArQule U.S. Pat. Nos. 5,736,412 and 5,712,171; Chen et al. *J. Am. Chem. Soc.* 1994, 116, 2661: Kerr et al. *J. Am. Chem. Soc.* 1993, 115, 252; PCT publications WO92/10092, WO93/09668 and WO91/07087; and the Lerner et al. PCT publication WO93/20242). Accordingly, a variety of libraries on the order of about 100 to 1,000,000 or more diversomers of the subject protease inhibitors can be synthesized and screened for particular activity or property.

In an exemplary embodiment, a library of candidate protease inhibitor diversomers can be synthesized utilizing a scheme adapted to the techniques described in the Still et al. PCT publication WO 94/08051, e.g., being linked to a polymer bead by a hydrolysable or photolyzable group, optionally located at one of the positions of the candidate agonists or a substituent of a synthetic intermediate. According to the Still et al. technique, the library is synthesized on a set of beads, each bead including a set of tags identifying the particular diversomer on that bead. The bead library can then be "plated" with proteases for which an inhibitor is sought. The diversomers can be released from the bead, e.g., by hydrolysis.

The structures of the compounds useful in the present invention lend themselves readily to efficient synthesis. The nature of the structures of the subject compounds, as generally set forth above, allows the rapid combinatorial assembly of such compounds. For example, as in the scheme set forth below, an activated aryl group, such as an aryl triflate or bromide, attached to a bead or other solid support can be linked to another aryl group by performing a Stille or Suzuki coupling with an aryl stannane or an aryl boronic acid. If the second aryl group is functionalized with an aldehyde, an amine substituent can be added through a reductive amination. Alternatively, the second aryl group could be functionalized with a leaving group, such as a triflate, tosylate, or halide, capable of being displaced by an amine. Or, the second aryl group may be functionalized with an amine group capable of undergoing reductive amination with an amine, e.g., $CyKNH_2$. Other possible coupling techniques include transition metal-mediated amine arylation reactions. The resultant secondary amine can then be further functionalized by an acylation, alkylation, or arylation to generate a tertiary amine or amide which can then be cleaved from the resin or support. These reactions generally are quite mild and have been successfully applied in combinatorial solid-phase synthesis schemes. Furthermore, the wide range of substrates and coupling partners suitable and available for these reactions permits the rapid assembly of large, diverse libraries of compounds for testing in assays as set forth herein. For certain schemes, and for certain substitutions on the various substituents of the subject compounds, one of skill in the art will recognize the need for masking certain functional groups with a suitable protecting group. Such techniques are well known in the art and are easily applied to combinatorial synthesis schemes.

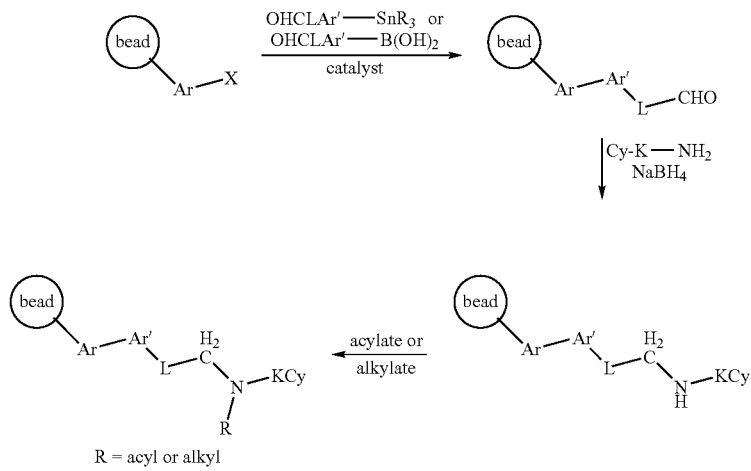

Many variations on the above and related pathways permit the synthesis of widely diverse libraries of compounds which may be tested as protease inhibitors.

Variations, modifications, and other implementations of what is described herein will occur to those of ordinary skill without departing from the spirit and the scope of the invention. Accordingly, the invention is not to be limited only to the preceding illustrative description. For additional illustrative features that may be used with the invention, including the embodiments described here, refer to the documents listed herein above and incorporated by reference in their entirety. All operative combinations between the above described illustrative embodiments and those features described below are considered to be potentially patentable embodiments of the invention.

EXEMPLIFICATION

The invention now being generally described, it will be more readily understood by reference to the following examples which are included merely for purposes of illustration of certain aspects and embodiments of the present invention, and are not intended to limit the invention.

EXAMPLE 1

General Procedure for Synthesis of Thioxo-Amide-Containing Dipeptide (boro)Amino-Acid-Containing Analogues (Xaa-(C(S))-(boro)Xaa')

Overview

Initially, a B-terminal protected form of a (boro)amino acid analogue is acylated with an activated form of an N-protected amino acid (or oligopeptide) to give a B-protected and N-protected (boro)amino acid-containing dipeptide (or oligopeptide) analogue. The B-protected and N-protected (boro) amino acid analogue is then transformed to the corresponding thioxo amide compound using, e.g., Lawesson's Reagent. Finally, the thioxo-amide-containing (boro)amino acid dipeptide (or oligopeptide) analogue is deprotected to provide the thioxo-amide-containing (boro)amino acid dipeptide (or oligopeptide).

Application to Preparation of Ala-boroPro (Thioxo Amide)

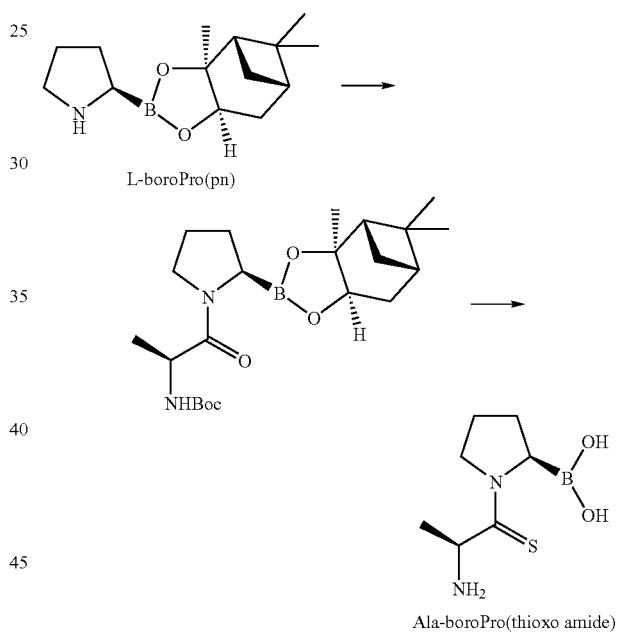

To a stirred solution of N-Boc-L-Alanine (1.9 g, 10 mmol) and L-boroPro(pn).HCl (2.9 g, 101 mmol) in anhydrous DMF (30 mL) were added HATU (4.0 mg, 10.5 mmol) and N,N-diisopropylethylamine (DIPEA, 4.0 mL, 23 mmol) at 0° C. under argon atmosphere. The cooling bath was removed and the resulting mixture was stirred at room temperature for 1 hr, and then was concentrated in vacuo under 30° C. The residue was dissolved in ethyl acetate (100 mL), washed sequentially with $KHSO_4$ (0.1 M, 3×15 mL), aq. $NaHCO_3$ (5%, 3×10 mL), brine (3×10 mL) and dried ($MgSO_4$) and evaporated. The crude product was purified by flash column chromatography over silica gel (1:1, hexanes/EtOAc) to afford the pure coupling product as a white powder which was added to a stirred suspension of Lawesson reagent (1.8 g, 4.5 mmol) in anhydrous toluene (100 mL) at room temperature. The resulting mixture was then stirred at 80° C. for 4 hr. After removal of the solvent, the crude product was purified by flash column chromatography over silica gel (2:1, hexanes/EtOAc)

to afford N-Boc-Ala-boropro(pn) (thioxo amide) as a white powder. 3.1 g of this thioxo amide (7.1 mmol) was dissolved in anhydrous dichloromethane (40 mL), cooled to −78° C., a solution of boron trichloride in dichloromethane (35 mL, 1.0 M) was added and stirred for 1 hr. The resulting mixture was evaporated to dryness under reduced pressure and co-evaporated using anhydrous methanol (3×15 mL). The residue was then partitioned between water (30 mL) and ether (30 mL). The aqueous phase was separated and washed with ether (2×20 mL). Concentrated the aqueous phase in vacuo and then purified by semi-preparative RP-HPLC, lyophilized to afford the target compound Ala-boroPro (thioxo amide) as a white powder. $^1$H NMR (D$_2$O, pH 2.01, δ): 1.51 (d, J=6.7 Hz, 3H, CH$_3$), 1.83-1.90 (m, 1H, —CH$_2$CH$_A$H$_B$CHB—), 2.08-2.25 (m, 3H, —CH$_2$CH$_A$H$_B$CHB—), 3.50-3.56 (m, 1H, —CH$_2$CH$_2$CHB—), 3.62-3.69 (m, 1H, —NCH$_A$H$_B$CH$_2$CH$_2$—), 3.92-4.00 (m, 1H, —NCH$_A$H$_B$CH$_2$CH$_2$—), 4.55 (q, J=6.6 Hz, 1H, CH$_3$CHNH$_2$—); $^{11}$B NMR (D$_2$O, pH 2.01, δ): 9.5; LC-MS (ESI+) for C$_7$H$_{15}$BN$_2$O$_2$S nm/z (rel intensity): 369.2 ([2×(M−H$_2$O)+H]$^+$, 21), 203.1 ([M+H]$^+$, 58), 186.1 ([M−NH$_2$]$^+$, 100). HRMS: calcd for C$_7$H$_{16}$BN$_2$O$_2$S, [M+H]$^+$, 203.1026, found 203.1030.

EXAMPLE 2

DPIV Inhibition Assay

The inhibitor solution is prepared by dissolving 3-5 mg of inhibitor in pH 2 solution (0.01 N HCl), such that the concentration of the solution is equal to 1 mg/10 μL. A 10 μL sample of this solution is then added to 990 μL of pH 8 buffer (0.1 M HEPES, 0.14 M NaCl), and the solution is allowed to stand at room temperature overnight.

The enzyme solution is prepared by diluting 20 μL of DPIV (concentration 2.5 μM) into 40 mL of pH 8 buffer.

The substrate solution is prepared by dissolving 2.0 mg of L-alanyl-L-proline-para-nitroanilide into 20 mL of pH 8 buffer.

250 μL of enzyme solution is added to well #B1 to #H1, #A2 to #H2, and #A3 to #H3 of a 96 well plate, while well #A1 receives 250 μL of pH 8 buffer instead of enzyme solution. 90 μL of pH 8 buffer is then added to column 5 (from well #A5 to #H5).

A 1:10 dilution is then performed by adding inhibitor solution to #A5 and the solution is mixed well before transferring 10 μL of this solution from #A5 to #B5. The solution in #B5 is then mixed well before transferring 10 μL of this solution from #B5 to #C5. The solution in #C5 is then mixed well before transferring 10 μL of this solution from #C5 to #D5. The solution in #D5 is then mixed well before transferring 10 μL of this solution from #D5 to #E5. The solution in #E5 is then mixed well before transferring 10 μL of this solution from #E5 to #F5. The solution in #F5 is then mixed well before transferring 10 μL of this solution from #F5 to #G5. The solution in #G5 is then mixed well before transferring 10 μL of this solution from #G5 to #H5.

A 30 μL aliquot is then transferred from #H5 to #H3 for row H, and the contents are mixed well. The analogous procedure is repeated for rows G, F, E, D, C, B, and A sequentially. The plate is then shaken on a plate shaker for 5 min before allowing the plate to incubate at room temperature for an additional 5 min.

Once the plate has been allowed to incubate, 30 μL of substrate is added to each well except well #A1. The plate is then placed on a plate shaker for 5 min before allowing the plate to incubate at room temperature for 25 min. The absorbance is then immediately read at a wavelength of 410 nm.

EXAMPLE 3

Selectivity for Dipeptidyl Peptidase Isoforms

The assay described in Example 2 is used to determine the IC$_{50}$ values for several compounds of the invention. In this example, the assay is conducted for DPIV and DP8 or DP9. The ratio of IC$_{50}$ values for each tested compound is calculated in order to determine the selectivity for the DPIV isoform. IC$_{50}$ values were measured at the same pH throughout the assay.

Preferred compounds of the invention inhibit DPIV at least 10 times, preferably at least 100 times, more strongly than they inhibit DP8 and/or DP9, i.e., have an IC$_{50}$ at least 10 (or 100) times lower against DPIV than against DP8 and/or DP9.

| IC50s Inhibitor | DPPIV pH 2 | pH 7.8 | Ratio | DP8 pH 2 | pH 7.8 | Ratio | DP9 pH 2 | pH 7.8 | Ratio | Ratio DPP8 to DPIV (pH 2) | Ratio DP9 To DPIV (pH 2) |
|---|---|---|---|---|---|---|---|---|---|---|---|
| Pro-boro Pro (thioxam) | 0.75 nM | nd | | 2.5 nM | 1.8 μM | 720 | 1.9 nM | 340 nM | 180 | 3.2 | 2.5 |
| Pro-boro Ala (thioxam) | 76 nM | 310 nM | 4.1 | 140 nM | 310 nM | 2.2 | 85 nM | 110 nM | 1.3 | 1.8 | 1.1 |
| Glu-boro Pro (thioxam) | 4.6 nM | 890 nM | 190 | 16 nM | 2.0 μM | 130 | 8.7 nM | 1.8 μM | 180 | 3.4 | 1.9 |
| Ala-boro Pro (thioxam) | 0.74 nM | 1.3 nM | 1700 | 3.8 nM | 2.4 μM | 630 | 8.4 nM | 4.2 μM | 500 | 5 | 11 |

EXAMPLE 4

DPP Inhibition: Thioxamide v. Oxoamide

The inhibitory activity of a compound may be tested easily. DP-IV is purified from pig kidney cortex by the method of Barth et al. (Acta Biol. Med. Germ. 32:157, 1974) and Wolf et al. (Acta Biol. Med. Germ. 37:409, 1978) and from human placenta by the method of Puschel et al. (Eur. J. Biochem. 126:359, 1982). A compound is then screened for its ability to inhibit the protease activity of DP-IV with respect to a natural substrate. For example, the activity of DP-IV, isolated from porcine kidneys by the method of Wolf et al. (ACTA Bio. Mes. Ger. 37:409, 1972), was measured using Ala-Pro-p-nitroanilide as a substrate. Briefly, a reaction containing 50 micromol sodium Hepes (pH 7.8), 10 micromol Ala-Pro-p-nitroanilide, 6 milliunits of DP-IV, and 2% (vol/vol) dimethylformamide in a total volume of 1.0 mL. The reaction was initiated by the addition of enzyme and reaction rates were measured at 25 C; formation of reaction product (para-nitroanilide) in the presence and absence of a test compound can be detected photometrically, e.g., at 410 nm.

| Inhibitor | Structure | $IC_{50}$ (pH 2.0) | $IC_{50}$ (pH 8.0) | Inactivation Index |
|---|---|---|---|---|
| Ala-boroPro | Exact Mass: 186.1.2 | 0.26 nM | 1.4 uM | 5,400 |
| Ala-boroPro Thioxamide | Exact Mass: 238.07 | 0.35 nM | 20 uM | 57,000 |
| Val-boroAla | Exact Mass: 188.13 | 3.5 nM | 9.0 nM | 2.6 |
| Val-boroAla Thioxamide | Exact Mass: 204.11 | 73 nM | 220 nM | 3.0 |
| Ala-boroAla | Exact Mass: 160.10 | 63 nM | 440 nM | 7.0 |
| Ala-boroAla Thioxamide | Exact Mass: 176.08 | 6.5 uM | 7.7 uM | 1.2 |
| Val-boroPro | Exact Mass: 214.15 | 1.7 nM | 1.2 uM | 710 |

-continued

| Inhibitor | | IC$_{50}$ (pH 2.0) | IC$_{50}$ (pH 8.0) | Inactivation Index |
|---|---|---|---|---|
| Val-boroPro Thioxamide | Exact Mass: 230.13 | 44 nM | 5.9 uM | 130 |
| Chg-boroPro | Exact Mass: 246.18 | 1 nM | 380 nM | 380 |
| Chg-boroPro Thioxamide | Exact Mass: 270.16 | 4 nM | 9 uM | 2,300 |
| Gly-boroPro | Exact Mass: 172.10 | 1 nM | 7 uM | 7,000 |
| Gly-boroPro Thioxamide | Exact Mass: 188.08 | 3 nM | 1.9 uM | 630 |
| NVP-LAF237 analogue | Exact Mass: 322.21 | 42 nM | 72 nM | 1.7 |

-continued
| Inhibitor | | IC$_{50}$ (pH 2.0) | IC$_{50}$ (pH 8.0) | Inactivation Index |
|---|---|---|---|---|
| NVP-LAF237 analogue Thioxamide | 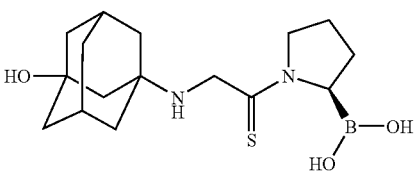 Exact Mass: 338.18 | 160 nM | 40 uM | 250 |
| N-(Benzyl)-Gly-boroPro | 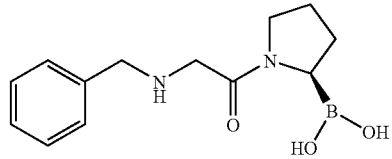 Exact Mass: 262.15 | 9.5 nM | 69 uM | 7,300 |
| N-(Benzyl)-Gly-boroPro Thioxamide | 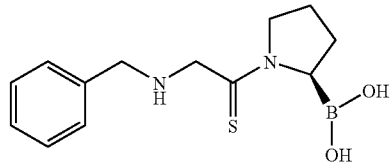 Exact Mass: 278.13 | 24 nM | 170 nM | 7.1 |
| Asp-boroPro | 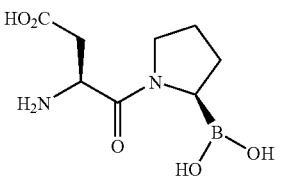 Exact Mass: 230.11 | 200 nM | 35 uM | 180 |
| Asp-boroPro Thioxamide | 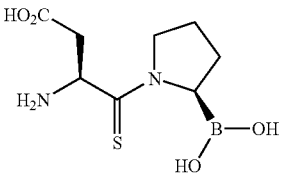 Exact Mass: 246.08 | 17 nM | 28 uM | 1,700 |
| Glu-boroPro | 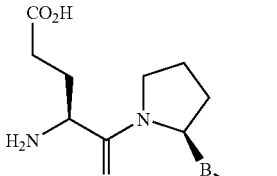 Exact Mass: 244.12 | 6 nM | 3 uM | 500 |
| Glu-boroPro Thioxamide | 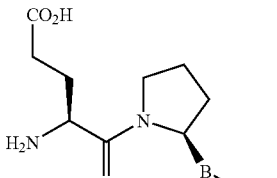 Exact Mass: 260.10 | 4.6 nM | 890 nM | 190 |

-continued

| Inhibitor | | IC$_{50}$ (pH 2.0) | IC$_{50}$ (pH 8.0) | Inactivation Index |
|---|---|---|---|---|
| Aad-boroPro | Exact Mass: 258.14 | 4.5 nM | 7.4 uM | 1,600 |
| Aad-boroPro Thioxamide | Exact Mass: 274.12 | 1.6 nM | 19 uM | 12,000 |
| Trp-boroPro | Exact Mass: 301.16 | 2 nM | 3 uM | 1500 |
| Trp-boroPro Thioxamide | Exact Mass: 317.14 | 1.6 nM | 700 nM | 440 |

-continued

| Inhibitor | | IC$_{50}$ (pH 2.0) | IC$_{50}$ (pH 8.0) | Inactivation Index |
|---|---|---|---|---|
| Arg-boroPro | (structure) Exact Mass: 271.1.6 | 1.8 nM | 7.1 uM | 3,900 |
| Arg-boroPro Thioxamide | (structure) Exact Mass: 287.16 | 1.2 nM | No inhibition | N/A |
| Pro-boroPro | (structure) C$_9$H$_{12}$BN$_2$O$_3$ Mol. Wt.: 212.05 | 1.1 nM | 23 uM | 21,000 |
| Pro-boroPro Thioxamide | (structure) Exact Mass: 228.11 | 6.4 nM | 7 uM | 1,100 |

EXAMPLE 5

X-BoroLeu Proteasome Inhibition: Thioxamide v. Oxoamide

The 26S proteasome is the multi-catalytic protease responsible for the majority of intracellular protein turnover in eukaryotic cells, including proteolytic degradation of damaged, oxidized or misfolded proteins, as well as processing or degradation of key regulatory proteins required for various cellular function (Ciechanover, Cell 79: 13-21 (1994); Coux et al., Ann. Rev. Biochem. 65:801-847 (1995); Goldberg et al., Chemistry & Biology 2:503-508 (1995)). Protein substrates are first marked for degradation by covalent conjugation to multiple molecules of a small protein, ubiquitin. The resultant polyubiquitinated protein is then recognized and degraded by the 26S proteasome.

Constituting the catalytic core of the 26S proteasome is the 20S proteasome, a multi-subunit complex of approximately 700 kDa molecular weight. Coux et al. (Ann. Rev. Biochem. 65:801-847 (1995)) teaches that the 20S proteasome does not by itself degrade ubiquitinated proteins, but does possess multiple peptidase activities. Based on substrate preferences, Coux et al. characterizes these activities as chymotrypsin-like, trypsin-like, post-glutamyl hydrolase, branched chain amino acid preferring, and small neutral amino acid preferring. Coux et al. also teaches that a dramatic activation of 20S proteasome activity can be induced by various in vitro treatments, such as heating to 55.degree. C., incubation with basic polypeptides, sodium dodecyl sulfate (SDS), guanidine HCl or fatty acids, dialysis against water, or by physiological regulators such as PA28 or PA700. McCormack et al. (Biochemistry 37:7792-7800 (1998)) teaches that a variety of peptide substrates, including Suc-Leu-Leu-Val-Tyr-AMC, Z-Leu-Leu-Arg-AMC, and Z-Leu-Leu-Glu-2NA, wherein Suc is N-succinyl, AMC is 7-amino-4-methylcoumarin, and 2NA is 2-naphthylamine, are cleaved by the 20S proteasome.

The ubiquitin-proteasome pathway plays a central role in a large number of physiological processes. Deshaies (Trends in Cell Biol. 5: 428-434 (1995)) and Hoyt (Cell 91:149-151

(1997)) teach that regulated proteolysis of cell cycle proteins, including cyclins, cyclin-dependent kinase inhibitors, and tumor suppressor proteins, is required for controlled cell cycle progression and that proteolysis of these proteins occurs via the ubiquitin-proteasome pathway. Palombella et al., WO 95/25533 teaches that activation of the transcription factor NF-kappa-B, which itself plays a central role in the regulation of genes involved in the immune and inflammatory responses, is dependent upon the proteasome-mediated degradation of an inhibitory protein, Ikappa-B-.alpha. Goldberg and Rock, WO 94/17816 discloses that the continual turnover of cellular proteins by the ubiquitin-proteasome pathway plays an essential role in antigen presentation.

Inhibition of proteasome activity thus offers a promising new approach for therapeutic intervention in these and other conditions directly or indirectly mediated by the proteolytic function of the proteasome. Goldberg et al. (Chemistry & Biology 2:503-508 (1995)) teaches that proteasome inhibitors block the inflammatory response in vivo in animal models of human disease.

Compounds may be screened for their ability to inhibit the ATP-ubiquitin-dependent degradative process by measurement proteolysis in cultured cells (Rock et al., Cell, vol. 78:761 (1994)). For example, the degradation of long-lived intracellular proteins can be measured in mouse C2C12 myoblast cells. Cells are incubated with $^{35}$S-methionine for 48 hours to label long-lived proteins and then chased for 2 hours with medium containing unlabeled methionine. After the chase period, the cells are incubated for 4 hours in the presence or absence of the test compound. The amount of protein degradation in the cell can be measured by quantitating the trichloroacetic acid soluble radioactivity released from the prelabeled proteins into the growth medium (an indicator of intracellular proteolysis).

Compounds can also be tested for their ability to reduce muscle wasting in vivo. Urinary excretion of the modified amino acid 3-methyl histidine (3-MH) is probably the most well characterized method for studying myofibrillar protein degradation in vivo (see Young and Munro, Federation Proc. 37:229-2300 (1978)). 3-Methylhistidine is a post-translationally modified amino acid which cannot be reutilized for protein synthesis, and it is only known to occur in actin and myosin. It occurs in actin isolated from all sources, including cytoplasmic actin from many different cell types. It also occurs in the myosin heavy chain of fast-twitch (white, type II) muscle fibers, but it is absent from myosin of cardiac muscle and myosin of slow-twitch (red, type I) muscle fibers. Due to its presence in actin of other tissues than skeletal muscle, other tissues will contribute to urinary 3-MH. Skeletal muscle has been estimated to contribute 38-74% of the urinary 3-MH in normal rats and 79-86% of the urinary 3-MH in rats treated with corticosterone (100 mg/kg/day subcutaneously) for 2-4 days (Millward and Bates, Biochem. J. 214: 607-615 (1983); Kayali, et al., Am. J. Physiol. 252:E621-E626 (1987)).

High-dose glucocorticoid treatment can be used to induce a state of muscle wasting in rats. Treating rats with daily subcutaneous injections of corticosterone (100 mg/kg) causes an increase of approximately 2-fold in urinary 3-MH. The increase in excretion of 3-MH is transient, with a peak increase after 2-4 days of treatment and a return to basal values after 6-7 days of treatment (Odedra, et al., Biochem. J. 214:617-627 (1983); Kayali, et al., Am. J. Physiol. 252:E621-E626 (1987)). Glucocorticoids have been shown to activate the ATP-ubiquitin-dependent proteolytic pathway in skeletal muscle (Wing and Goldberg, Am. J. Physiol. 264:E668-E676 (1993)) and proteasome inhibitors are therefore expected to inhibit the muscle wasting that occurs after glucocorticoid treatment.

| Inhibitor | Structure | IC$_{50}$ (pH 2.0) | IC$_{50}$ (pH 7.6) | Inactivation Index |
|---|---|---|---|---|
| Ala-boroLeu | Exact Mass: 202.15 | 31 nM | 100 nM | 3.2 |
| Ala-boroLeu Thioxamide | Exact Mass: 218.13 | 0.85 uM | 92 uM | 110 |

-continued
| Inhibitor | | IC$_{50}$ (pH 2.0) | IC$_{50}$ (pH 7.6) | Inactivation Index |
|---|---|---|---|---|
| Asp-boroLeu Thioxamide | 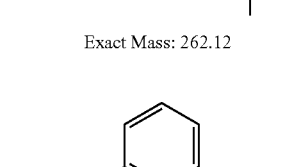 Exact Mass: 262.12 | 4.6 uM | 10 uM | 2.2 |
| Phe-boroLeu (free Velcade) | 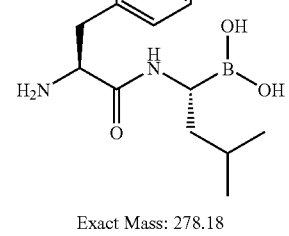 Exact Mass: 278.18 | 16 nM | 120 nM | 7.5 |
| Phe-boroLeu Thioxamide | 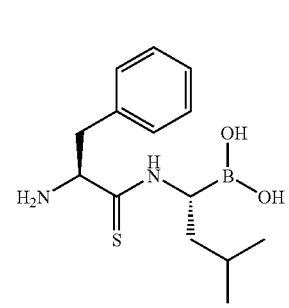 Exact Mass: 294.16 | 0.71 uM | 14 uM | 20 |
| Gly-boroLeu | 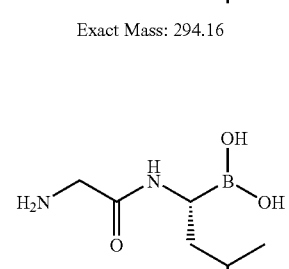 Exact Mass: 188.13 | 14 nM | 160 nM | 11 |
| Gly-boroLeu Thioxamide | 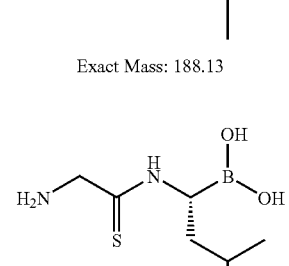 Exact Mass: 204.11 | 4.9 uM | 100 uM | 20 |

| Inhibitor | | IC$_{50}$ (pH 2.0) | IC$_{50}$ (pH 7.6) | Inactivation Index |
|---|---|---|---|---|
| Pyz-Gly-boroLeu | Exact Mass: 294.15 | 100 nM | 120 nM | 1.2 |
| N-(Pyrazine-2-carbothio)-Gly-boroLeu | Exact Mass: 310.13 | 77 nM | 350 nM | 4.5 |
| N-(Pyrazine-2-carbonyl)-Gly-boroLeu Thioxamide | Exact Mass: 310.13 | 5.8 uM | 22 uM | 3.8 |
| Pyz-Gly-boroLeu-Perthioxamide | Exact Mass: 326.10 | 3.9 uM | 2.4 mM | 620 |

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A compound represented by:

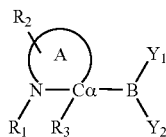

or a pharmaceutically acceptable salt thereof;

wherein
A represents a 4-8 membered heterocycle including the N and the Cα carbon;
R$_1$ represents a C-terminally linked amino acid residue or amino acid analog R$^6$; wherein the bond between R$_1$ and N is a thioxamide bond;
R$_2$ is absent or represents one or more substitutions to the ring A, each of which is independently a halogen, lower alkyl, lower alkenyl, lower alkynyl, carbonyl, carboxyl, ester, formate, ketone, thiocarbonyl, thioester, thioacetate, thioformate, amino, acylamino, amido, nitro, sulfate, sulfonate, sulfonamido, —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_7$, —(CH$_2$)$_m$—SH, —(CH$_2$)$_m$—S-lower alkyl, —(CH$_2$)$_m$—S-lower alkenyl, or —(CH$_2$)$_n$—S—(CH$_2$)$_m$—R$_7$, azido, cyano, isocyanato, thiocyanato, isothiocyanato, cyanato,

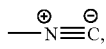

or

R₃ represents hydrogen or a halogen, lower alkyl, lower alkenyl, lower alkynyl, carbonyl, thiocarbonyl, amino, acylamino, amido, nitro, sulfate, sulfonate, a sulfonamido, —(CH₂)$_m$—R₇, —(CH₂)$_m$—OH, —(CH₂)$_m$—O-lower alkyl, —(CH₂)$_m$—O-lower alkenyl, —(CH₂)$_n$—O—(CH₂)$_m$—R₇, (CH₂)$_m$—SH, —(CH₂)$_m$—S-lower alkyl, —(CH₂)$_m$—S-lower alkenyl, or —(CH₂)$_n$—S—(CH₂)$_m$—R₇, azido, cyano, isocyanato, thiocyanato, isothiocyanato, cyanato,

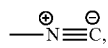

or

R₆ represents hydrogen, a halogen, alkyl, alkenyl, alkynyl, aryl, —(CH₂)$_m$—R₇, —(CH₂)$_m$—OH, —(CH₂)$_m$—O-alkyl, —(CH₂)$_m$—O-alkenyl, —(CH₂)$_m$—O-alkynyl, —(CH₂)$_m$—O—(CH₂)$_m$—R₇, —(CH₂)$_m$—SH, —(CH₂)$_m$—S-alkyl, —(CH₂)$_m$—S-alkenyl, —(CH₂)$_m$—S-alkynyl, —(CH₂)$_m$—S—(CH₂)$_m$—R₇,

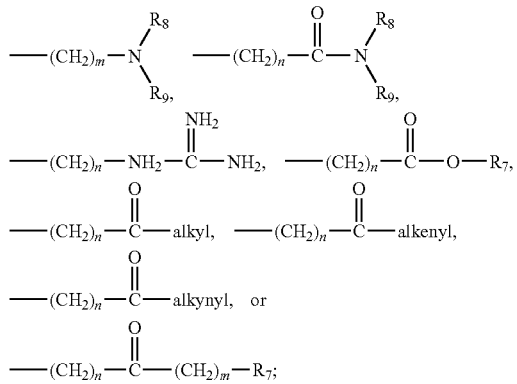

R₇ represents, for each occurrence, a substituted or unsubstituted aryl, aralkyl, cycloalkyl, cycloalkenyl, or heterocycle;
R₈ represents hydrogen, —CH₃, or —(CH₂)$_n$—CH₃;
Y₁ and Y₂, independently, are OH, or a group capable of being hydrolyzed to a hydroxyl group, or Y₁ and Y₂ are connected via a ring having from 5 to 8 atoms in the ring structure which is capable of being hydrolyzed to two hydroxyl groups;
m is zero or an integer in the range of 1 to 8; and
n is an integer in the range of 1 to 8.

2. The compound of claim 1, wherein Y₁ and Y₂, independently, are OH.

3. The compound of claim 2, wherein said compound is represented by:

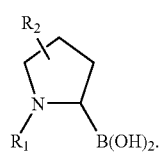

4. The compound of claim 1, wherein R₂ is absent, or represents lower alkyl or halogen.

5. The compound of claim 1, wherein R₃ is hydrogen.

6. The compound of claim 1, wherein the Cα carbon exists substantially in the R configuration.

7. The compound of claim 1, wherein the Cα carbon exists substantially in the S configuration.

8. The compound of claim 1, wherein the Cα carbon exists in a racemic mixture of R and S configurations.

9. The compound of claim 1, wherein Y₁ and Y₂ are OH.

10. The compound of claim 1, wherein R₁ is a proline, glutamate, or alanine residue.

11. The compound of claim 1, wherein R₁ is an alanine residue.

12. A compound selected from the group consisting of:

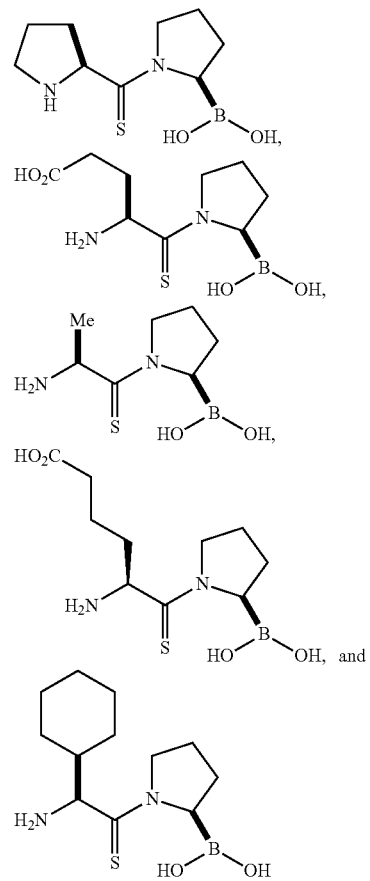

and enantiomers, diastereomers and salts thereof.

13. The compound of claim 1, wherein the compound is a protease inhibitor.

14. The compound of claim 13, wherein the compound inhibits dipeptidyl peptidase IV with a Ki of 50 nM or less.

15. The compound of claim 14, wherein the compound inhibits dipeptidyl peptidase VIII and IX with a Ki of 100 microM or greater.

16. A pharmaceutical composition, comprising a pharmaceutically acceptable carrier; and a compound of claim 1.

* * * * *

UNITED STATES PATENT AND TRADEMARK OFFICE
CERTIFICATE OF CORRECTION

PATENT NO. : 8,268,880 B2  Page 1 of 1
APPLICATION NO. : 12/096876
DATED : September 18, 2012
INVENTOR(S) : William W. Bachovchin et al.

It is certified that error appears in the above-identified patent and that said Letters Patent is hereby corrected as shown below:

In the Claims:

In claim 1, at column 112, line 49, delete "$R^6$".

In claim 1, at column 113, lines 21-40, delete the text beginning "$R_6$ represents hydrogen, a halogen," to and ending in " 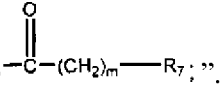 ;".

Signed and Sealed this
First Day of October, 2013

Teresa Stanek Rea
*Deputy Director of the United States Patent and Trademark Office*